(12) United States Patent
Wei et al.

(10) Patent No.: US 11,706,982 B2
(45) Date of Patent: *Jul. 18, 2023

(54) FUSED POLYCYCLIC COMPOUND, AND PREPARATION METHOD AND USE THEREOF

(71) Applicant: Ningbo Lumilan Advanced Materials Co., Ltd., Zhejiang Province (CN)

(72) Inventors: Ting-Wei Wei, Zhejiang Province (CN); Ye Cai, Zhejiang Province (CN); Huanda Ding, Zhejiang Province (CN); Kunshan Xie, Zhejiang Province (CN); Zhi-Kuan Chen, Zhejiang Province (CN)

(73) Assignee: Ningbo Lumilan Advanced Materials Co., Ltd., Zhejiang Province (CN)

( * ) Notice: Subject to any disclaimer, the term of this patent is extended or adjusted under 35 U.S.C. 154(b) by 524 days.

This patent is subject to a terminal disclaimer.

(21) Appl. No.: 16/794,285

(22) Filed: Feb. 19, 2020

(65) Prior Publication Data
US 2020/0343455 A1    Oct. 29, 2020

(30) Foreign Application Priority Data

Apr. 29, 2019   (CN) .......................... 201910353474.7

(51) Int. Cl.
| | | |
|---|---|---|
| C07D 491/048 | (2006.01) | |
| H10K 85/60 | (2023.01) | |
| C07D 495/04 | (2006.01) | |
| C07D 513/04 | (2006.01) | |
| C07D 239/70 | (2006.01) | |
| H10K 50/11 | (2023.01) | |
| H10K 50/15 | (2023.01) | |
| H10K 50/16 | (2023.01) | |
| H10K 50/17 | (2023.01) | |
| H10K 50/18 | (2023.01) | |
| H10K 50/12 | (2023.01) | |
| H10K 71/00 | (2023.01) | |
| H10K 71/16 | (2023.01) | |
| H10K 101/30 | (2023.01) | |
| H10K 101/40 | (2023.01) | |
| H10K 102/00 | (2023.01) | |

(52) U.S. Cl.
CPC ....... *H10K 85/6572* (2023.02); *C07D 239/70* (2013.01); *C07D 491/048* (2013.01); *C07D 495/04* (2013.01); *C07D 513/04* (2013.01); *H10K 50/11* (2023.02); *H10K 50/121* (2023.02); *H10K 50/15* (2023.02); *H10K 50/16* (2023.02); *H10K 50/17* (2023.02); *H10K 50/171* (2023.02); *H10K 50/18* (2023.02); *H10K 71/00* (2023.02); *H10K 71/164* (2023.02); *H10K 2101/30* (2023.02); *H10K 2101/40* (2023.02); *H10K 2102/351* (2023.02)

(58) Field of Classification Search
CPC ................................................. H10K 85/6572
See application file for complete search history.

(56) References Cited

U.S. PATENT DOCUMENTS

| | | | |
|---|---|---|---|
| 9,997,723 B2 * | 6/2018 | Kang | ................. C07D 491/048 |
| 2010/0181553 A1 | 7/2010 | Miyazaki et al. | |
| 2011/0057173 A1 | 3/2011 | LeCloux et al. | |
| 2016/0013413 A1 | 1/2016 | Herron et al. | |
| 2017/0279056 A1 | 9/2017 | Kim et al. | |
| 2018/0102486 A1 | 4/2018 | Lee et al. | |
| 2018/0123051 A1 | 5/2018 | Lee et al. | |
| 2018/0186910 A1 | 7/2018 | Figueroa et al. | |
| 2018/0233676 A1 | 8/2018 | Kang et al. | |
| 2019/0131537 A1 | 5/2019 | Kim et al. | |
| 2019/0135730 A1 | 5/2019 | Mun et al. | |
| 2019/0296244 A1 | 9/2019 | Mun et al. | |

FOREIGN PATENT DOCUMENTS

| | | |
|---|---|---|
| CN | 104447505 A | 3/2015 |
| CN | 106414428 A | 2/2017 |
| CN | 106604911 A | 4/2017 |
| CN | 107531718 A | 1/2018 |
| CN | 107922311 A | 4/2018 |

(Continued)

OTHER PUBLICATIONS

Tong "Enhancement of OLED Efficiencies and High-Voltage Stabilities of Light-Emitting Materials by Deuteration." Journal of Physical Chemistry C, 2007, 111(8), 3490-3494.*
English Translation of Office Action dated Mar. 11, 2011 from corresponding JP Application No. 2020-026670.
English Translation of Office Action dated Mar. 19, 2021 from CN Application No. 202010102592.3.
English Translation of Office Action dated Mar. 19, 2021 from CN Application No. 2020101025707.
English Translation of Office Action dated Mar. 11, 2021 from corresponding JP Application No. 2020-026669.

(Continued)

*Primary Examiner* — David K O'Dell
(74) *Attorney, Agent, or Firm* — Elmore Patent Law Group, P.C.; Carolyn Elmore; Joseph Zucchero

(57) ABSTRACT

The present invention relates to the field of display technologies, and particularly to a fused polycyclic compound, a preparation method and use thereof. The fused polycyclic compound provided in the present invention has a structure of General Formula IV. The structure of the compound has ambipolarity, and the HOMO level and the LUMO level of the host material are respectively located on different electron donating group and electron withdrawing group, such that the transport of charges and holes in the host material becomes more balanced, thereby expanding the area where holes and electrons are recombined in the light emitting layer, reducing the exciton concentration, preventing the triplet-triplet annihilation of the device, and improving the efficiency of the device.

12 Claims, 2 Drawing Sheets

(56) References Cited

FOREIGN PATENT DOCUMENTS

| | | | |
|---|---|---|---|
| CN | 108884102 A | 11/2018 | |
| JP | 2012513688 A | 6/2012 | |
| JP | 2015103617 A | 6/2015 | |
| JP | 2016178326 A | 10/2016 | |
| JP | 2017518974 A | 7/2017 | |
| JP | 2017527992 A | 9/2017 | |
| JP | 2018524442 A | 8/2018 | |
| JP | 2019007961 A | 1/2019 | |
| KR | 20110034103 A | 4/2011 | |
| KR | 20170112865 A | 10/2017 | |
| KR | 20180015546 A | 2/2018 | |
| KR | 10-2019-0075322 A | 7/2019 | |
| WO | 2008029670 A1 | 3/2008 | |
| WO | 2011037429 A3 | 10/2011 | |
| WO | WO-2012036482 A1 * | 3/2012 | ........... C07D 403/04 |
| WO | 2017204556 A1 | 11/2017 | |
| WO | 2018026197 A1 | 2/2018 | |
| WO | 2020032424 A1 | 2/2020 | |
| WO | 2020032428 A1 | 2/2020 | |
| WO | 2020032447 A1 | 2/2020 | |

OTHER PUBLICATIONS

English Translation of the first Office Action dated Aug. 30, 2021 from Korean Application No. 1020200020247.
English Translation of an Office Action dated Aug. 30, 2021 from Korean Application No. 1020200020251.
English Translation of the second Office Action dated Jul. 20, 2021 from Japanese Application No. 2020026669.
English Translation of the third Office Action dated Jun. 29, 2021 from Chinese Application No. 2020101025923.
English Translation of the Decision of Refusal Office Action dated Sep. 7, 2021 from Japanese Application No. 2020026670.
English Translation of Notice of Termination of Reconsideration by Examiners before Appeal Proceedings in Japanese Application No. 2020-26670, dated Feb. 10, 2022.
English Translation of Decision of Rejection dated Mar. 30, 2022 from corresponding JP Application No. 10-2020-0020247.
English Translation of Decision of Rejection dated Mar. 30, 2022 from corresponding JP Application No. 10-2020-0020251.
Office Action dated Oct. 26, 2020 from CN Application No. 2020101025707.
English Translation of Office Action dated Oct. 26, 2020 from CN Application No. 2020101025707.
Office Action dated Nov. 19, 2020 from CN Application No. 2020101025923.
English Translation of Office Action dated Nov. 19, 2020 from CN Application No. 2020101025923.

* cited by examiner

FUSED POLYCYCLIC COMPOUND, AND PREPARATION METHOD AND USE THEREOF

RELATED APPLICATION

This application claims priority under 35 U.S.C. § 119(b) to Chinese Application No. 201910353474.7 filed on Apr. 29, 2019. The entire teachings of the above application are incorporated herein by reference.

BACKGROUND

Technical Field

The present invention relates to the field of display technologies, and particularly to a fused polycyclic compound, and a preparation method and use thereof.

Related Art

Organic light-emitting diodes (OLEDs) are a new display technology that has more promising application prospects than liquid crystal display technology, due to their fast response time, low energy consumption, self-lighting, wide color gamut, ultra-thin thickness, foldability and flexibility, thus receiving more and more attention.

In 1987, the first organic light-emitting diode (OLED) device was initially fabricated by Deng Qingyun et al. from the Eastman Kodak Laboratory by means of vacuum deposition, which comprises transparent and conductive indium tin Oxide (ITO) as the cathode on which a diamino derivative and tris(8-hydroxyquinoline)aluminum are deposited in sequence, and comprises a magnesium/silver alloy as the anode material. Such a multilayer structure can reduce the driving voltage of the OLED device, and effectively improve the charge injection at the interface between the material molecules and the electrode, thereby improving the device performance and lifetime.

Compared with traditional technologies, the OLED devices have many advantages such as low driving voltage, high luminescence efficiency, high contrast, high color saturation, wide viewing angle, and fast response time. The current OLED device comprises a plurality of a hole injection layer, a hole transport layer, a light-emitting layer, a hole blocking layer, an electron transport layer, and an electron injection layer, and suitable electrodes in combination. The plurality of layers is respectively formed of a hole injection material, a hole transport material, a light emitting material, a hole blocking material, an electron transport material, and an electron injection material. A light-emitting layer of the OLED device that is fabricated by doping is advantageous in the luminescence efficiency of the device. Therefore, the material for the light-emitting layer is often formed by doping a host material with a guest material, and the host material is an important factor affecting the luminescence efficiency and performance of the OLED device. 4,4'-Bis(9H-carbazol-9-yl)biphenyl (CBP) is a widely used host material with good hole transport performance. However, when CBP is used as a host material, it is prone to recrystallization due to its low glass transition temperature, resulting in reduced performance and luminescence efficiency of OLED devices. Moreover, an increase in the molecular weight of the material can increase the glass transition temperature and thermal stability of the material, but reduce the triplet energy level of the material at the same time, affecting the lifetime and luminescence efficiency of the device.

SUMMARY

An object of the present invention is to overcome the defects existing in the prior art that the host material in the light emitting layer has low glass transition temperature, tendency to crystallization, poor thermal stability, and inability to have both good thermal stability and high triplet energy level.

To achieve the above object, the following technical solutions are adopted in the present invention.

A fused polycyclic compound has a structure shown below:

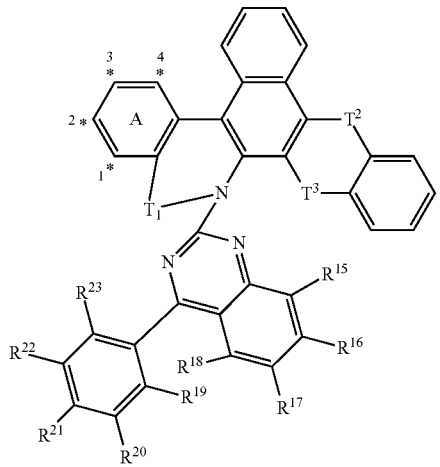

General Formula IV where the phenyl ring A is attached to

at positions 1 and 2, positions 2 and 3, or positions 3 and 4 to form a fused ring sharing the same side, in which "*" and "$\underset{*}{*}$" denotes the points of attachment;

$T^1$ is independently selected from a single bond, $NR^{24}$, S, O, $BR^{24}$, $PR^{24}$, and $C(R^{24})_2$, in which $R^{24}$ is the same or different, and is each independently selected from methyl, deuterated methyl, phenyl, deuterated phenyl, biphenylyl, deuterated biphenylyl, naphthalenyl, and deuterated naphthalenyl;

at least one of $T^2$ and $T^3$ is a single bond, when $T^2$ is a single bond, $T^3$ is S or O, and when $T^3$ is a single bond, $T^2$ is S or O; and $R^{15}$-$R^{23}$ are the same or different, and are each independently selected from hydrogen, deuterium, methyl, deuterated methyl, phenyl, deuterated phenyl, and deuterated methyl substituted phenyl.

In the present invention, when the phenyl ring A is attached to

at positions 3 and 4 to form a fused ring sharing the same side, the General Formula IV has a structure below:

General Formula I

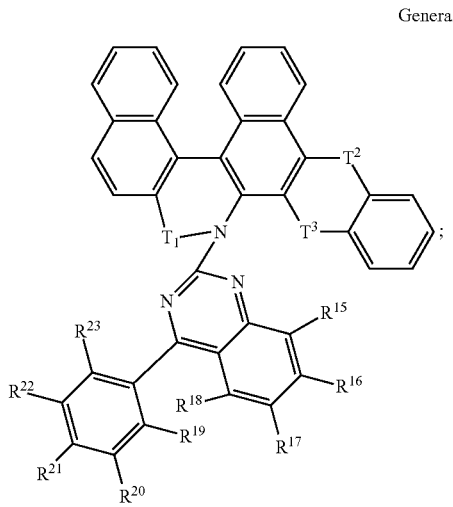

when the phenyl ring A is attached to

at positions 2 and 3 to form a fused ring sharing the same side, the General Formula IV has a structure below:

General Formula III

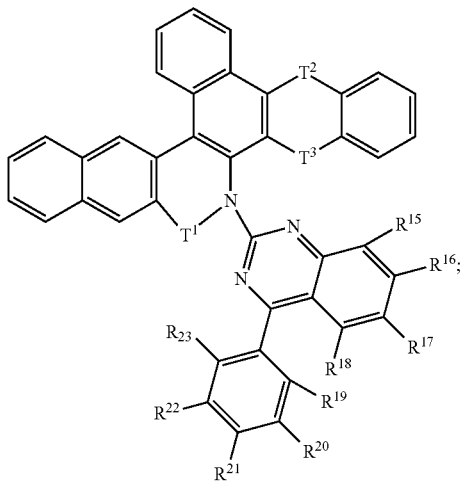

when the phenyl ring A is attached to

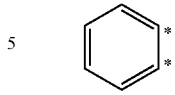

at positions 1 and 2 to form a fused ring sharing the same side, the General Formula IV has a structure below:

General Formula II

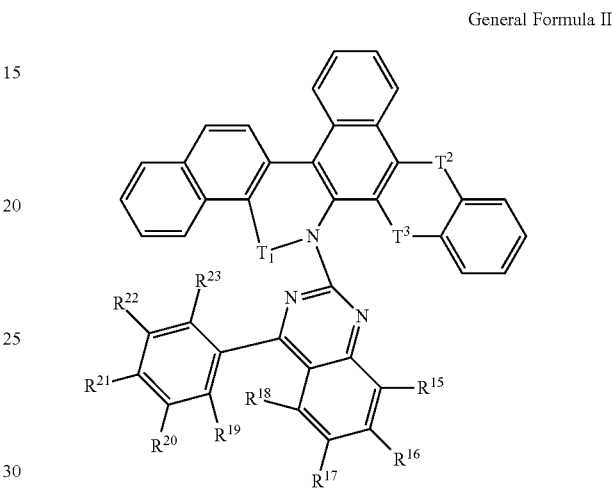

Further, $R^{15}$-$R^{23}$ are the same or different, at least one of which is one selected from deuterium, deuterated methyl, deuterated phenyl, and deuterated methyl substituted phenyl; and preferably, at least one of $R^{19}$, $R^{21}$, and $R^{23}$ is one selected from deuterium, deuterated methyl, deuterated phenyl, and deuterated methyl substituted phenyl.

Further, $R^{15}$-$R^{18}$ are the same or different, and at least one of them is hydrogen; and/or $R^{19}$-$R^{23}$ are the same or different, and at least one of them is hydrogen.

Further, when $T^2$ is a single bond, $T^3$ is S or O.

Further, the compound has a structure shown below:

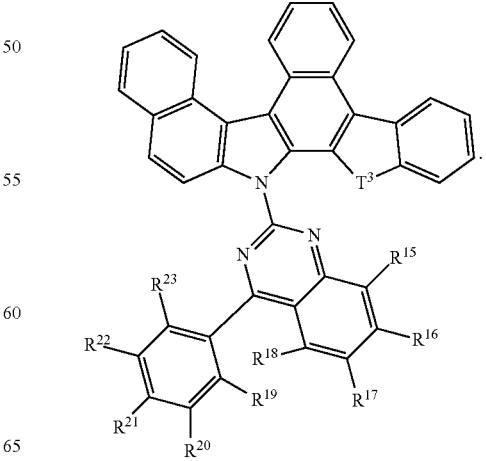

Further, the fused polycyclic compound has any one of the following structures:
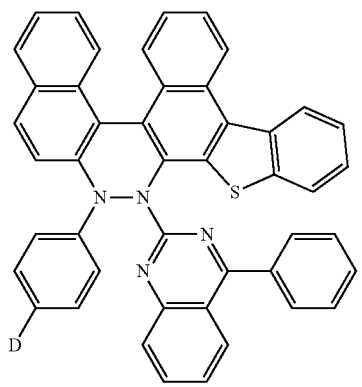
1
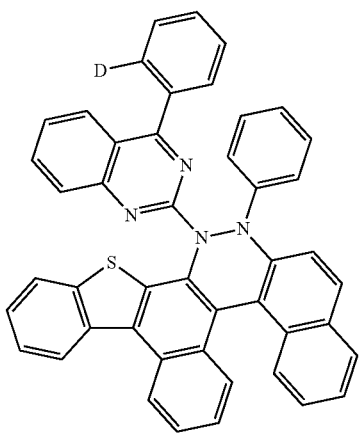
4
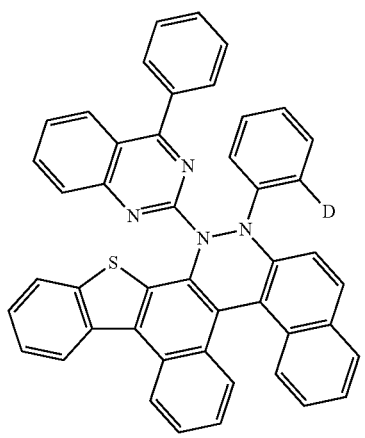
2
-continued
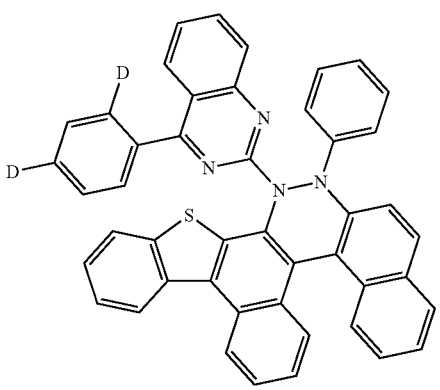
5
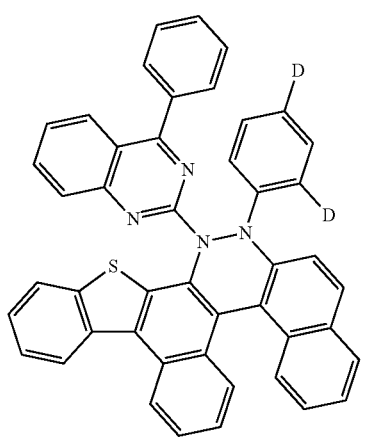
3
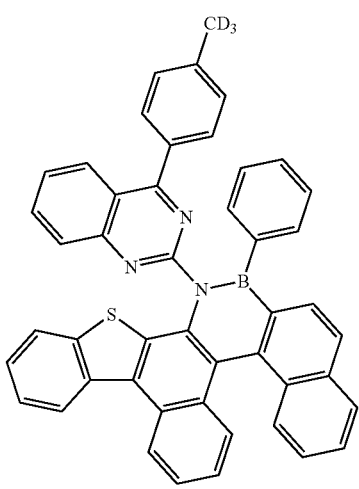
6

7
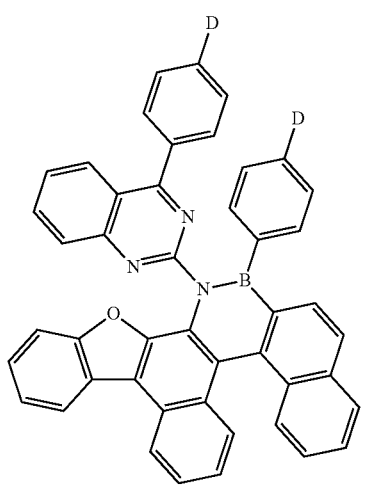
8
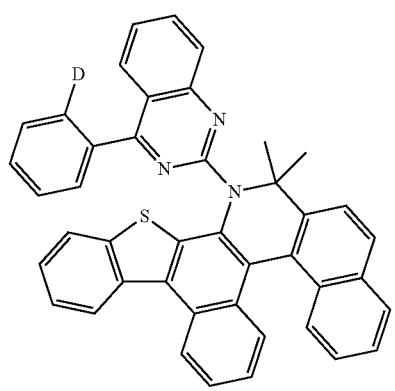
10
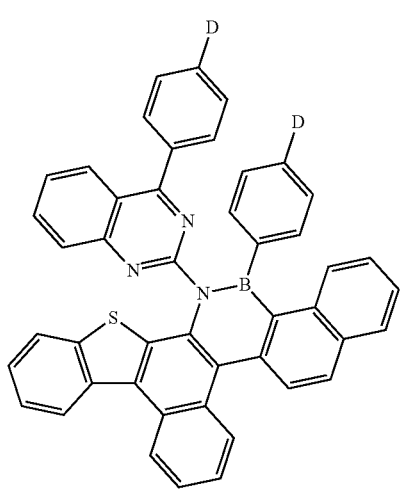
11
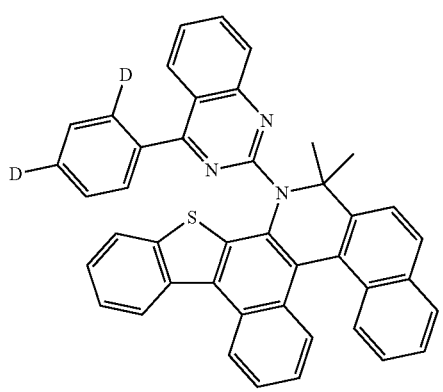
12
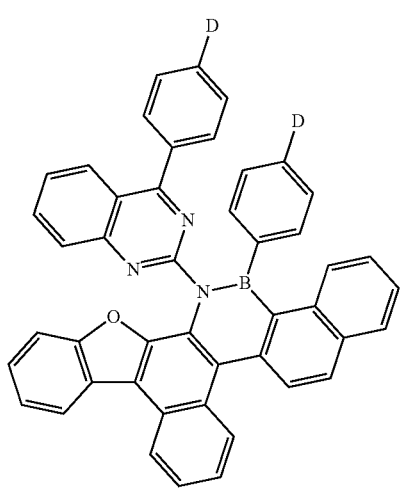
9
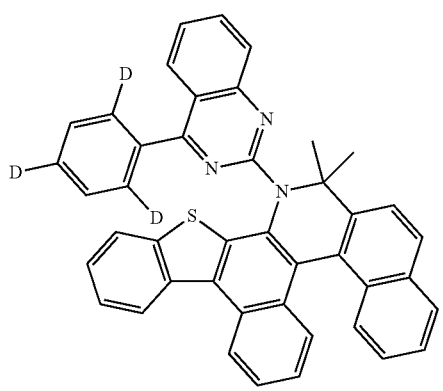
13

14
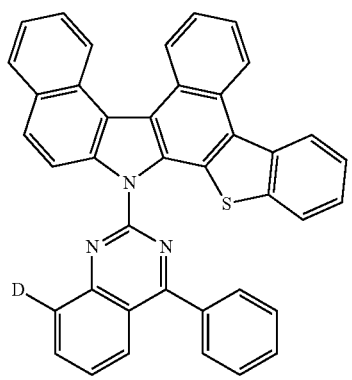
15
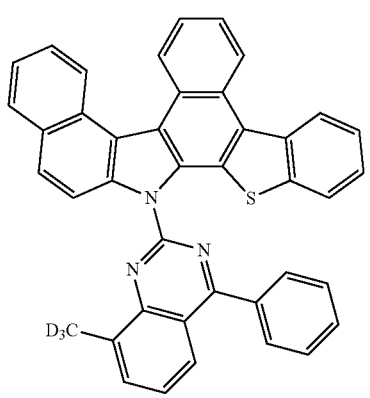
16
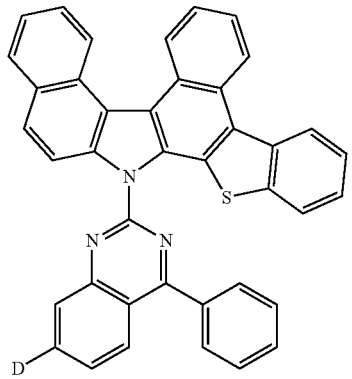
17
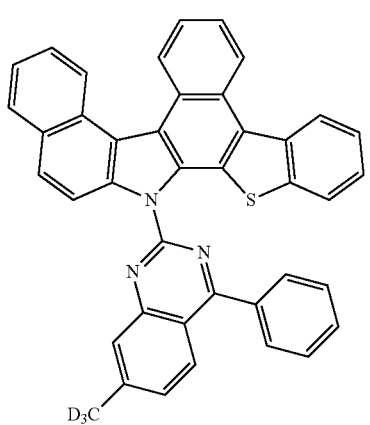
18
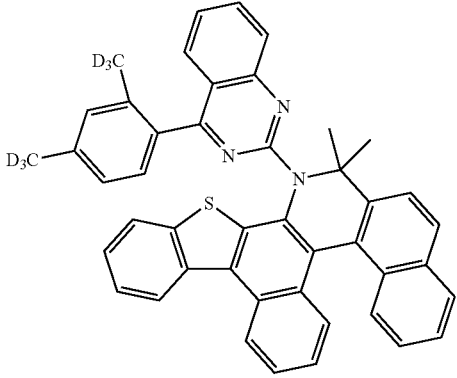
19
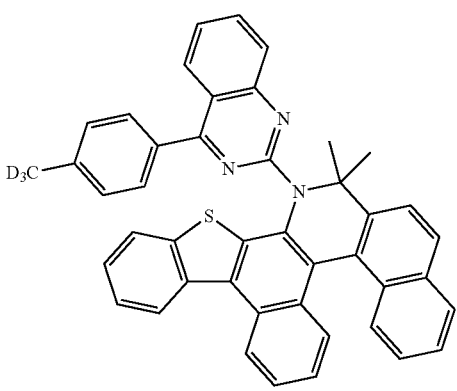
20
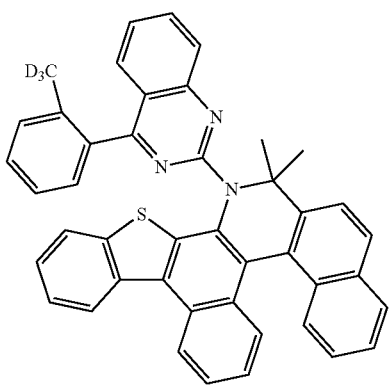
21
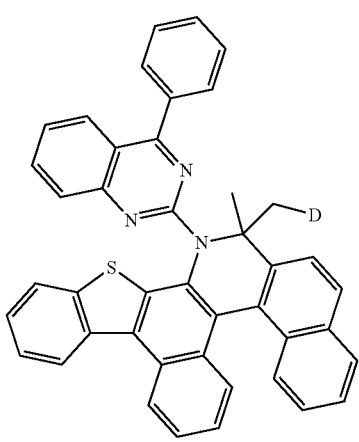

11
-continued
22
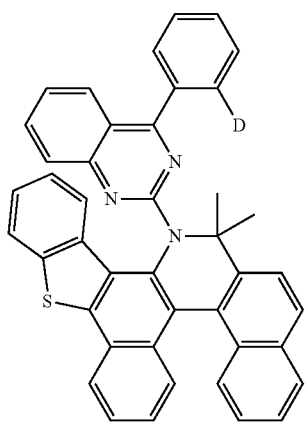
23
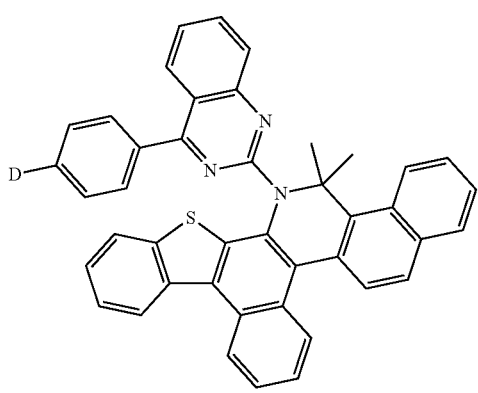
24
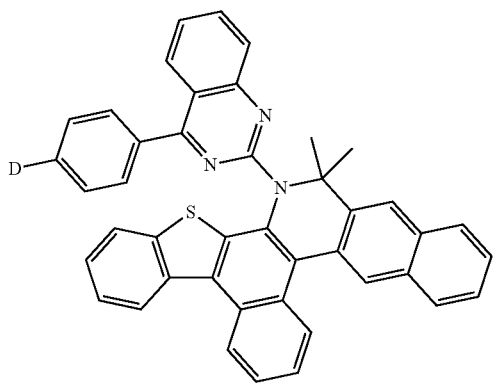
25
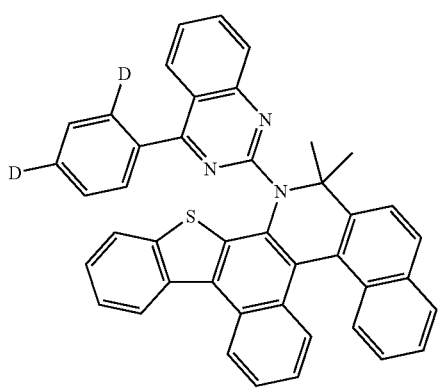
12
-continued
26
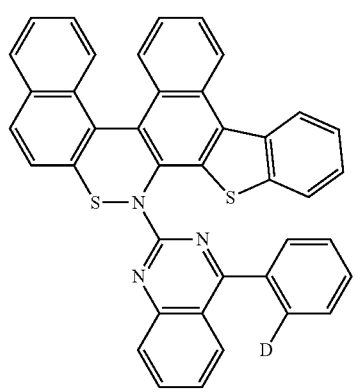
27
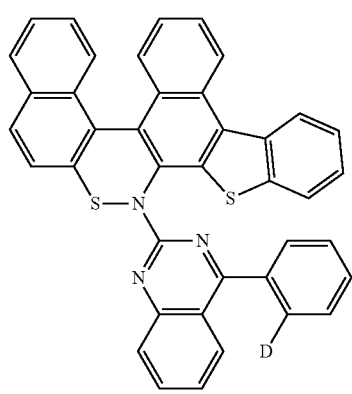
28
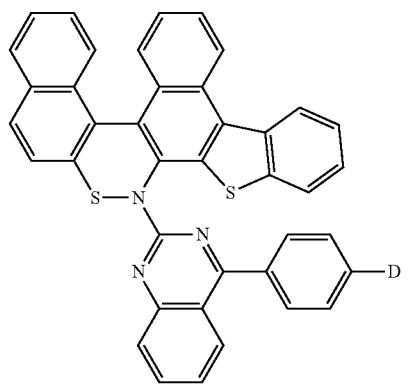
29
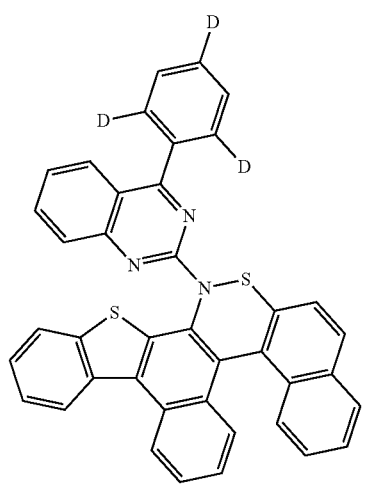

30
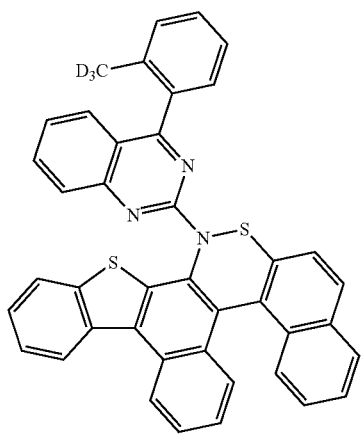
31
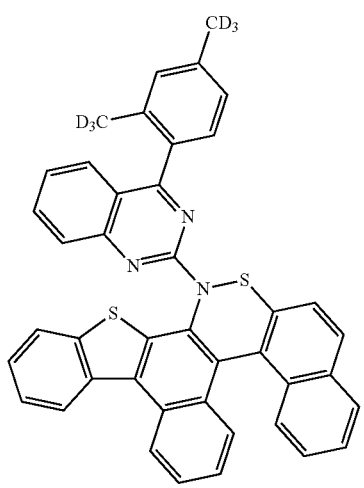
32
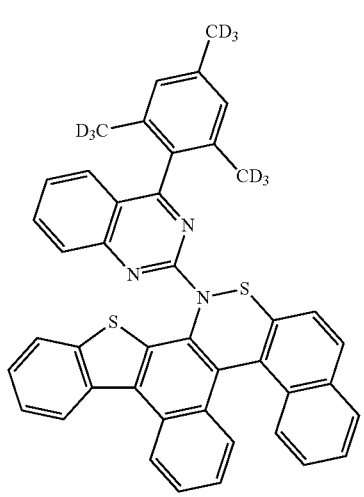
33
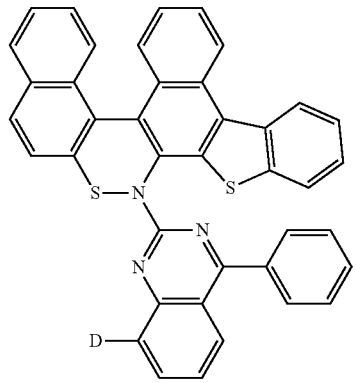
34
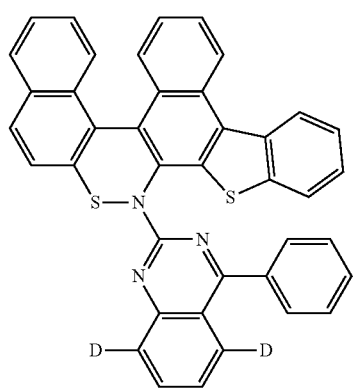
35
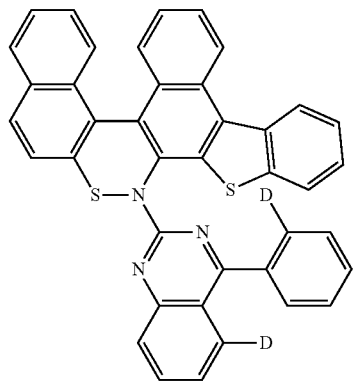
36
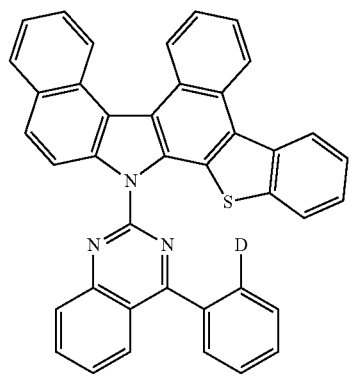

37
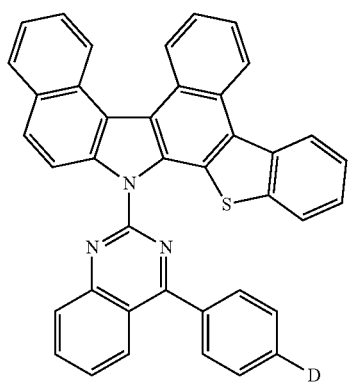
38
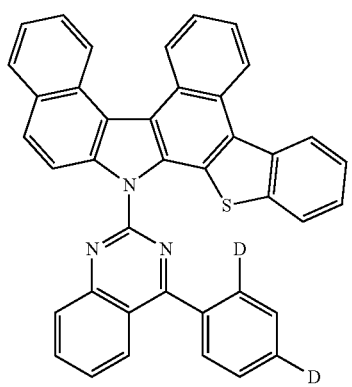
39
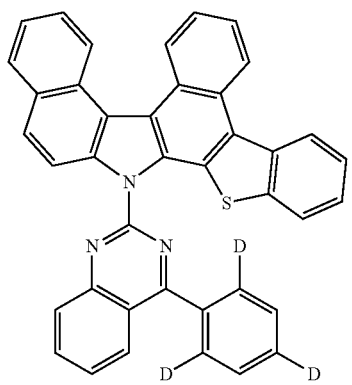
40
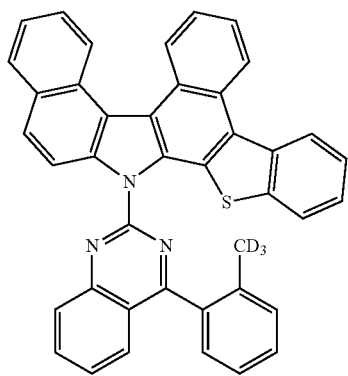
41
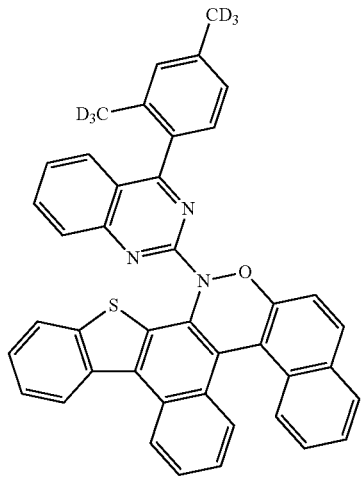
42
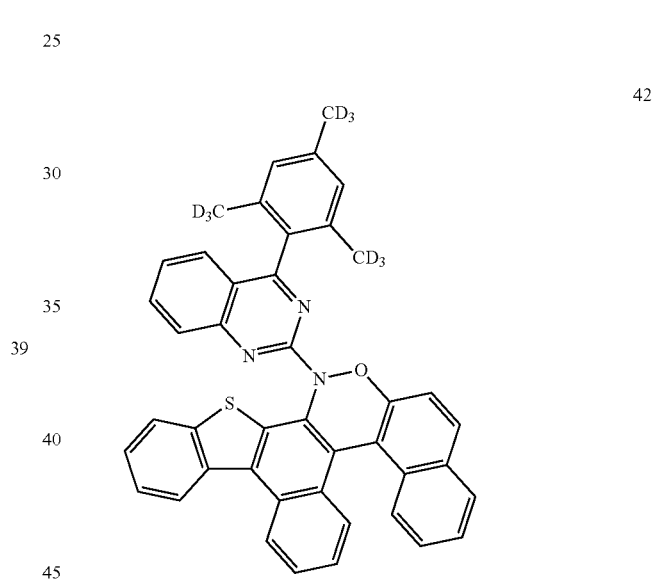
43
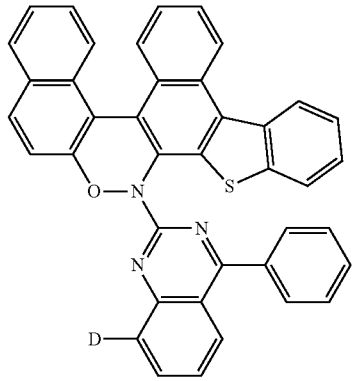

44
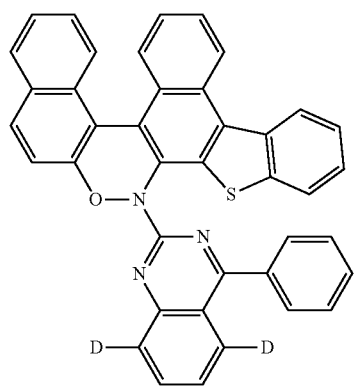
45
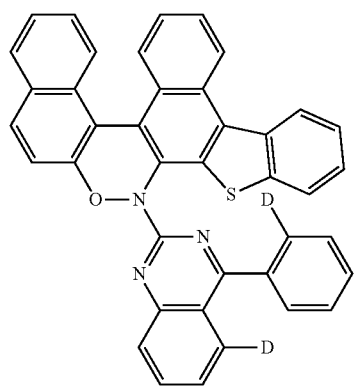
46
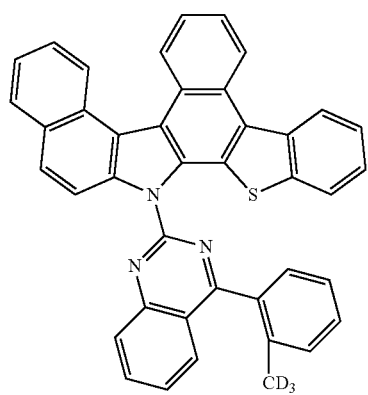
47
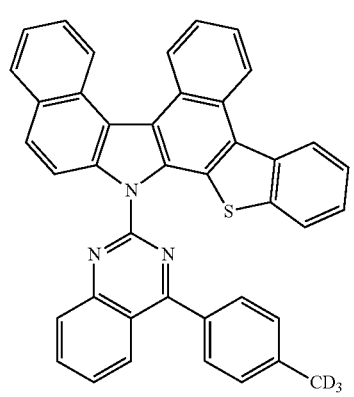
48
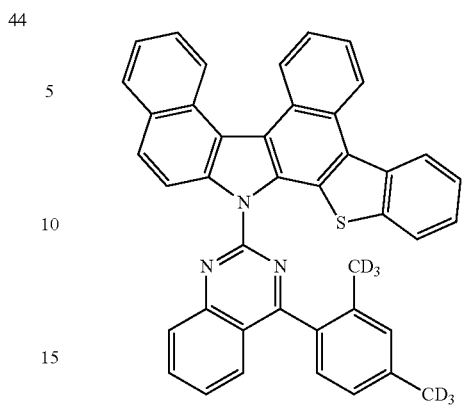
49
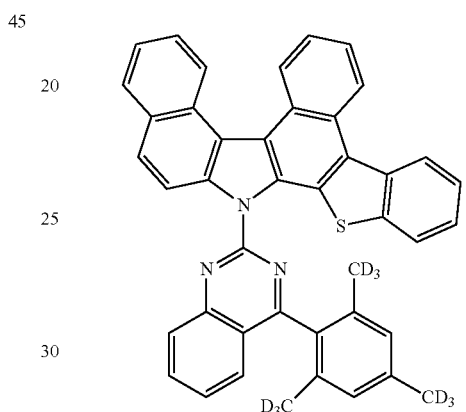
50
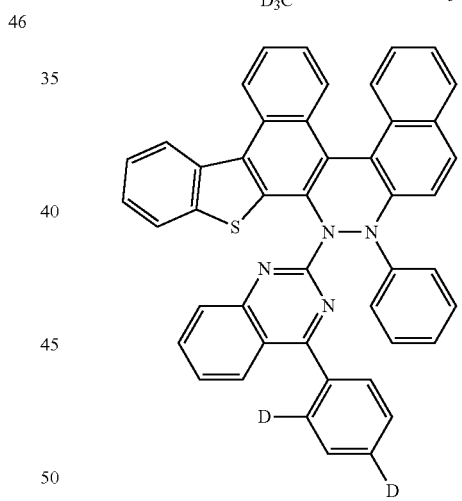
51
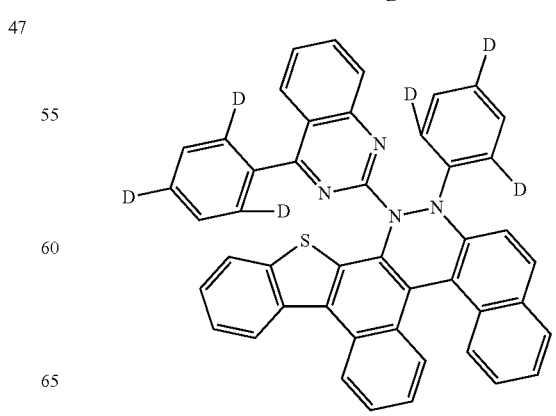

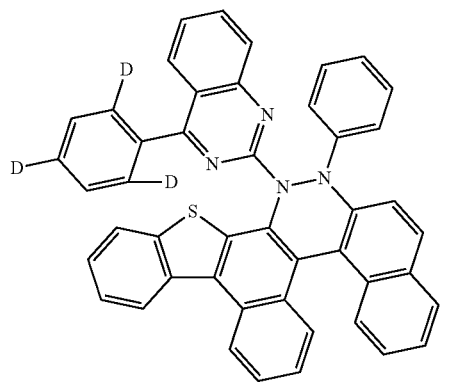
52
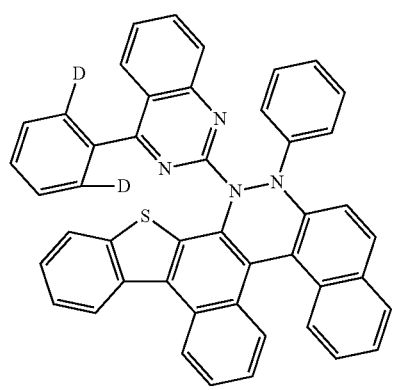
53
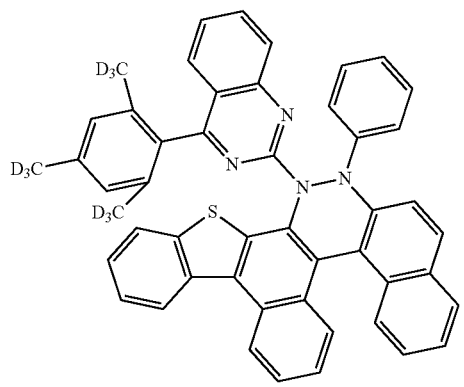
54
55
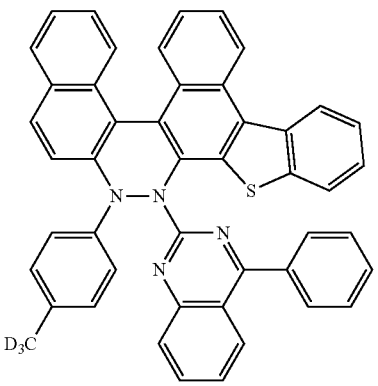
56
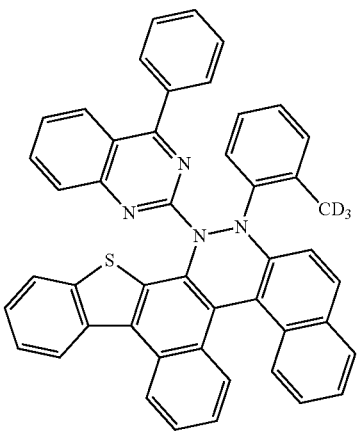
57
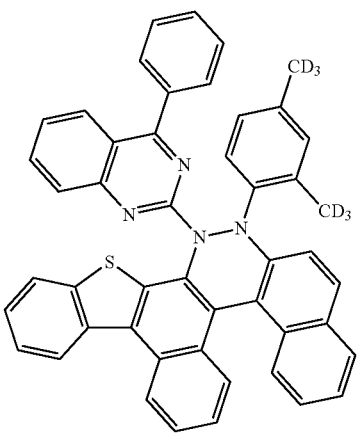
58

59
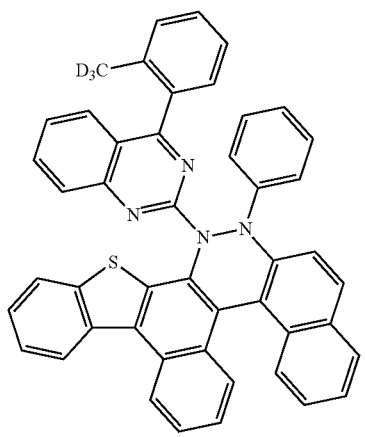
60
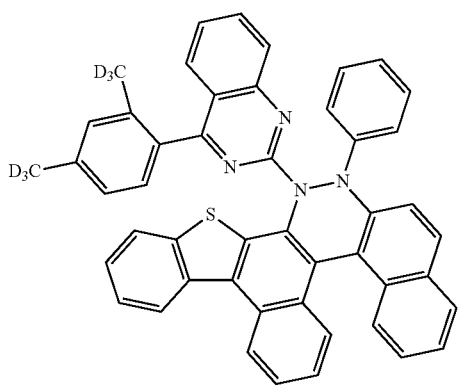
61
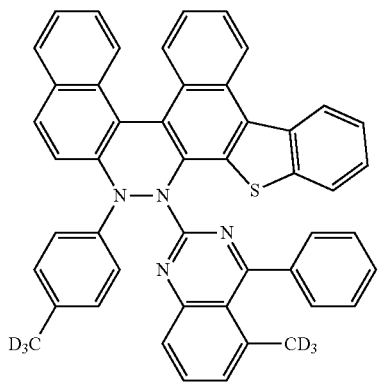
62
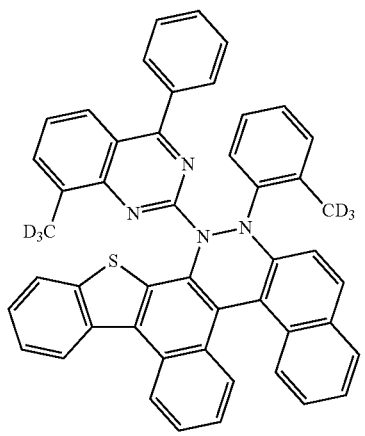
63
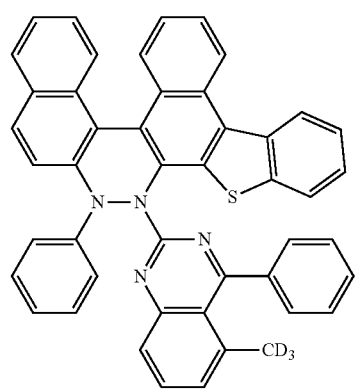
64
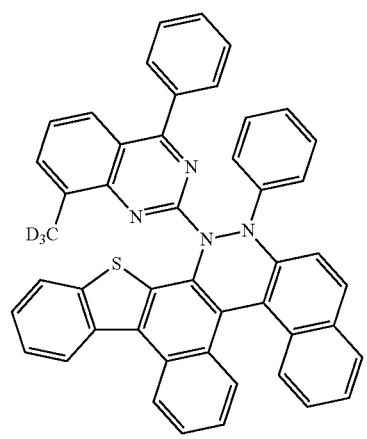
65
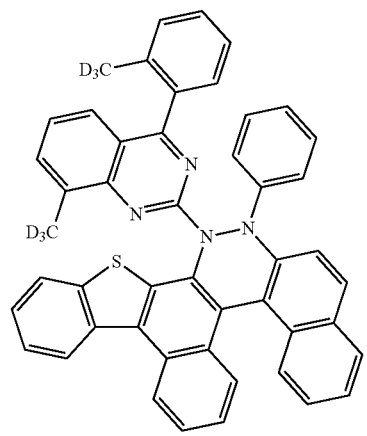

66
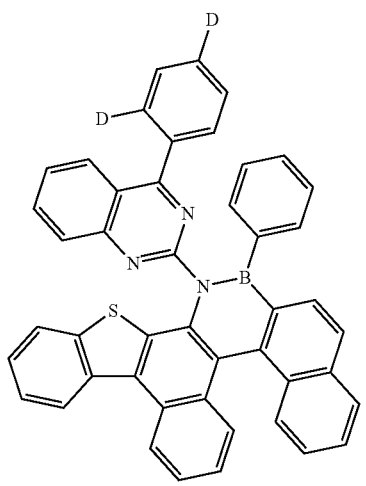
67
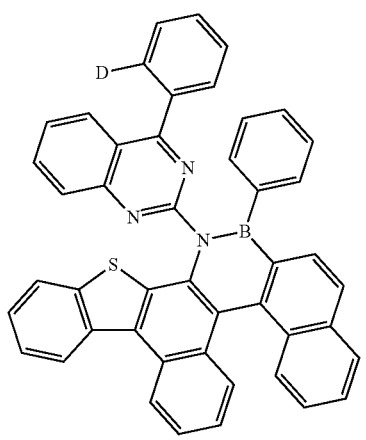
68
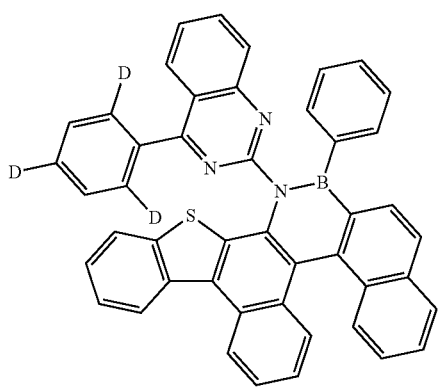
69
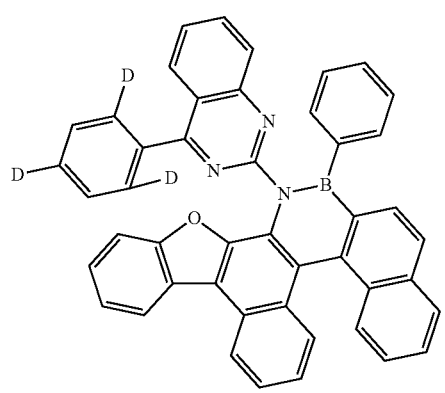
70
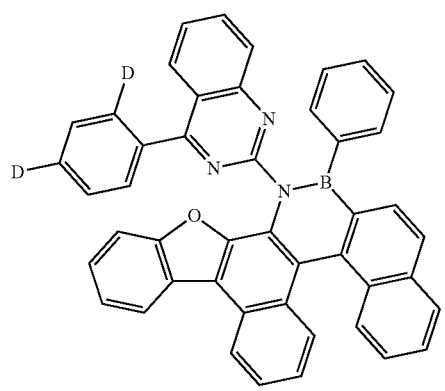
71
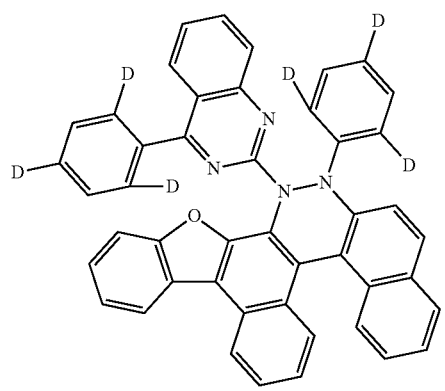
72
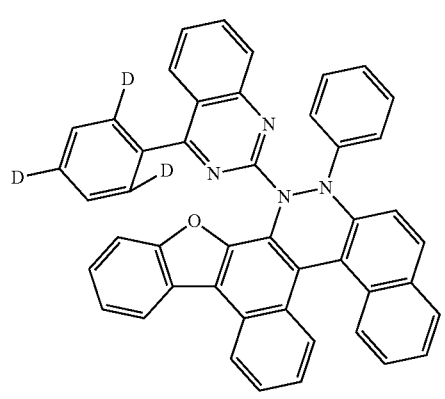

73
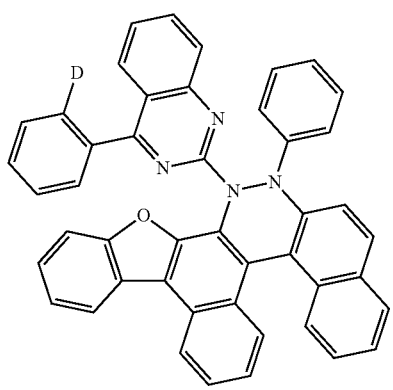
74
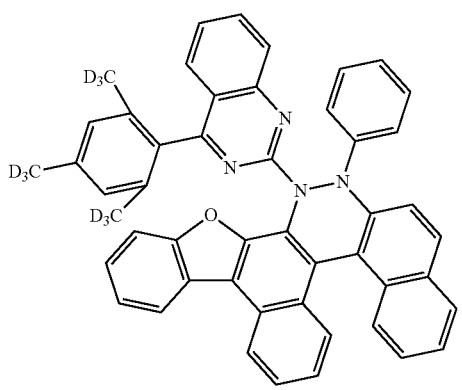
75
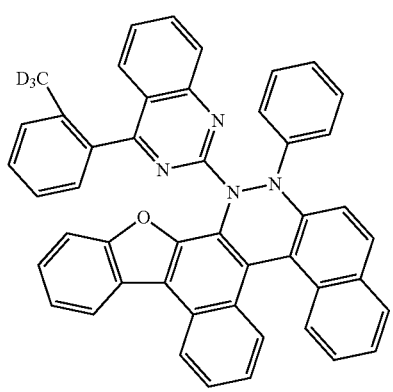
76
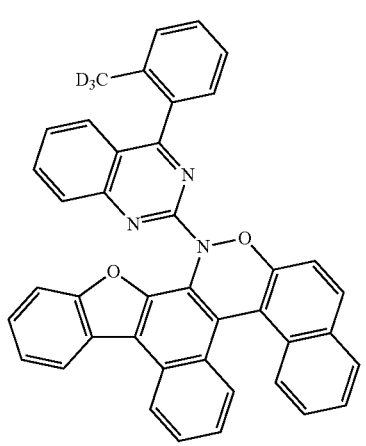
77
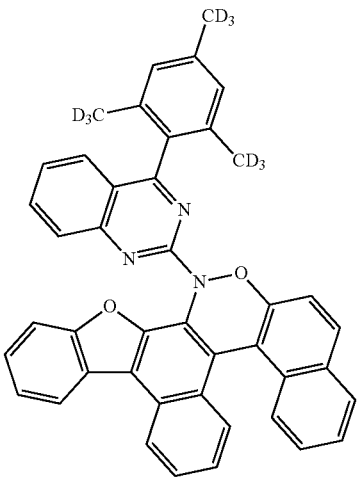
78
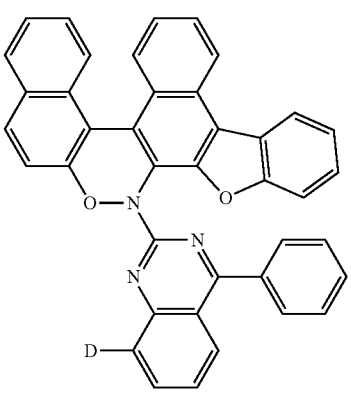
79
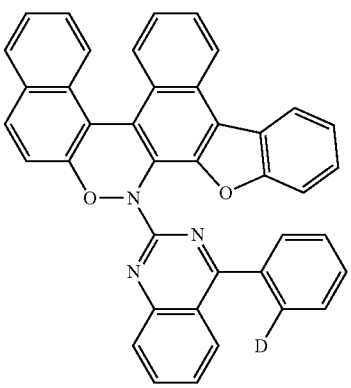
80
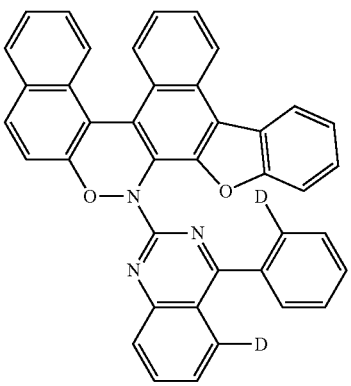

81
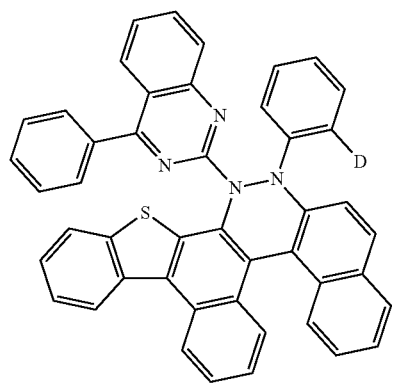
82
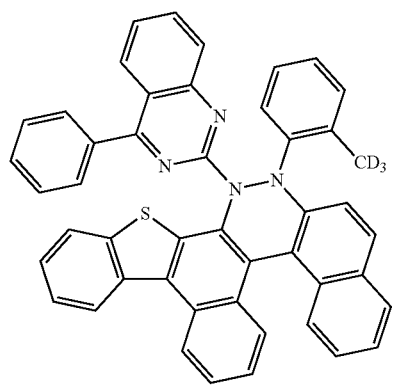
83
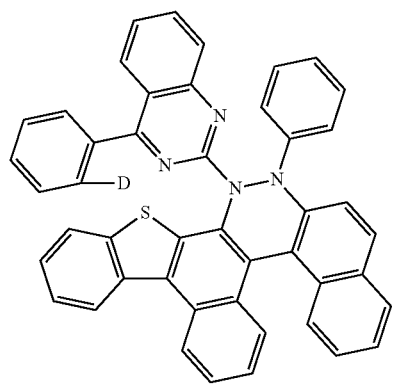
84
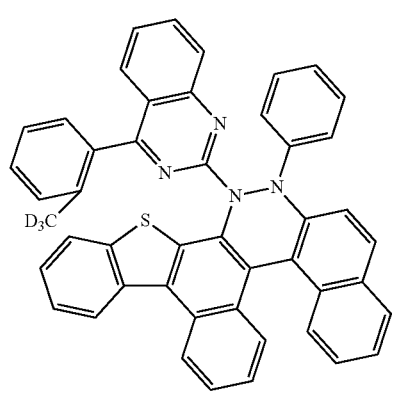
85
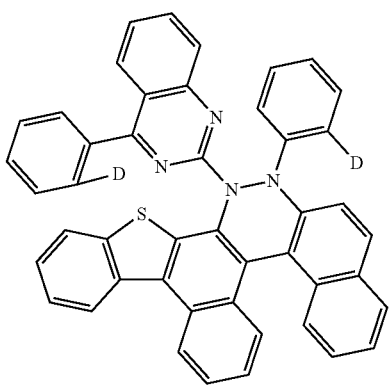
86
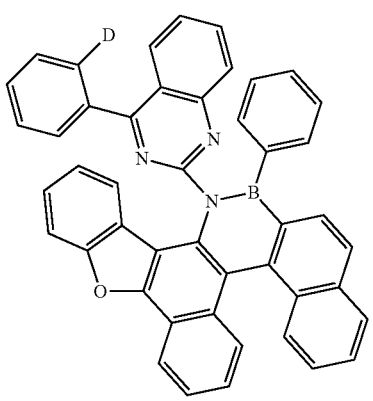
87
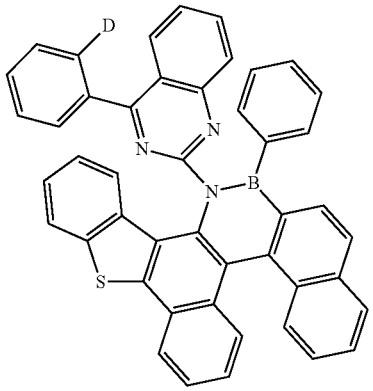
88
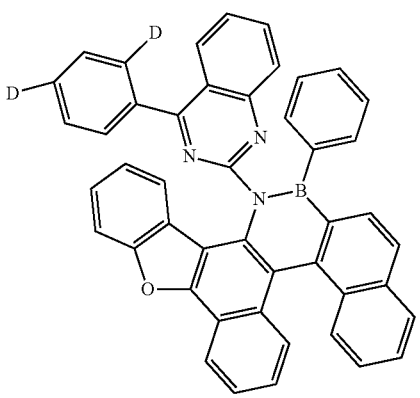

-continued
89
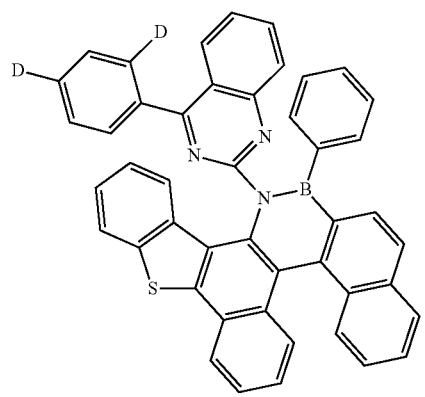
90
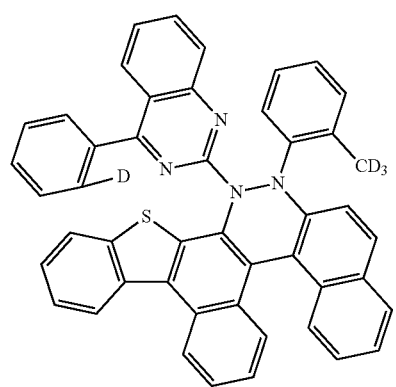
91
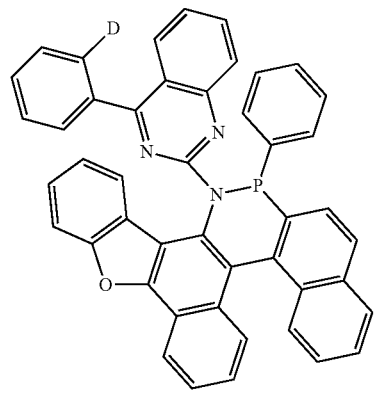
92
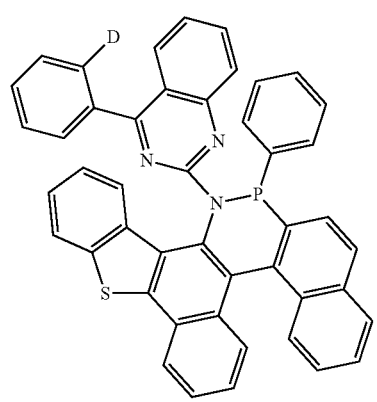
-continued
93
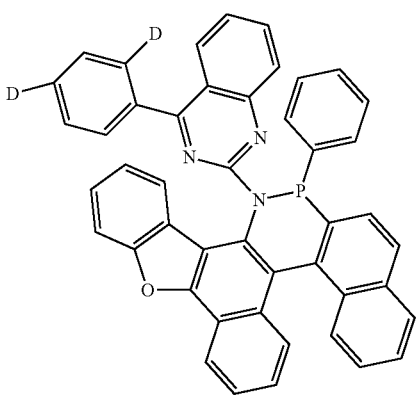
94
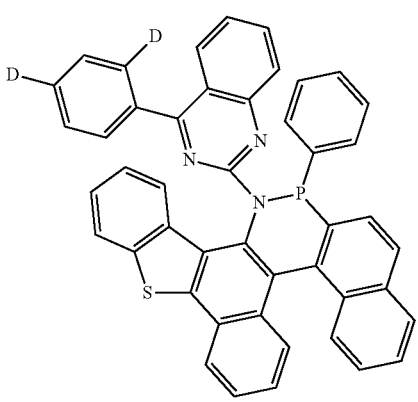
95
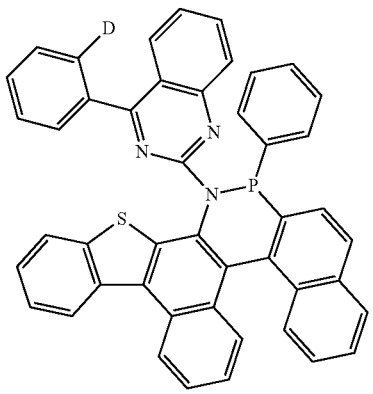
96
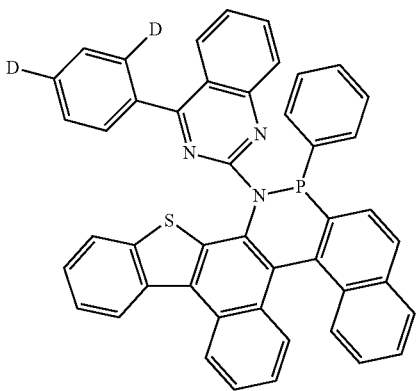

US 11,706,982 B2
31
-continued
97
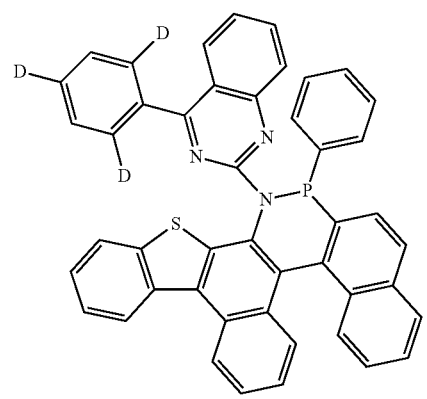
98
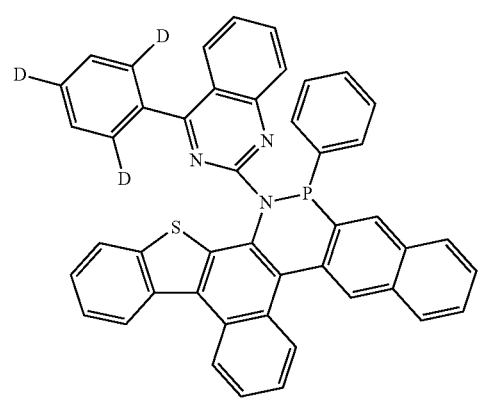
99
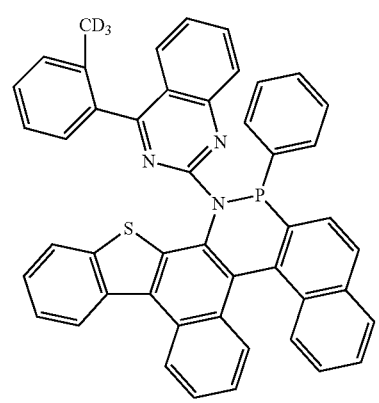
100
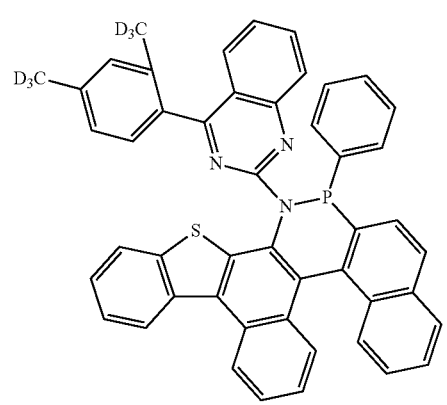
32
-continued
101
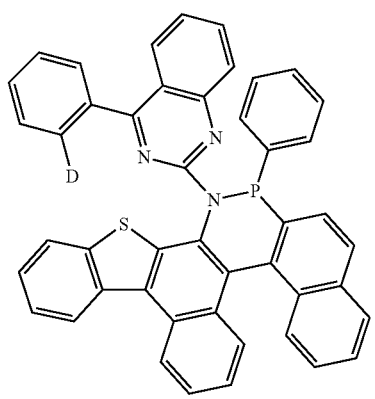
102
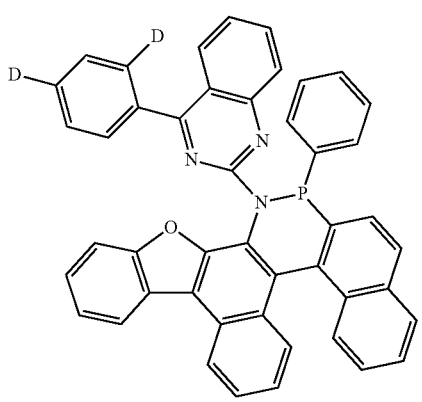
103
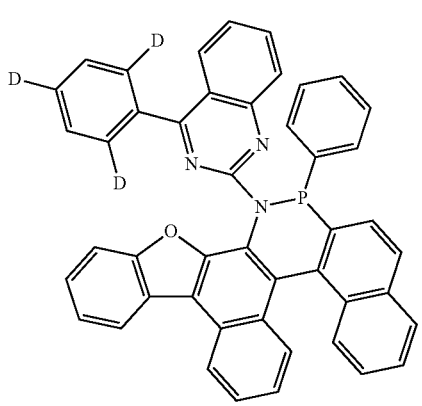
104
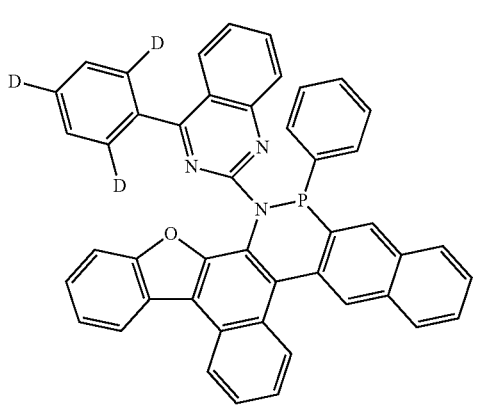

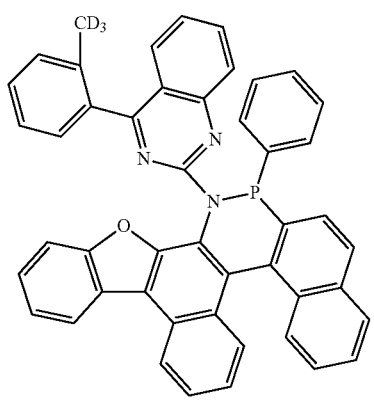
105
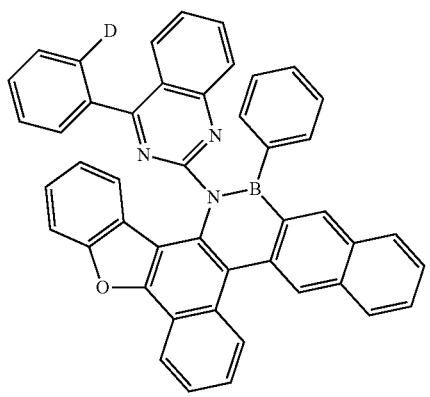
106
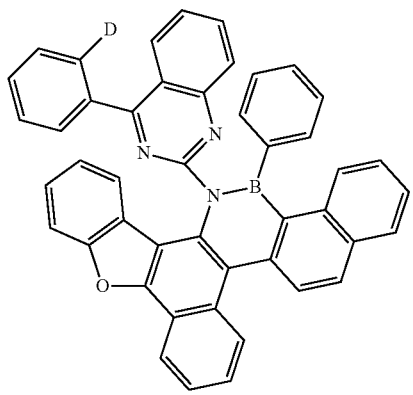
107
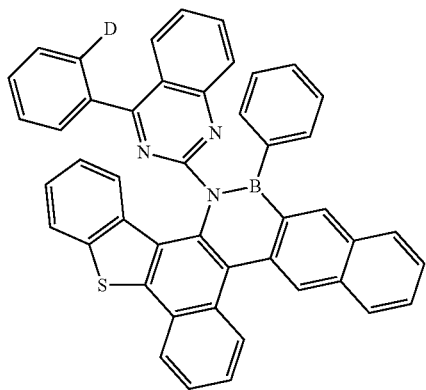
108
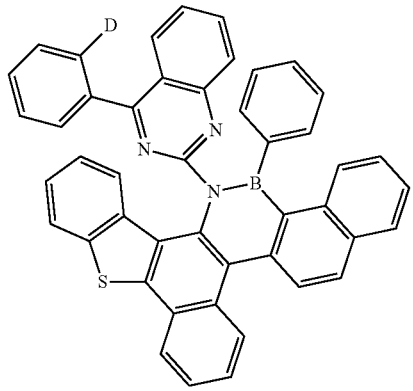
109
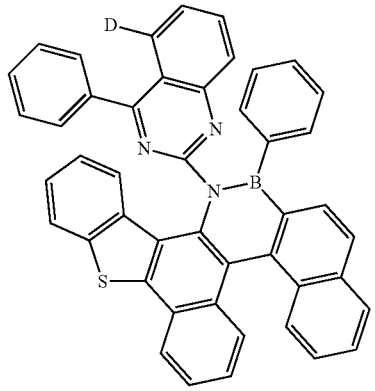
110
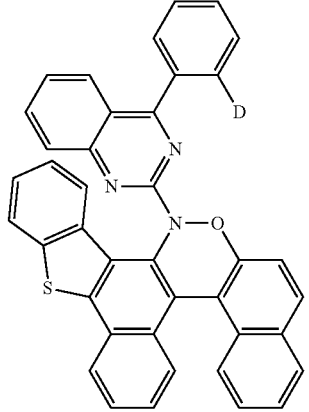
111
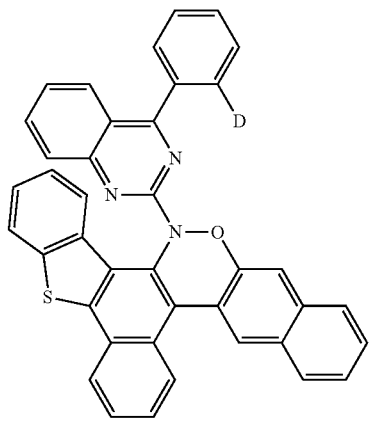
112

113
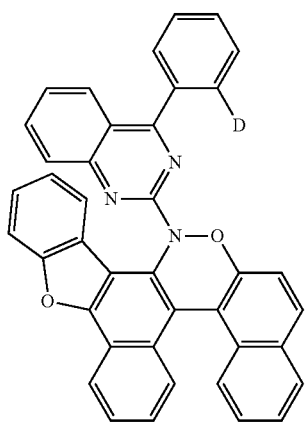
114
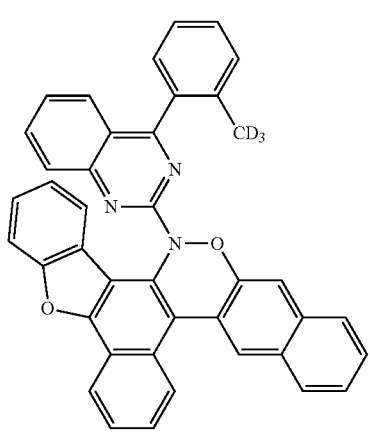
115
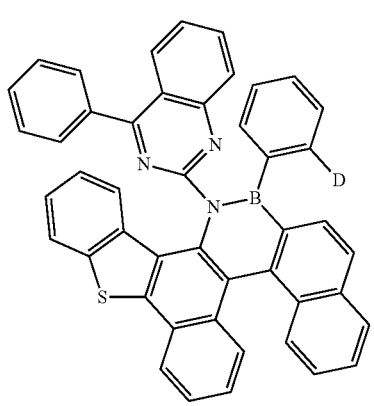
116
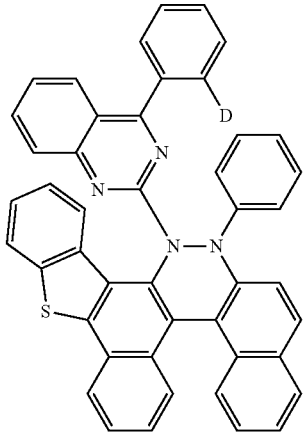
117
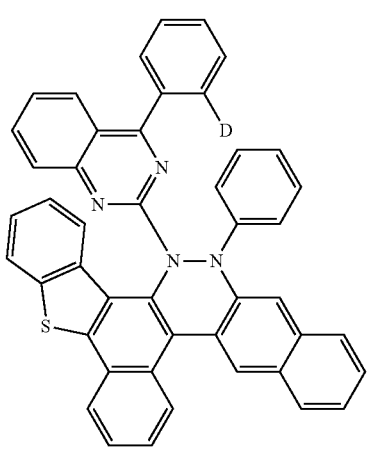

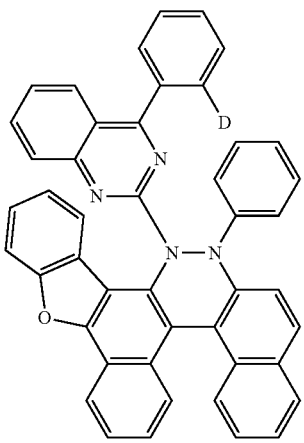

118

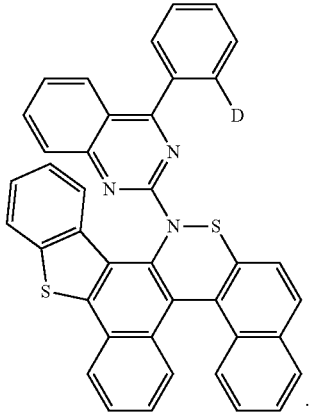

120

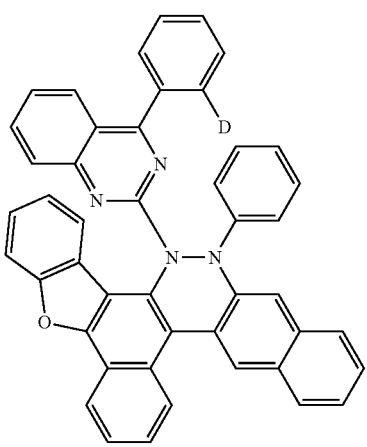

119

The present invention also provides a method for preparing the fused polycyclic compound.

When $T^1$ is selected from $C(R^{24})_2$, that is, the fused polycyclic compound has a structure of General Formula IV-1, and $T^4$ is selected from $ClC(R^{24})_2$ or $BrC(R^{24})_2$, the preparation method comprises:

subjecting the compound of Formula (E) used as a raw material to a cyclization reaction in the presence of a catalyst to obtain an intermediate compound (F); and coupling the intermediate compound (F) to the compound of Formula (G) in the presence of a catalyst, to obtain the compound of General Formula IV-1.

The route for preparing the compound of General Formula IV-1 is shown below:

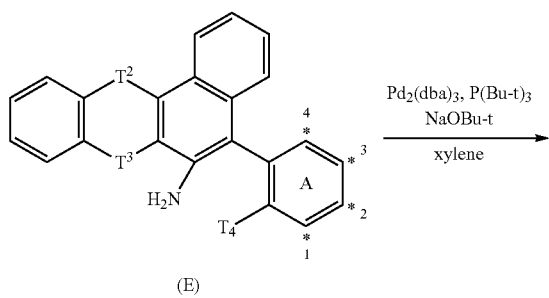

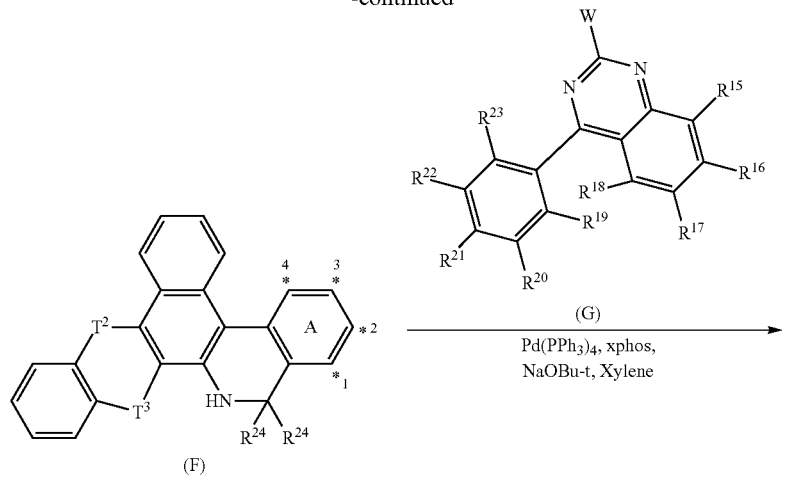

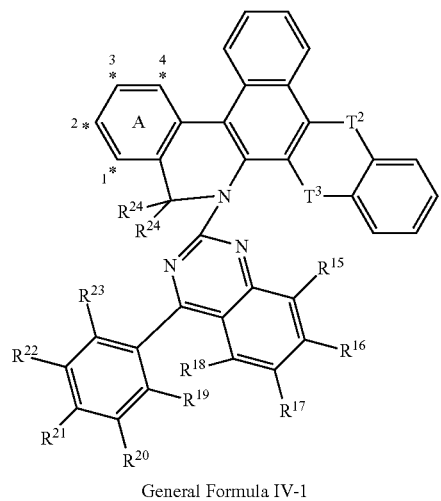

General Formula IV-1

Alternatively, when T¹ is selected from BR²⁴, that is, the fused polycyclic compound has a structure of General Formula IV-2, and T⁴ is selected from hydrogen, the preparation method comprises:

reacting the compound of Formula (E) used as a raw material with the compound of Formula (H) in the presence of a catalyst to obtain an intermediate compound (J); and coupling the intermediate compound (J) to the compound of Formula (G) in the presence of a catalyst, to obtain the compound of General Formula IV-2.

The route for preparing the compound of General Formula IV-2 is shown below:

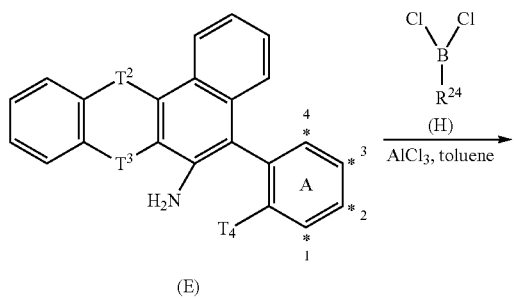

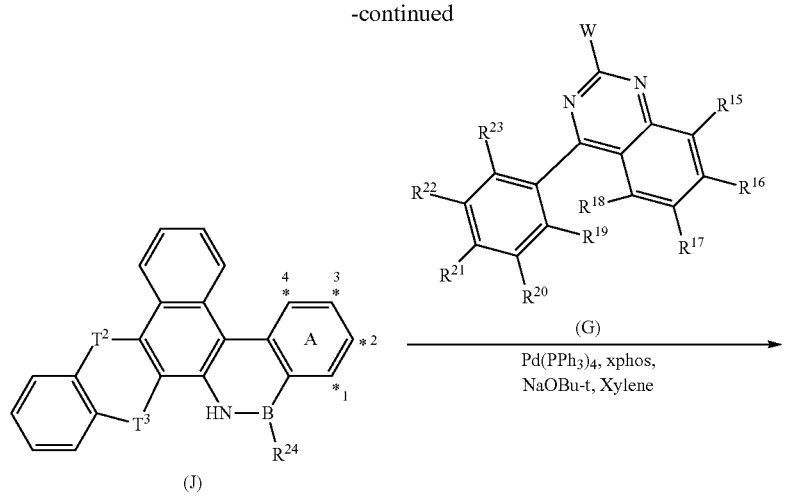

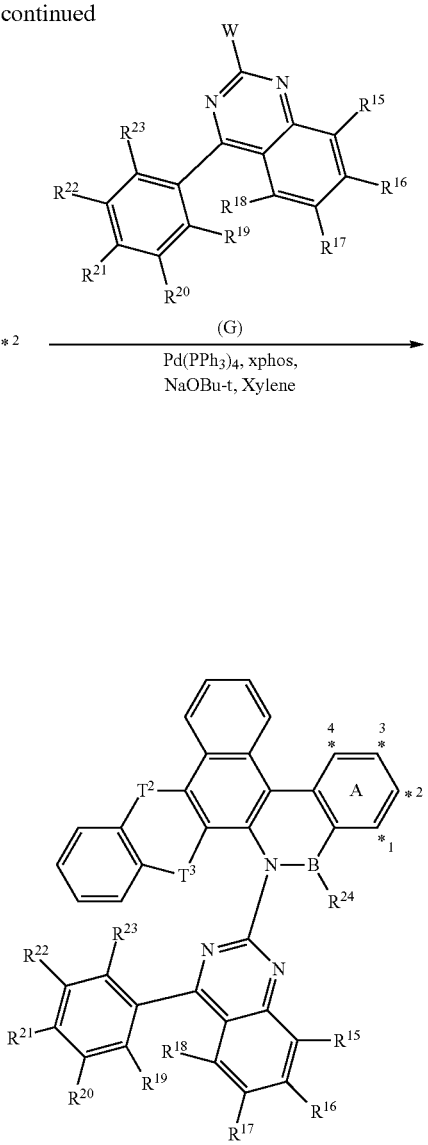

General Formula IV-2

Alternatively, when $T^1$ is selected from S, that is, the fused polycyclic compound has a structure of General Formula IV-3, and $T^4$ is selected from mercapto, the preparation method comprises:

reacting the compound of Formula (E) used as a raw material in the presence of a catalyst to obtain an intermediate compound (K); and coupling the intermediate compound (K) to the compound of Formula (G) in the presence of a catalyst, to obtain the compound of General Formula IV-3.

The route for preparing the compound of General Formula IV-3 is shown below:

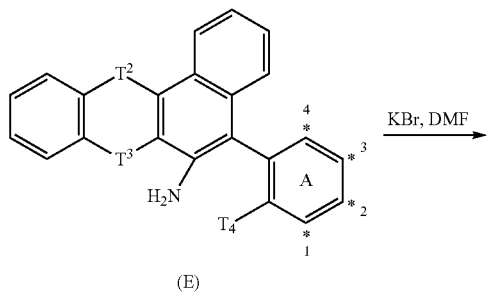

-continued

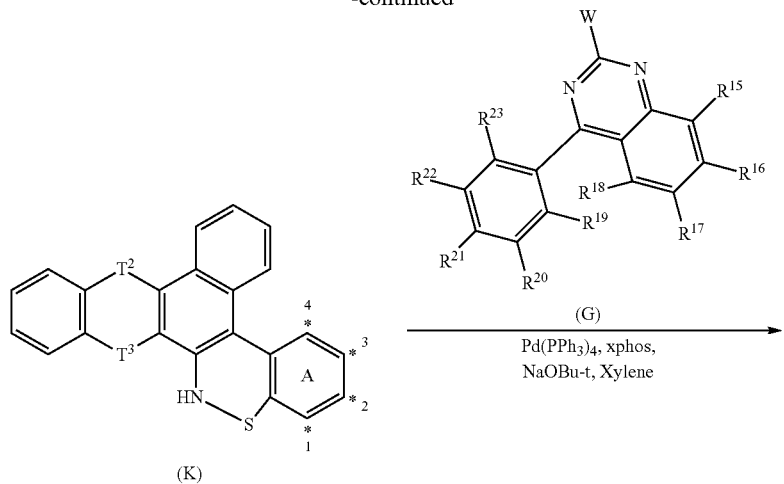

(K) (G)

Pd(PPh₃)₄, xphos, NaOBu-t, Xylene

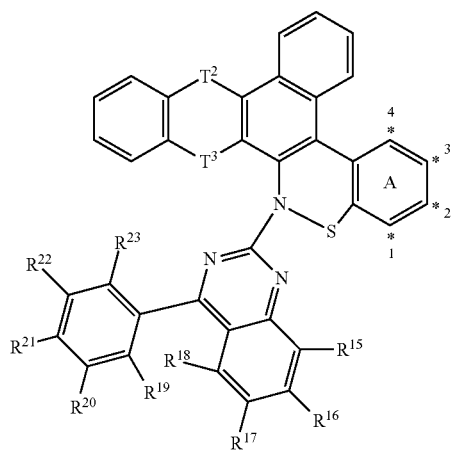

General Formula IV-3

Alternatively, when $T^1$ is selected from O, that is, the fused polycyclic compound has a structure of General Formula IV-4, and $T^4$ is selected from hydroxyl, the preparation method comprises:

reacting the compound of Formula (E) used as a raw material in the presence of a catalyst to obtain an intermediate compound (K-1); and coupling the intermediate compound (K-1) to the compound of Formula (G) in the presence of a catalyst, to obtain the compound of General Formula IV-4.

The route for preparing the compound of General Formula IV-4 is shown below:

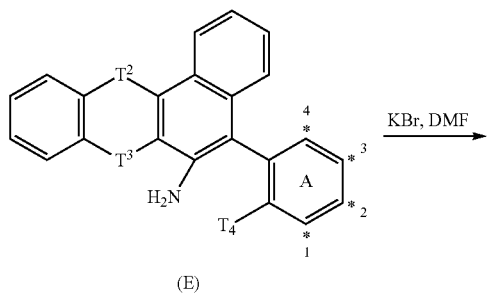

(E)

KBr, DMF

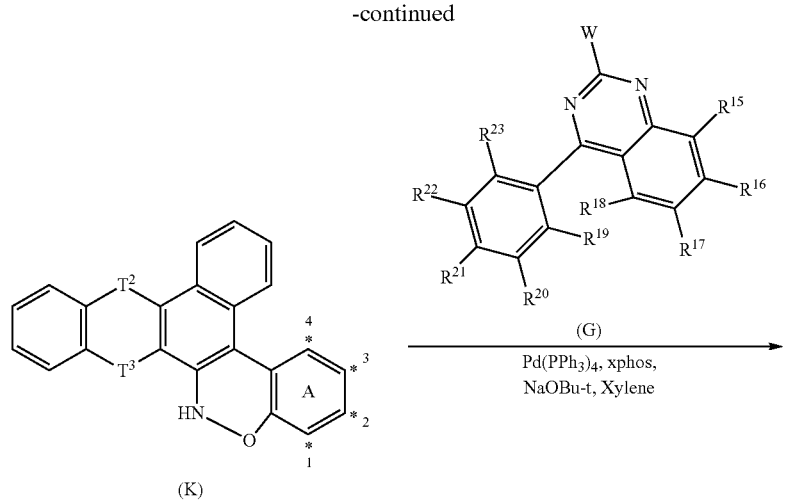

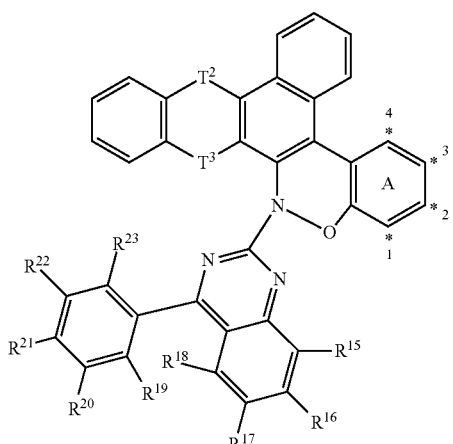

General Formula IV-4

Alternatively, when $T^1$ is selected from $PR^{24}$, that is, the fused polycyclic compound has a structure of General Formula IV-5, and $T^4$ is selected from hydrogen, the preparation method comprises:

reacting the compound of Formula (E) used as a raw material in the presence of a catalyst to obtain an intermediate compound (L); reacting the intermediate compound (L) in the presence of a catalyst to obtain an intermediate compound (M); coupling the intermediate compound (M) to the compound of Formula (N) in the presence of a catalyst to obtain an intermediate compound (O); and coupling the intermediate compound (O) to the compound of Formula (G) in the presence of a catalyst, to obtain the compound of General Formula IV-5.

The route for preparing the compound of General Formula IV-5 is shown below:

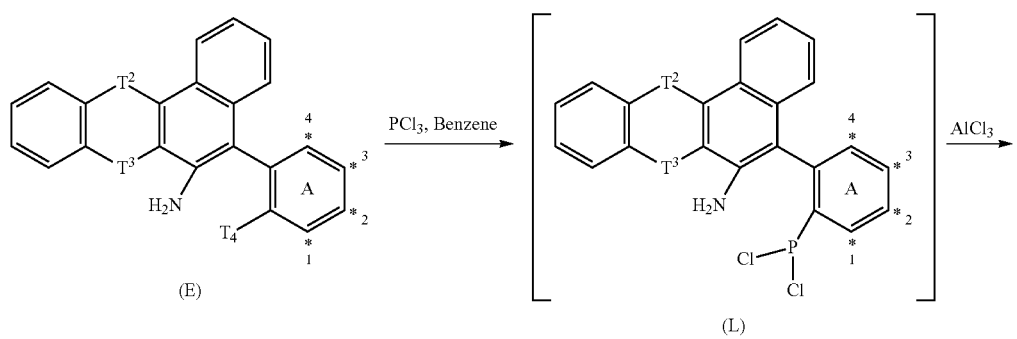

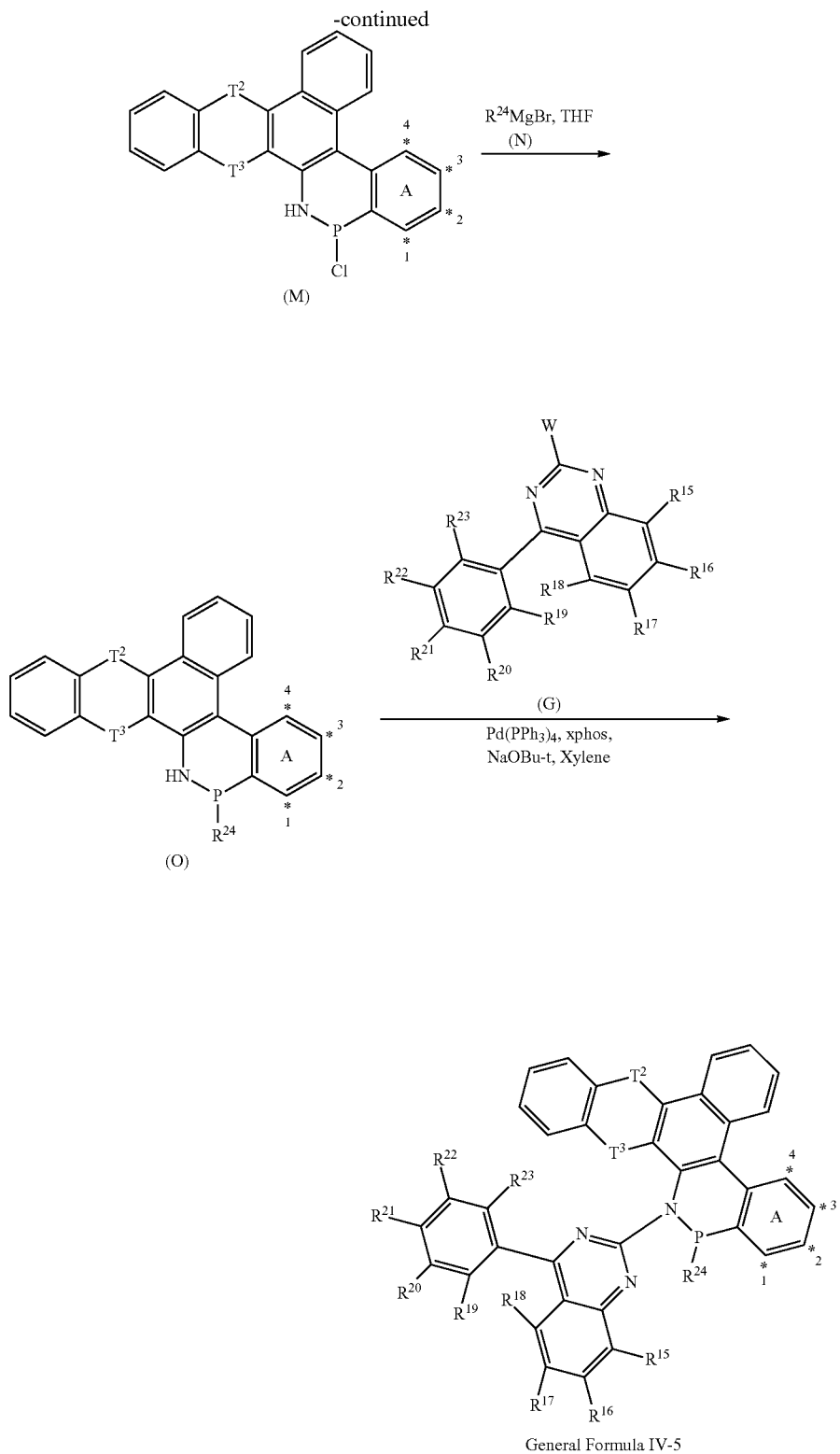

Alternatively, when $T^1$ is selected from $NR^{24}$, that is, the fused polycyclic compound has a structure of General Formula IV-6, and $T^4$ is selected from nitro, the preparation method comprises:

reacting the compound of Formula (D) used as a raw material in the presence of a catalyst to obtain an intermediate compound (P); and reacting the intermediate compound (P) with the compound of Formula (Q) and then the compound of Formula (G), to obtain the compound of General Formula IV-6.

The route for preparing the compound of General Formula IV-6 is shown below:

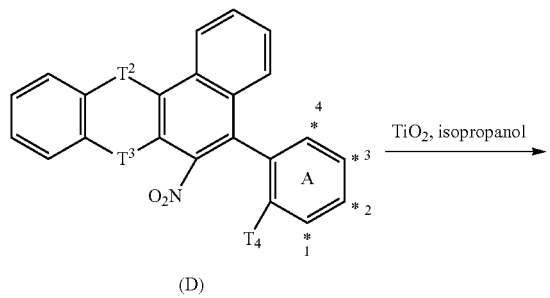

(D)

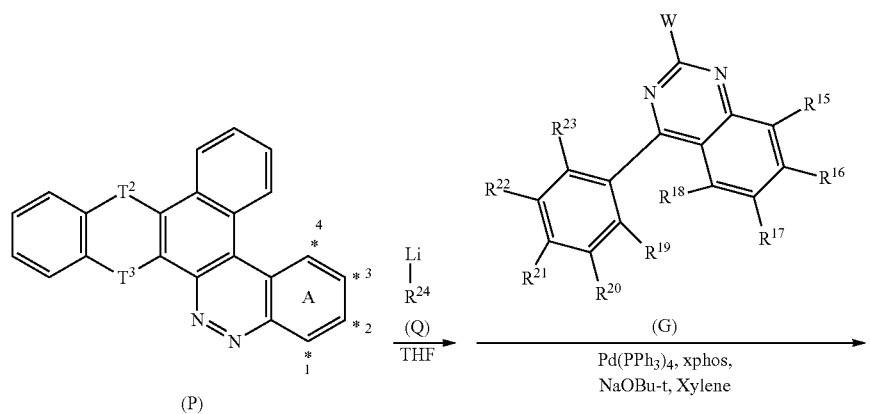

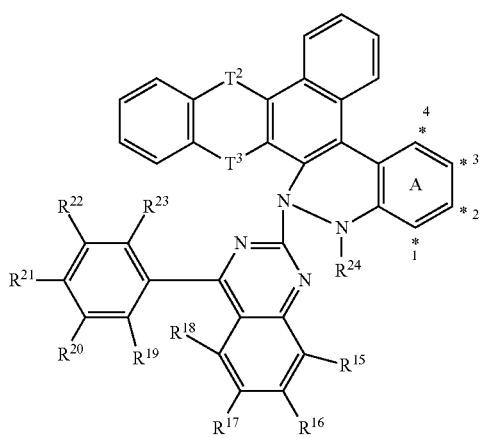

General Formula IV-6

Alternatively, when $T^1$ is selected from a single bond, that is, the fused polycyclic compound has a structure of General Formula IV-7, the preparation method comprises:

reacting the compound of Formula (R) used as a raw material with the compound of Formula (S) in the presence of a catalyst to obtain an intermediate compound (T); subjecting the intermediate compound (T) to a cyclization reaction in the presence of a catalyst to obtain an intermediate compound (U); and coupling the intermediate compound (U) to the compound of Formula (G) in the presence of a catalyst, to obtain the compound of General Formula IV-7.

The route for preparing the compound of General Formula IV-7 is shown below:

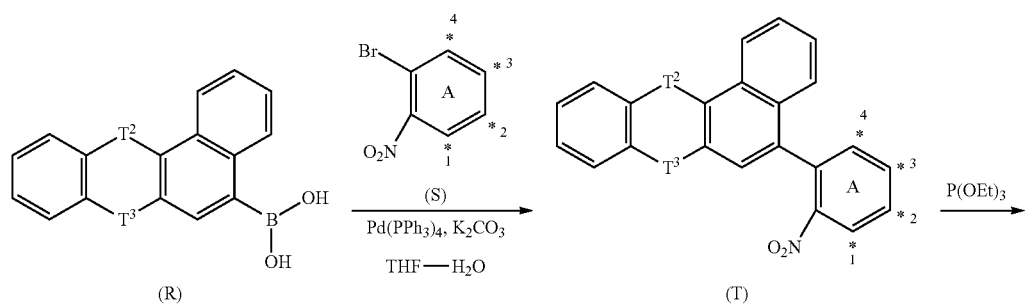

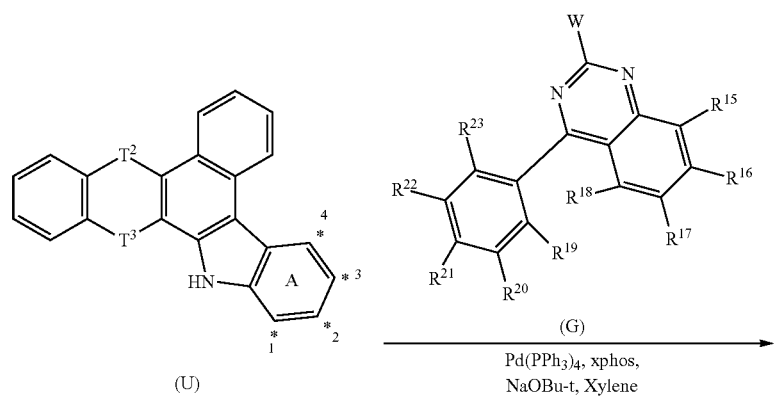

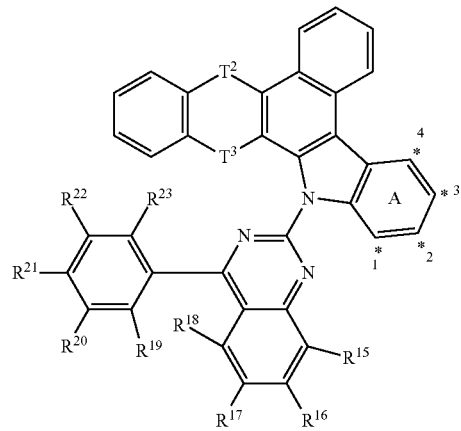

General Formula IV-7 where W is selected from fluoro, chloro, bromo, and iodo.

Further, the compound of Formula (E) is prepared through a method comprising:

nitrifying the compound of Formula (A) used as a starting raw material in the presence of a catalyst to obtain an intermediate compound (B); coupling the intermediate compound (B) to the compound of Formula (C) in the presence of a catalyst to obtain an intermediate compound (D); and reducing the intermediate compound (D) in the presence of a catalyst, to obtain the compound of Formula E.

The route for preparing the compound of Formula E is shown below:

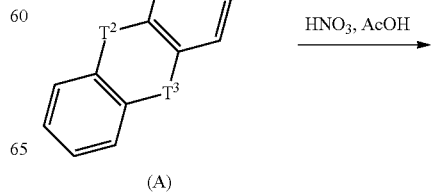

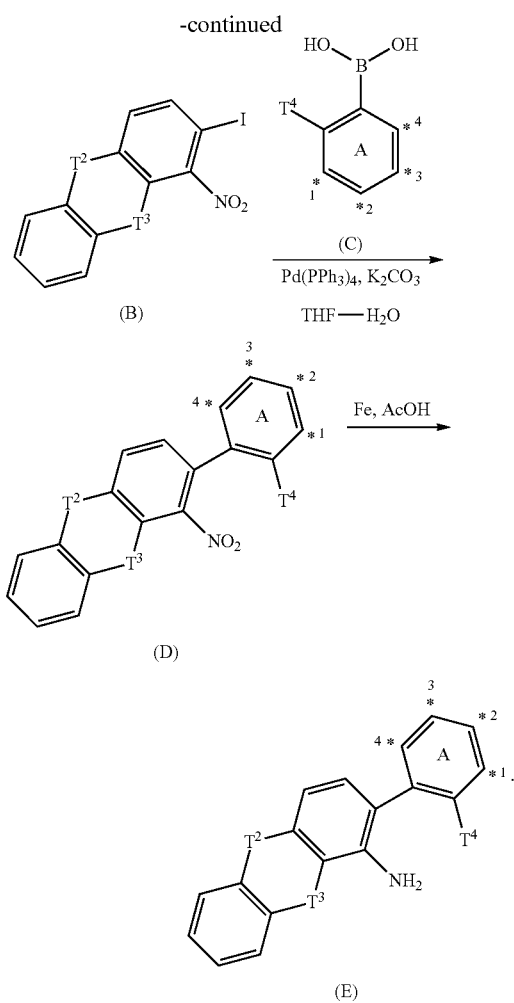

The present invention also provides an electronic device, which comprises any one or a combination of at least two of the fused polycyclic compounds described above.

Preferably, the electronic device is any one of an organic light emitting diode, an organic field effect transistor, an organic thin film transistor, an organic light emitting transistor, an organic integrated circuit, an organic solar cell, an organic field quenching device, a light emitting electrochemical cell, an organic laser diode or an organic photoreceptor.

Further, the electronic device is an organic light emitting device comprising an anode, a cathode, and an organic thin film layer between the anode and the cathode, where the organic thin film layer comprises any one or a combination of at least two of the fused polycyclic compounds described above.

Preferably, the organic thin film layer comprises a light-emitting layer, and also any one or a combination of at least two of a hole injection layer, a hole transport layer, a hole blocking layer, an electron transport layer, an electron injection layer, an electron blocking layer, and a charge transport layer, where the light-emitting layer comprises any one or a combination of at least two of the fused polycyclic compounds described above.

Preferably, the light-emitting layer comprises a host material and a guest material; and the host material in the light-emitting layer comprises any one or a combination of at least two of the fused polycyclic compounds described above.

The present invention further provides a display device comprising the electronic device described above.

The present invention provides a lighting device comprising the electronic device described above.

The present invention has the following beneficial effects.

1) The fused polycyclic compound provided in the present invention has a structure of General Formula IV. The structure of the compound has ambipolarity, the HOMO level and the LUMO level of the host material can be respectively located on different electron donating group and electron withdrawing group, such that the transport of charges and holes in the host material becomes more balanced, thereby expanding the area where holes and electrons are recombined in the light emitting layer, reducing the exciton concentration, preventing the triplet-triplet annihilation of the device, and improving the efficiency of the device.

Meanwhile, in the structure of General Formula IV, by fusing a phenyl ring to the phenyl ring A, the structure of the compound is more highly conjugated, more stable in the excited state, and more rigid, so the stability of the material is higher, which is beneficial to the extension of the lifetime. Moreover, the particular structure of the compound further facilitates the carrier recombination region in the host material of the OLED device to stay far away from the interface of the light emitting layer to the hole or electron transport layer, thus improving the color purity of the OLED device, avoiding the returning of excitons to the transport layer, and further improving the efficiency of the device The HOMO level and the LUMO level of the fused polycyclic compound according to the present invention match those of the adjacent hole transport layer and electron transport layer, so that the OLED device has a small driving voltage. Furthermore, the compound, used as the host material in the light emitting layer of the OLED device, has high triplet energy level and glass transition temperature, and good thermal stability, which ensures the efficient transfer of energy from the host material to the guest material and prevents the crystallization of the material molecules of the light emitting layer.

The compound of the present invention has a small difference between the singlet ($\Delta E_{S1}$) and triplet energy level ($\Delta E_{T1}$), which promotes the reverse intersystem crossing of triplet excitons to singlet excitons. Moreover, the high reverse intersystem crossing (RISC) rate from the triplet state T1 to the singlet state S1 of the hot material can suppress the Dexter energy transfer (DET) from the host material to the luminescent dye, promote the FÖrster energy transfer, and reduce the exciton loss generated during the Dexter energy transfer (DET), thus avoiding the efficiency roll-off of the organic light-emitting device and improving the external quantum efficiency of the device, thereby achieving a high device efficiency.

2) Further, in the fused polycyclic compound provided in the present invention, $R^{15}$-$R^{23}$ are the same or different, at least one of which is one selected from deuterium, deuterated methyl, deuterated phenyl, and deuterated methyl substituted phenyl. By the use of deuterium having lower potential well, lower vibration frequency, smaller amplitude and more stable carbon-deuterium bond, the luminescence efficiency and the service life of the organic light emitting device are improved. Further, at least one of $R^{19}$, $R^{21}$, and $R^{23}$ is selected from deuterium, deuterated methyl, deuterated phenyl, and deuterated methyl substituted phenyl. The lifetime of the organic light emitting device is further improved by the ortho-para effect. Further, in the present invention, by defining that $R^{15}$-$R^{18}$ are the same or different, and at least one of them is hydrogen; and/or $R^{19}$-$R^{23}$ are the same or different, and at least one of them is hydrogen, such that the substituents on the structure

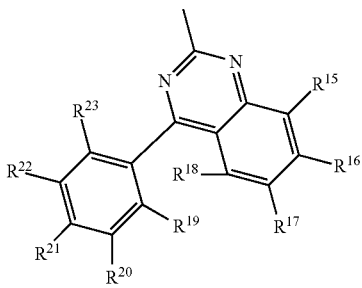

are not all substituted with deuterium. This structure interacts with the particular nitrogen-containing heterocyclic structure described above, which further facilitates the improvement of the service life of the device.

3) According to the organic light emitting device (OLED) provided in the present invention, the host material in the light-emitting layer comprises any one or a combination of at least two of the fused polycyclic compounds described above. As a host material in the light-emitting layer, the particular fused polycyclic compound allows the transport of charges and holes in the host material to become more balanced, thereby expanding the area where holes and electrons are recombined in the light emitting layer, reducing the exciton concentration, preventing the triplet-triplet annihilation of the device, and improving the efficiency of the device.

Moreover, the particular structure of the compound further facilitates the carrier recombination region in the host material of the OLED device to stay far away from the interface of the light emitting layer to the hole or electron transport layer, thus improving the color purity of the OLED device, avoiding the returning of excitons to the transport layer, and further improving the efficiency of the device The HOMO level and the LUMO level of the fused polycyclic compound according to the present invention match those of the adjacent hole transport layer and electron transport layer, so that the OLED device has a small driving voltage. Furthermore, the compound, used as the host material in the light emitting layer of the OLED device, has high triplet energy level and glass transition temperature, and good thermal stability, which ensures the efficient transfer of energy from the host material to the guest material and prevents the crystallization of the material molecules of the light emitting layer.

The compound of the present invention has a high singlet energy level, ensuring efficient energy transfer from the host material to the guest material; and has a small difference between the singlet ($\Delta E_{S1}$) and triplet energy level ($\Delta E_{T1}$), which promotes the reverse intersystem crossing of triplet excitons to singlet excitons. Moreover, the high reverse intersystem crossing (RISC) rate from the triplet state T1 to the singlet state S1 of the hot material can suppress the Dexter energy transfer (DET) from the host material to the luminescent dye, promote the FÖrster energy transfer, and reduce the exciton loss generated during the Dexter energy transfer (DET), thus avoiding the efficiency roll-off of the organic light-emitting device and improving the external quantum efficiency of the device, thereby achieving a high device efficiency.

BRIEF DESCRIPTION OF THE DRAWINGS

In order to more clearly explain the technical solutions in the specific embodiments of the present invention or in the prior art, the drawings used in the description of the specific embodiments or the prior art will be briefly described below. Obviously, the drawings depicted below are merely some embodiments of the present invention, and those skilled in the art can obtain other drawings based on these drawings without any creative efforts.

Figure 1:
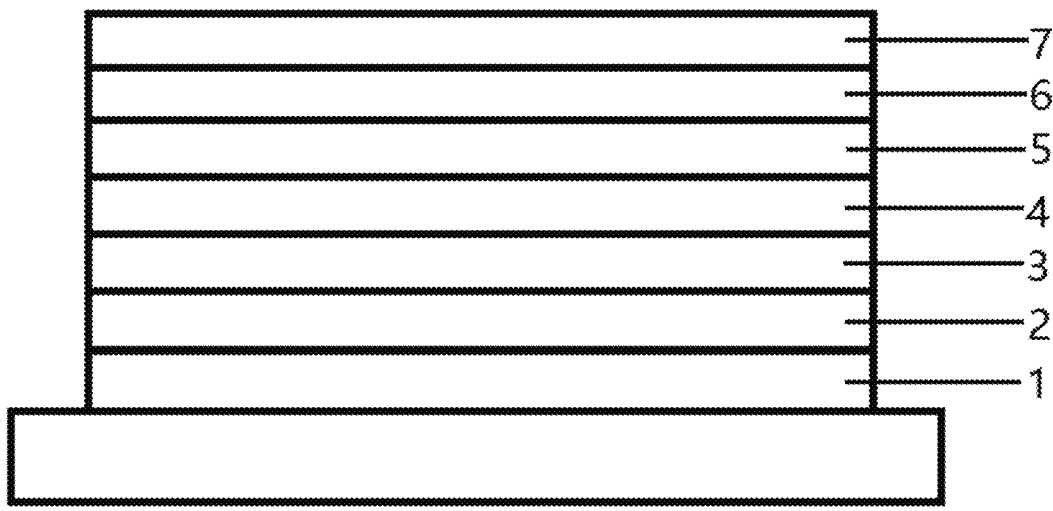
FIG. 1 is a schematic structural view of an organic light emitting device according to Examples 1 to 18 and Comparative Examples 1 to 2 of the present invention.

List of reference numerals:

1—anode, 2—hole injection layer, 3—hole transport layer, 4—organic light-emitting layer, 5—electron transport layer, 6—electron injection layer, 7—cathode.

DETAILED DESCRIPTION

The following examples are provided for better understanding of the present invention, which however are not restricted to the preferred embodiments, and not intended to limit the disclosure and protection scope of the present invention. Products that are the same as or similar to the present invention obtained by any skilled person with the suggestion of the present invention or by combining the present invention with other features in the prior art will fall within the protection scope of the present invention.

Where no specific experimental steps or conditions are indicated in the examples, the operation or conditions in the conventional experimental procedures described in the literatures in the art are followed. The reagents or instruments for which no manufacturers are noted are all common reagents and products commercially available from the market.

Example 1

This example provides an intermediate 3-1, an intermediate 3-2, an intermediate 3-3, and an intermediate 3-4, which are synthesized through the following routes.

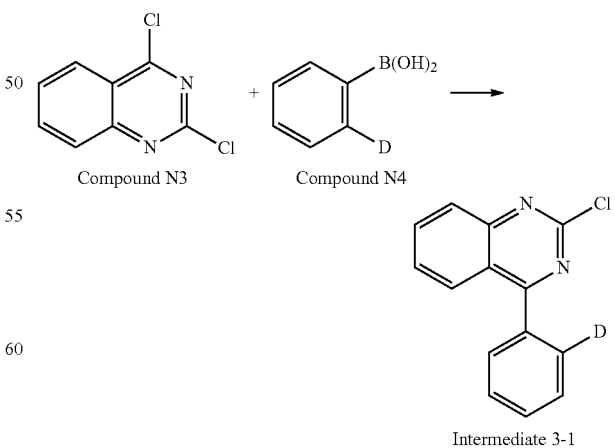

Intermediate 3-1

The intermediate 3-1 was prepared through a method comprising specifically the following steps. A stir bar was placed in a 500 ml two-neck round-bottom flask, and then a reflux pipe was connected. Next, the two-neck round-bottom flask was dried and filled with nitrogen. To the two-neck round-bottom flask, the compound N3 (23.8 g, 1.2 eq., 0.12 mol), the compound N4 (12.3 g, 0.1 mol), potassium carbonate (0.15 mol), ethanol (50 ml), water (50 ml), toluene (200 ml), and tetrakis(triphenylphosphine)palladium (5 mmol) were respectively added, heated to reflux, and reacted for 12 hrs. After complete reaction, the reaction solution was cooled to room temperature, quenched with water (200 ml), and extracted with dichloromethane (3×400 ml). The extract was collected, dried over magnesium sulfate, and filtrated. The filtrate was rotary dried to obtain a crude product. The crude product was purified by chromatography (ethyl acetate/hexane, volume ratio 1/10), to obtain the intermediate 3-1 (16.6 g, yield 69%).

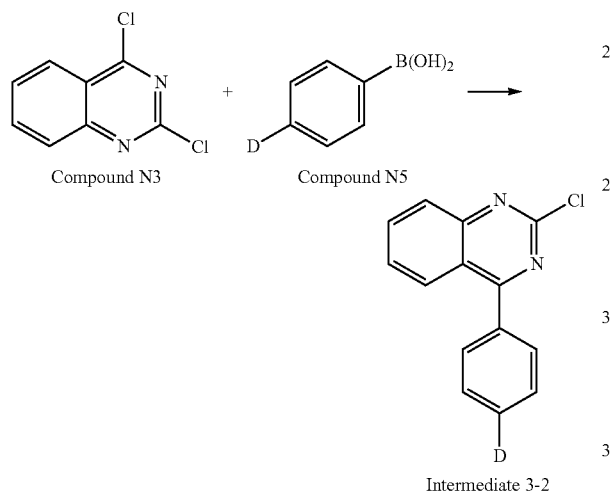

Intermediate 3-2

The preparation method of the intermediate 3-2 was the same as that for the intermediate 3-1, except that the compound N5 (12.31 g, 1.0 eq., 0.1 mol) was used in place of the compound N4, to obtain the intermediate 3-2 (16.9 g, yield 70%).

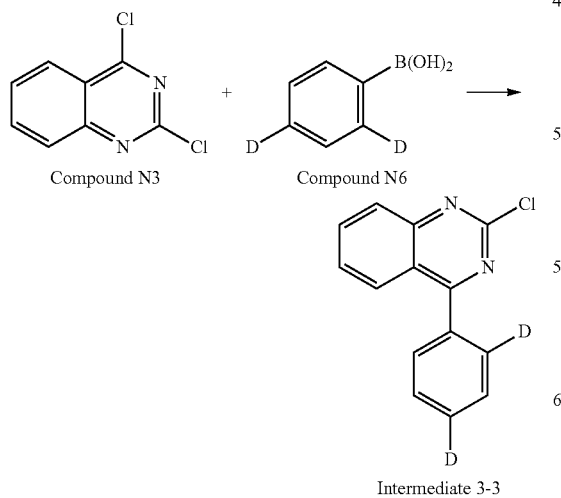

Intermediate 3-3

The preparation method of the intermediate 3-3 was the same as that for the intermediate 3-1, except that the compound N6 (12.4 g, 0.1 mol) was used in place of the compound N4, to obtain the intermediate 3-3 (16.7 g, yield 69%).

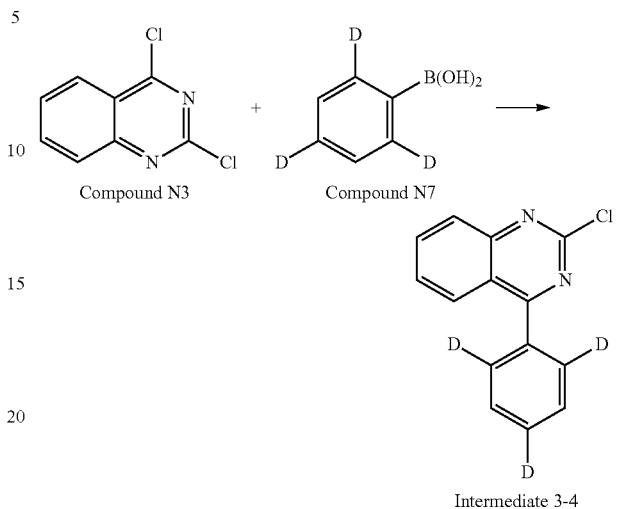

Intermediate 3-4

The preparation method of the intermediate 3-4 was the same as that for the intermediate 3-1, except that the compound N7 (12.5 g, 0.1 mol) was used in place of the compound N4, to obtain the intermediate 3-4 (16.3 g, yield 67%).

Example 2

This example provides a route for synthesizing a fused polycyclic compound 10.

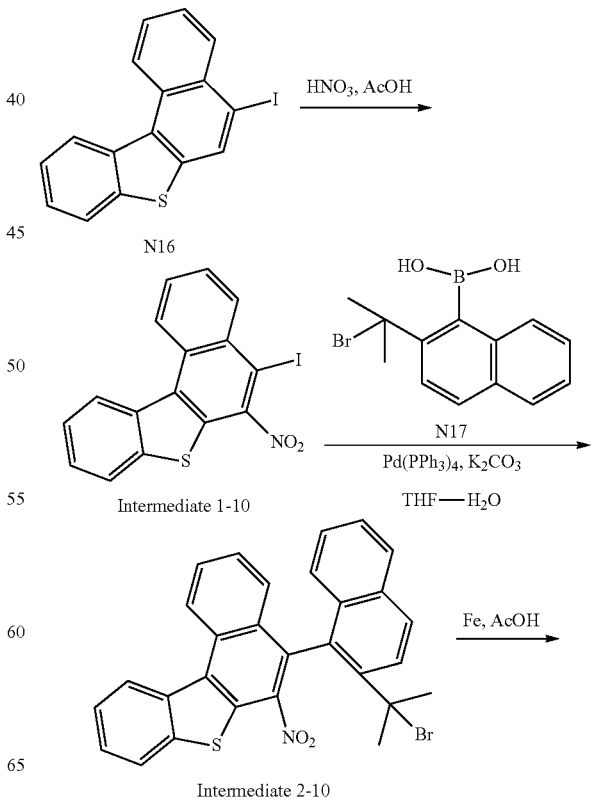

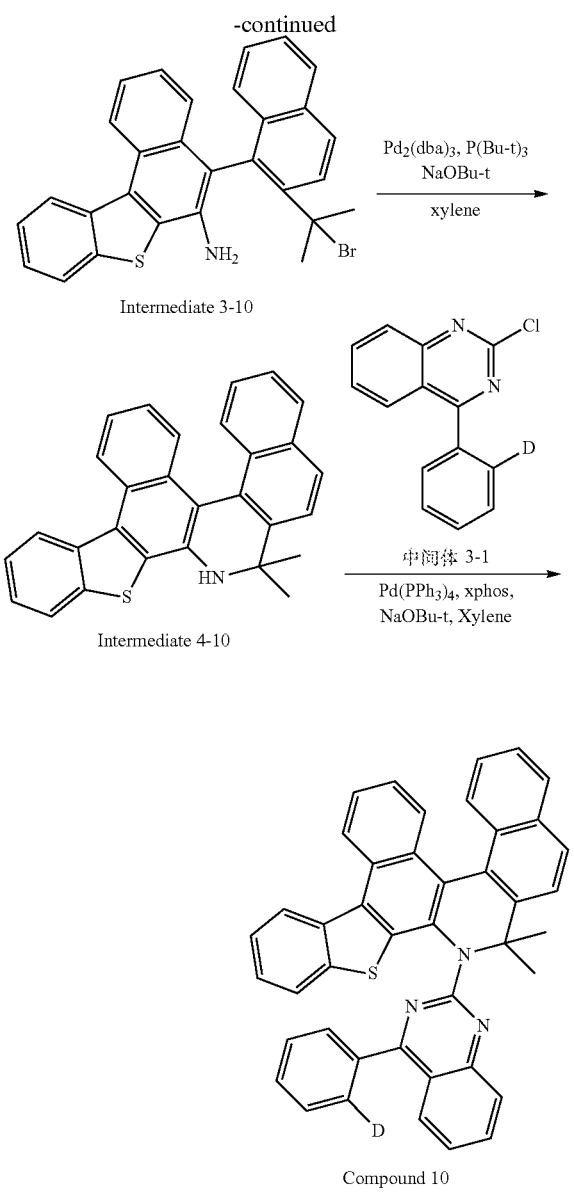

Intermediate 3-10

Intermediate 4-10

Compound 10

The compound 10 was prepared through a method comprising specifically the following steps.

1) Synthesis of intermediate 1-10. To a three-neck flask, acetic acid (500 mL), and the compound N16 (72.0 g, 0.20 mol) were added, and then 65 wt % concentrated nitric acid (20.3 g, 0.21 mol) was added dropwise at 0° C., and then stirred at 0° C. for 2 hrs. The reaction solution was poured into iced water (800 mL), neutralized with sodium hydroxide to pH=6-7, and then extracted with ethyl acetate (500 mL×2). The extracts were combined, washed with saturated brine (200 ml×2), and dried over sodium sulfate. The dried organic phase was rotary dried to obtain a product (78.2 g). The product was purified by column chromatography (PE:EA=20:1-5:1) to obtain the intermediate 1-10 (63.5 g, yield 78.4%).

2) Synthesis of intermediate 2-10: To a three-neck flask, the intermediate 1-10 (40.5 g, 0.10 mol), the compound N17 (29.3 g, 0.10 mol), potassium carbonate (27.6 g, 0.20 mol), and tetrahydrofuran-water (tetrahydrofuran/water volume ratio 3:1, 400 mL) were added. Tetrakis(triphenylphosphine) palladium (5 mmol) was then added under a nitrogen atmosphere. Subsequently, the reaction was heated to 75° C. and stirred for 4 hrs under a nitrogen atmosphere. The reaction solution was cooled, taken up in water (200 mL), and extracted with ethyl acetate (200 mL×2). The organic phase was rotary dried to obtain a crude product (55.3 g). The crude product was purified by column chromatography (PE:EA=10:1-5:1), to obtain the intermediate 2-10 (40.3 g, yield 76.5%).

3) Synthesis of intermediate 3-10: The intermediate 2-10 (26.3 g, 0.050 mol) was added to acetic acid (200 mL), and then iron powder (14 g, 0.25 mol) was added, and stirred at room temperature for 2 hrs. The iron powder was filtered off, and the acetic acid was removed by rotary drying, to obtain a crude product (35 g). The crude product was purified by column chromatography (PE:EA=5:1-3:1), to obtain the intermediate 3-10 (22.1 g, yield 89.1%).

4) Synthesis of intermediate 4-10: To a three-neck flask, the intermediate 3-10 (14.9 g, 0.030 mol), xylene (120 mL), a 10 wt % tri-tert-butylphosphine solution in xylene (6.0 g, 4 mol %), and sodium tert-butoxide (5.77 g, 0.060 mol) were added. $Pd_2(dba)_3$ (1.5 mmol) was then added under a nitrogen atmosphere. Subsequently, the reaction was heated to 140° C. and stirred for 4 hrs under a nitrogen atmosphere. The reaction solution was cooled to room temperature, and xylene was removed by rotary drying. The residue was directly purified by column chromatography (PE:EA=5:1-2:1), to obtain the intermediate 4-10 (9.4 g, yield 75.7%).

5) Synthesis of compound 10: To a three-neck flask, the intermediate 4-10 (8.3 g, 0.020 mol), the intermediate 3-1 (7.2 g, 0.030 mol), sodium tert-butoxide (3.85 g, 0.040 mol), xphos (400 mg), and xylene (60 mL) were added. Tetrakis(triphenylphosphine)palladium (200 mg) was then added under a nitrogen atmosphere. Subsequently, the reaction was heated to 140° C. and stirred for 4 hrs under a nitrogen atmosphere. The reaction solution was cooled, and the organic phase was rotary dried. The residue was purified by column chromatography (PE:EA=4:1-2:1), and beaten three times each in xylene and tetrahydrofuran (100 mL×6), to obtain the compound 10 (7.3 g, yield 58.0%).

Element analysis: ($C_{43}H_{28}DN_3S$) calculated: C, 83.20; H, 4.87; N, 6.77; S, 5.16; found: C, 83.23; H, 4.86; N, 6.76; S, 5.15; HRMS (ESI) m/z (M$^+$): calculated: 620.2145; found: 620.2147.

Example 3

This example provides a route for synthesizing a fused polycyclic compound 22.

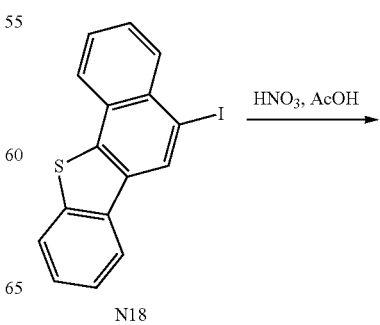

N18

-continued

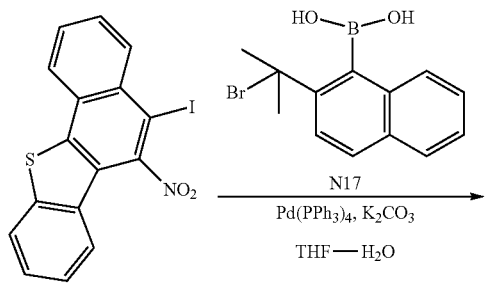

Intermediate 1-22

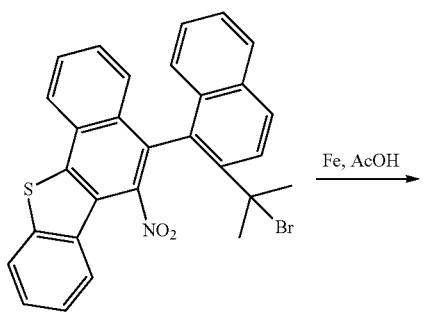

Intermediate 2-22

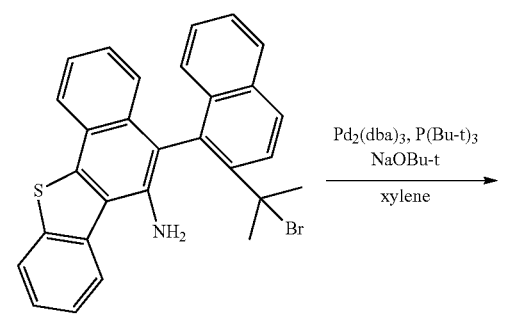

Intermediate 3-22

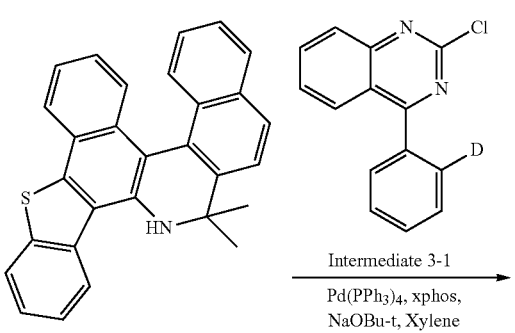

Intermediate 4-22

-continued

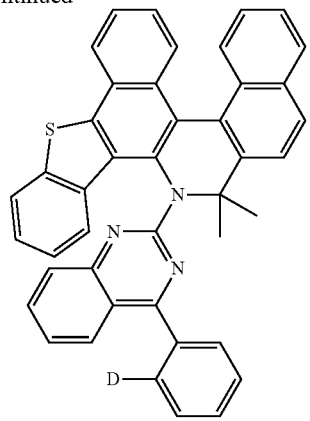

Compound 22

The compound 22 was prepared through a method comprising specifically the following steps.

1) Synthesis of intermediate 1-22: The synthesis method was the same as that for the intermediate 1-10, except that the compound N18 (72 g, 0.2 mol) was used in place of the compound N16, to obtain the intermediate 1-22 (63.2 g, yield 78%).

2) Synthesis of intermediate 2-22: The synthesis method was the same as that for the intermediate 2-10, except that the intermediate 1-22 (40.50 g, 0.1 mol) was used in place of the intermediate 1-10, to obtain the intermediate 2-22 (40.1 g, yield 76.3%).

3) Synthesis of intermediate 3-22: The synthesis method was the same as that for the intermediate 3-10, except that the intermediate 2-22 (26.25 g, 0.05 mol) was used in place of the intermediate 2-10, to obtain the intermediate 3-22 (19.7 g, yield 91.2%).

4) Synthesis of intermediate 4-22: The synthesis method was the same as that for the intermediate 4-10, except that the intermediate 3-22 (12.93 g, 0.03 mol) was used in place of the intermediate 3-10, to obtain the intermediate 4-22 (9.3 g, yield 75.1%).

5) Synthesis of compound 22: The synthesis method was the same as that for the compound 10, except that the intermediate 4-22 (8.3 g, 0.02 mol) was used in place of the intermediate 4-10, to obtain the compound 22 (6.8 g, yield 55.1%).

Element analysis: ($C_{43}H_{28}DN_3S$) calculated: C, 83.20; H, 4.87; N, 6.77; S, 5.16; found: C, 83.22; H, 4.86; N, 6.76; S, 5.16; HRMS (ESI) m/z ($M^+$): calculated: 620.2145; found: 620.2146.

Example 4

This example provides a route for synthesizing a fused polycyclic compound 26.

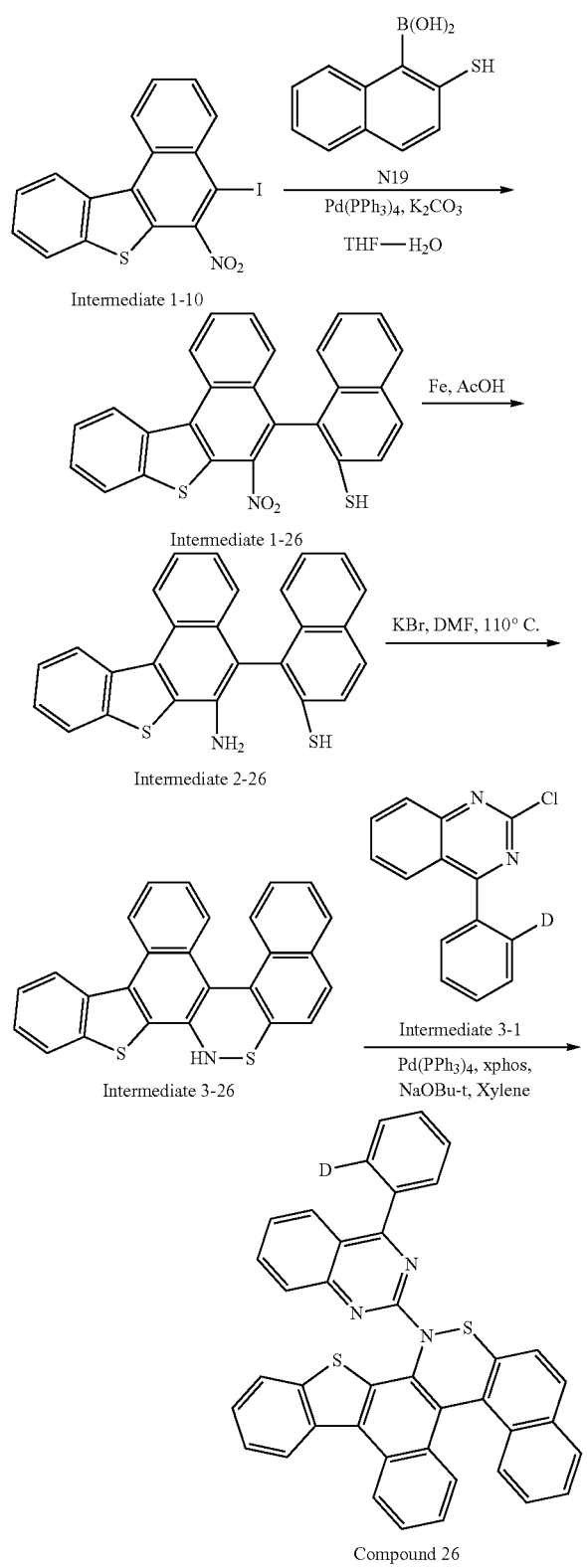

Compound 26

The compound 26 was prepared through a method comprising specifically the following steps.

1) Synthesis of intermediate 1-26: To a three-neck flask, the intermediate 1-10 (81.0 g, 0.20 mol), 2-mercapto-1-naphthaleneboronic acid (the compound N19) (49.0 g, 0.24 mol), potassium carbonate (55.2 g, 0.40 mol), and tetrahydrofuran-water (tetrahydrofuran/water volume ratio 3:1, 600 mL) were added. Tetrakis(triphenylphosphine)palladium (2.0 g) was then added under a nitrogen atmosphere. Subsequently, the reaction was heated to 75° C. and stirred for 4 hrs under a nitrogen atmosphere. The reaction solution was cooled, taken up in water (300 mL), and extracted with ethyl acetate (300 mL×2). The organic phase was rotary dried to obtain a crude product. The crude product was purified by column chromatography (PE:EA=8:1-3:1), to obtain the intermediate 1-26 (62.5 g, yield 71.4%).

2) Synthesis of intermediate 2-26: The intermediate 1-26 (43.7 g, 0.10 mol) was added to acetic acid (300 mL), and then iron powder (28 g, 0.50 mol) was added, and stirred at room temperature for 2 hrs. The iron powder was filtered off, and the acetic acid was removed by rotary drying, to obtain a crude product. The crude product was purified by column chromatography (PE:EA=5:1-2:1), to obtain the intermediate 2-26 (37 g, yield 91%).

3) Synthesis of intermediate 3-26: The intermediate 2-26 (20.4 g, 0.050 mol) was dissolved in DMF (100 mL) in a three-neck flask, and then potassium bromide (1.19 g, 0.010 mol) was added and reacted at 110° C. for 12 hrs. The reaction solution was cooled, rotary dried to remove the solvent, diluted with water (100 mL), and extracted with ethyl acetate (100 mL×2). The organic phases were combined, washed with saturated saline (100 mL×2), and dried over sodium sulfate. The solvent was removed by rotary dried, and a crude product 3-26 (18.5 g) was obtained, which was purified by column chromatography (PE:EA=3:1-1:1), and rotary dried to obtain the intermediate 3-26 (13.5 g, yield 66.6%).

4) Synthesis of compound 26: To a three-neck flask, the intermediate 3-26 (8.1 g, 0.020 mol), the intermediate 3-1 (7.23 g, 0.030 mol), sodium tert-butoxide (3.85 g, 0.040 mol), xphos (400 mg), and xylene (60 mL) were added. Tetrakis(triphenylphosphine)palladium (200 mg) was then added under a nitrogen atmosphere. Subsequently, the reaction was heated to 140° C. and stirred for 4 hrs under a nitrogen atmosphere. The reaction solution was cooled, and the organic phase was rotary dried. The residue was purified by column chromatography (PE:EA=4:1-2:1) to obtain a crude product of the compound 26, which was beaten three times each in xylene and tetrahydrofuran (80 mL×6), to obtain the compound 26 (7.8 g, yield 64%).

Element analysis: $C_{40}H_{22}DN_3S_2$ calculated: C, 78.66; H, 3.96; N, 6.88; found: C, 78.64; H, 3.96; N, 6.89; HRMS (ESI) m/z (M+): calculated: 610.1396; found: 610.1400.

Example 5

The intermediate 2 provided in this example is synthesized through a route shown below.

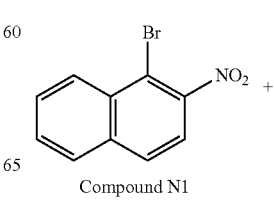

Compound N1

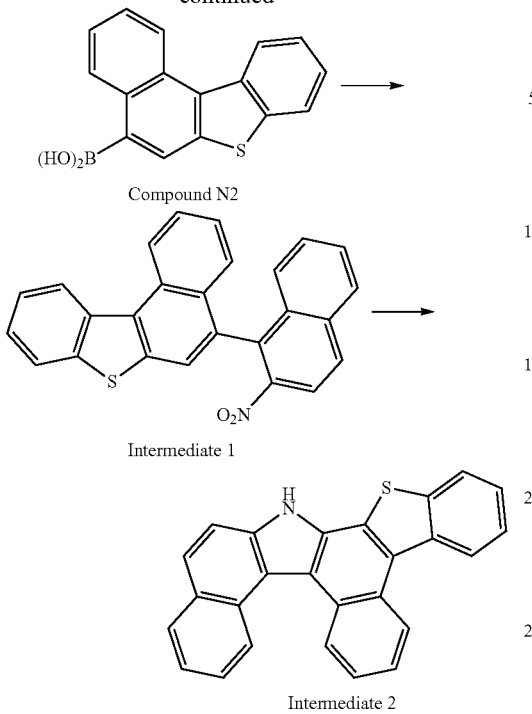

Example 6

This example provides a route for synthesizing a fused polycyclic compound 36.

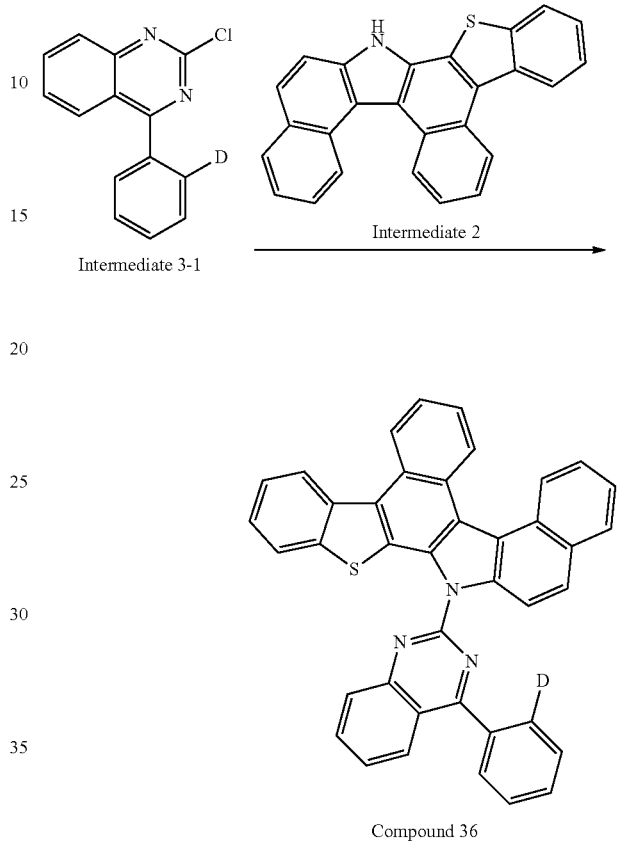

The intermediate 2 was prepared through a method comprising specifically the following steps.

1) Synthesis of intermediate 1: A stir bar was placed in a 500 ml two-neck round-bottom flask, and then a reflux pipe was connected. Next, the two-neck round-bottom flask was dried and filled with nitrogen. To the two-neck round-bottom flask, the compound N1 (30.1 g, 0.12 mol), the compound N2 (27.8 g, 0.1 mol), potassium carbonate (27.6 g, 0.2 mol), and tetrahydrofuran-water (tetrahydrofuran/water volume ratio 3:1, 200 mL) were added. Tetrakis(triphenylphosphine) palladium (1.0 g) was then added under a nitrogen atmosphere. Subsequently, the reaction was heated to 75° C. and stirred for 4 hrs under a nitrogen atmosphere. The reaction solution was cooled, taken up in water (150 mL), and extracted with ethyl acetate (150 mL×2). The organic phase was rotary dried to obtain a crude product. The crude product was purified by column chromatography (PE:EA=20:1-8:1), to obtain the intermediate 1 as a yellow solid (65.4 g, yield 81%).

2) Synthesis of intermediate 2: A stir bar was placed in a 500 ml two-neck round-bottom flask, and then a reflux pipe was connected. Next, the two-neck round-bottom flask was dried and filled with nitrogen. To the two-neck round-bottom flask, the intermediate 1 (40.5 g, 0.1 mol) and triethyl phosphite (250 mL) were respectively added and stirred at 120° C. for 16 hrs. The reaction solution was cooled, rotary dried to remove the solvent, added with water (200 mL), and then extracted with ethyl acetate (200 mL×2). The organic phases were combined, washed with saturated saline, dried over sodium sulfate, and rotary dried to obtain a crude product (41.5 g). The crude product was purified by column chromatography (PE:EA=10:1-5:1), and then rotary dried to obtain the intermediate 2 (30.2 g, yield 81%).

The compound 36 was prepared through a method comprising specifically the following steps.

Synthesis of compound 36: A stir bar was placed in a 500 ml two-neck round-bottom flask, and then a reflux pipe was connected. Next, the two-neck round-bottom flask was dried and filled with nitrogen. To the two-neck round-bottom flask, the intermediate 3-1 (24.1 g, 0.1 mol), the intermediate 2 (37.3 g, 0.1 mol), tert-BuNa (sodium tert-butoxide, 0.3 mol), and xphos (2 g) were added, and then xylene (100 ml), and Pd[PPh$_3$]$_4$ (tetrakis(triphenylphosphine)palladium, 0.005 mol) were added. The mixture was stirred at 140° C. for 5 hrs, and then cooled to room temperature after reaction. The reaction system was filtered and concentrated; and the crude product was purified by chromatography (ethyl acetate/hexane, volume ratio 1/10) to obtain the compound 36 (42.2 g, yield 73%).

Element analysis: $C_{40}H_{22}DN_3S$ calculated: C, 83.02; H, 4.18; N, 7.26; found: C, 83.05; H, 4.16; N, 7.25; HRMS (ESI) m/z (M+): calculated: 578.1675; found: 578.1681.

Example 7

This example provides a route for synthesizing a fused polycyclic compound 37.

67

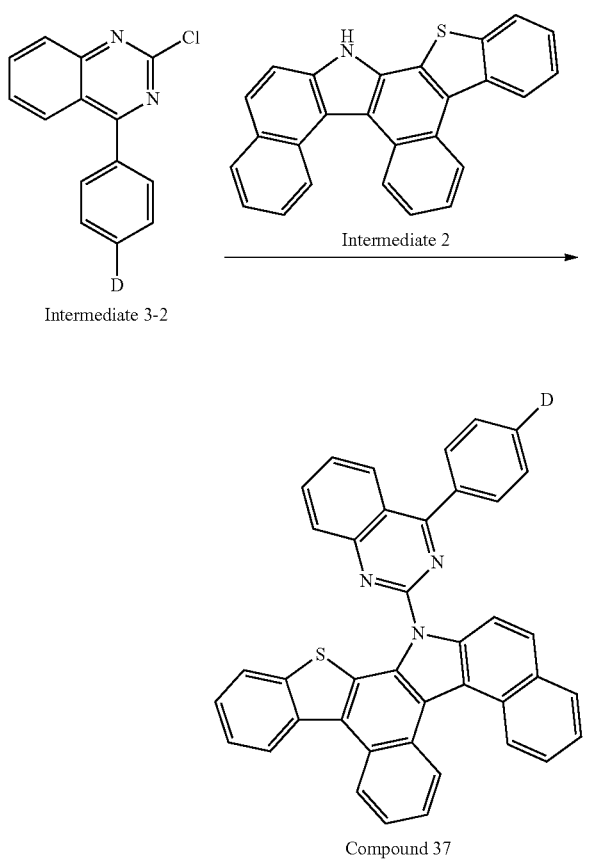 [SMILES: [2H]c1ccc(-c2nc(Cl)nc3ccccc23)cc1 ; c1ccc2c(c1)ccc1[nH]c3c4sc5ccccc5c4c4ccccc4c3c12 ; [2H]c1ccc(-c2nc(-n3c4ccc5ccccc5c4c4c5ccccc5c5c6ccccc6sc5c43)nc3ccccc23)cc1]

Intermediate 3-2

Compound 37

The compound 37 was prepared through a method comprising specifically the following steps.

Synthesis of compound 37: The synthesis method was the same as that for the compound 36, except that the intermediate 3-2 (24.1 g, 0.1 mol) was used in place of the intermediate 3-1, to obtain the compound 37 (41.1 g, yield 71%).

Element analysis: $C_{40}H_{22}DN_3S$ calculated: C, 83.02; H, 4.18; N, 7.26; found: C, 83.07; H, 4.16; N, 7.25; HRMS (ESI) m/z (M+): calculated: 578.1675; found: 578.1671.

Example 8

This example provides a route for synthesizing a fused polycyclic compound 38.

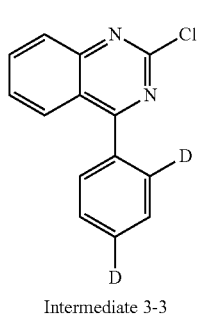

Intermediate 3-3

68

-continued

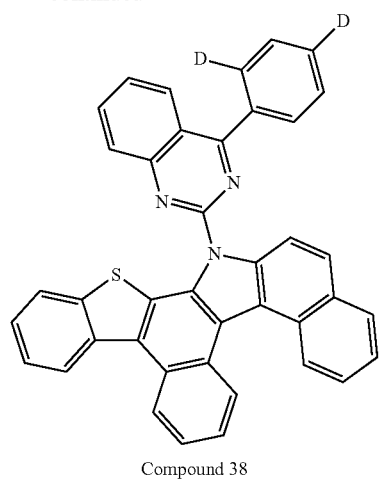

Compound 38

The compound 38 was prepared through a method comprising specifically the following steps.

Synthesis of compound 38: The synthesis method was the same as that for the compound 36, except that the intermediate 3-3 (24.2 g, 0.1 mol) was used in place of the intermediate 3-1, to obtain the compound 38 (41.0 g, yield 71%).

Element analysis: $C_{40}H_{21}D_2N_3S$ calculated: C, 82.87; H, 4.35; N, 7.25; found: C, 82.83; H, 4.37; N, 7.27; HRMS (ESI) m/z (M+): calculated: 579.1738; found: 579.1742.

Example 9

This example provides a route for synthesizing a fused polycyclic compound 39.

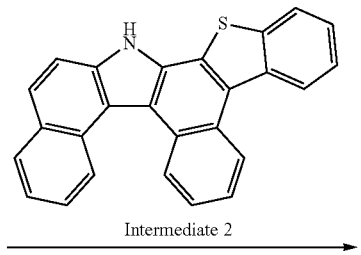

Intermediate 3-4

69
-continued

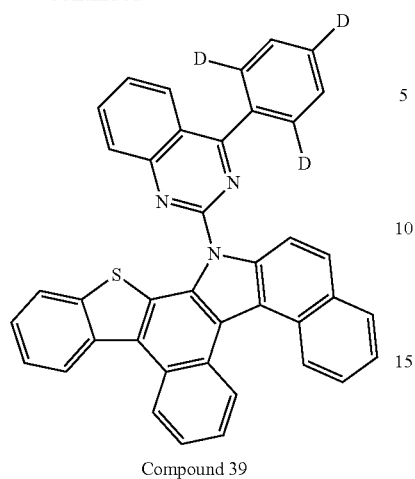

Compound 39

The compound 39 was prepared through a method comprising specifically the following steps.

Synthesis of compound 39: The synthesis method was the same as that for the compound 36, except that the intermediate 3-4 (24.3 g, 0.1 mol) was used in place of the intermediate 3-1, to obtain the compound 39 (39.5 g, yield 68%).

Element analysis: $C_{40}H_{20}D_3N_3S$ calculated: C, 82.73; H, 4.51; N, 7.24; found: C, 82.77; H, 4.51; N, 7.22; HRMS (ESI) m/z (M+): calculated: 580.1801; found: 580.1808.

Example 10

This example provides a route for synthesizing a fused polycyclic compound 46.

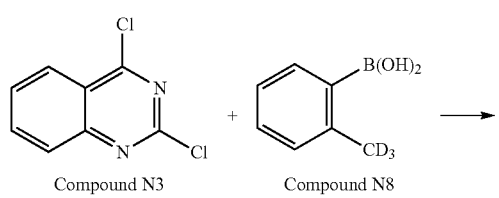

Compound N3 + Compound N8 →

70
-continued

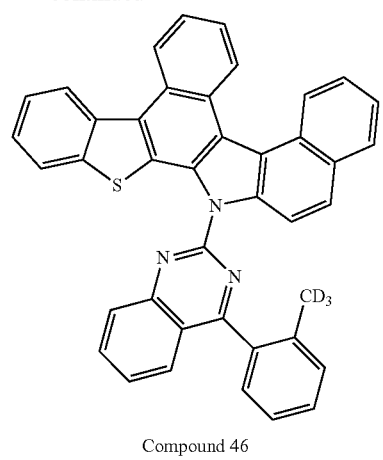

Compound 46

The compound 46 was prepared through a method comprising specifically the following steps.

Synthesis of intermediate 3-5: The synthesis method was the same as that for the intermediate 3-1, except that the compound N8 (13.9 g, 0.1 mol) was used in place of the compound N4, to obtain the intermediate 3-5 (16.5 g, yield 64%).

Synthesis of compound 46: The synthesis method was the same as that for the compound 36, except that the intermediate 3-5 (25.7 g) was used in place of the intermediate 3-1, to obtain the compound 46 (40.4 g, yield 68%).

Element analysis: $C_{41}H_{22}D_3N_3S$ calculated: C, 82.80; H, 4.74; N, 7.07; found: C, 82.83; H, 4.73; N, 7.06; HRMS (ESI) m/z (M+): calculated: 594.1957; found: 594.1962.

Example 11

This example provides a route for synthesizing a fused polycyclic compound 47.

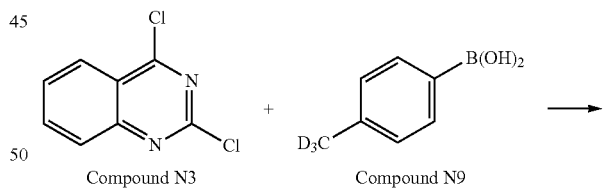

Compound N3 + Compound N9 →

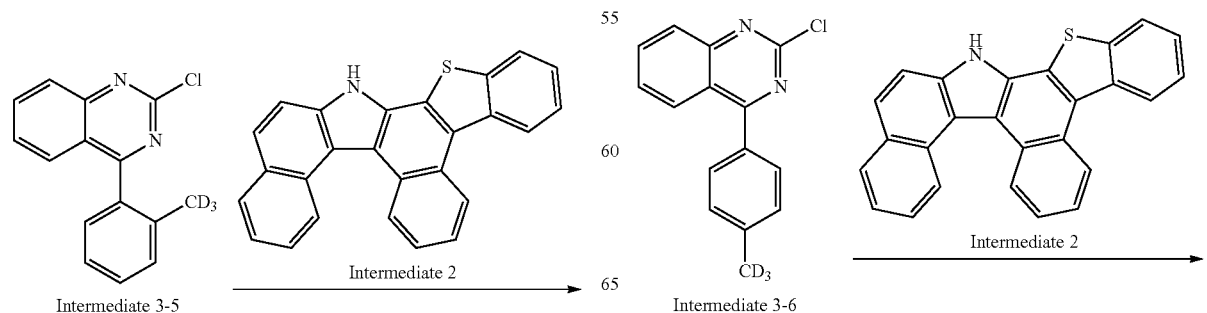

Intermediate 3-5 —Intermediate 2→

Intermediate 3-6 —Intermediate 2→

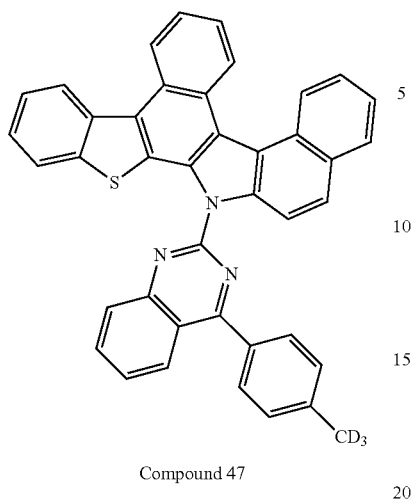

Compound 47

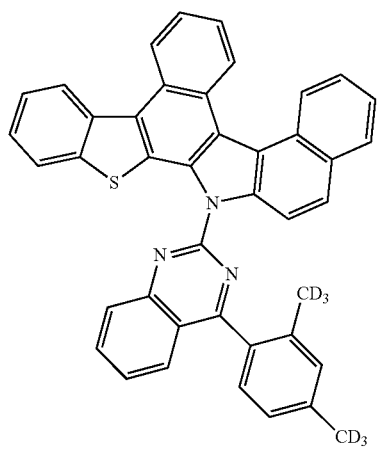

Compound 48

The compound 47 was prepared through a method comprising specifically the following steps.

Synthesis of intermediate 3-6: The synthesis method was the same as that for the intermediate 3-1, except that the compound N9 (13.9 g, 0.1 mol) was used in place of the compound N4, to obtain the intermediate 3-6 (16.7 g, yield 65%).

Synthesis of compound 47: The synthesis method was the same as that for the compound 36, except that the intermediate 3-6 (25.7 g) was used in place of the intermediate 3-1, to obtain the compound 47 (40.4 g, yield 68%).

Element analysis: $C_{41}H_{22}D_3N_3S$ calculated: C, 82.80; H, 4.74; N, 7.07; found: C, 82.82; H, 4.73; N, 7.06; HRMS (ESI) m/z (M+): calculated: 594.1957; found: 594.1963.

The compound 48 was prepared through a method comprising specifically the following steps.

Synthesis of intermediate 3-7: The synthesis method was the same as that for the intermediate 3-1, except that the compound N10 (15.6 g, 0.1 mol) was used in place of the compound N4, to obtain the intermediate 3-7 (17.3 g, yield 63%).

Synthesis of compound 48: The synthesis method was the same as that for the compound 36, except that the intermediate 3-7 (27.4 g) was used in place of the intermediate 3-1, to obtain the compound 48 (39.7 g, yield 65%).

Element analysis: $C_{42}H_{21}D_6N_3S$ calculated: C, 82.46; H, 5.44; N, 6.87; found: C, 82.48; H, 5.43; N, 6.86; HRMS (ESI) m/z (M+): calculated: 611.2302; found: 611.2308.

Example 12

This example provides a route for synthesizing a fused polycyclic compound 48.

Example 13

This example provides a route for synthesizing a fused polycyclic compound 49.

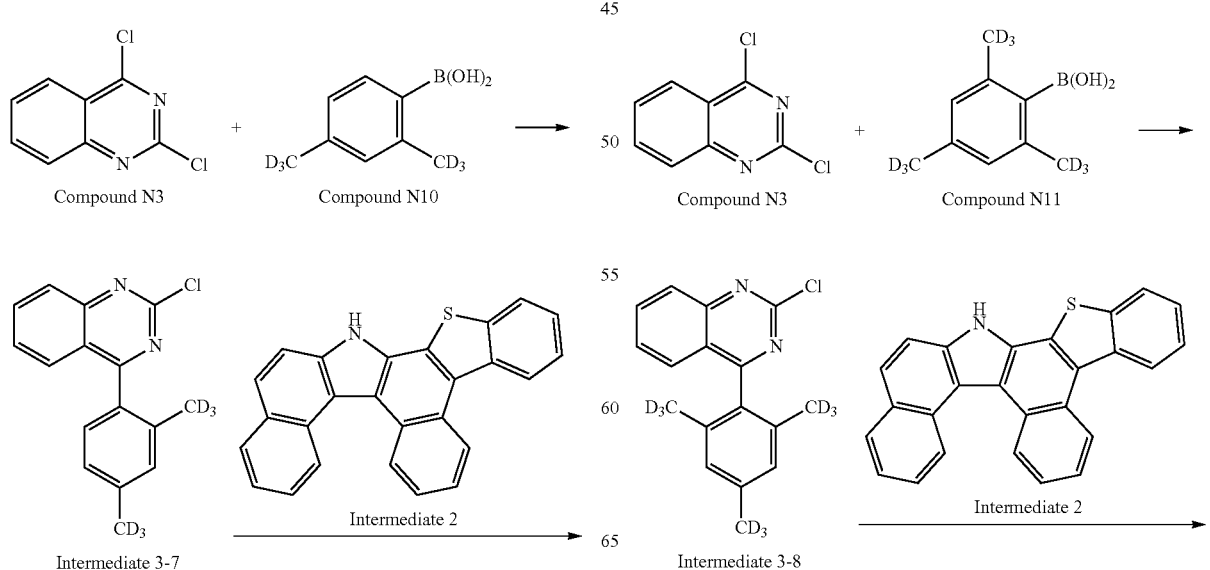

-continued

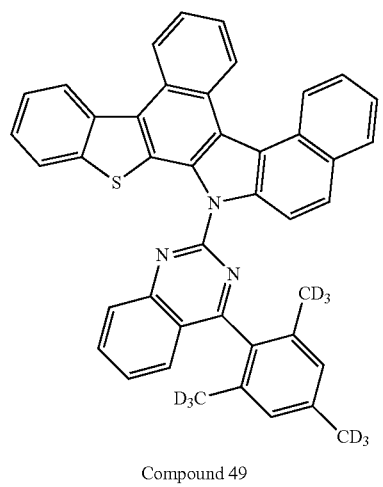

Compound 49

Synthesis of intermediate 3-8: The synthesis method was the same as that for the intermediate 3-1, except that the compound N11 (17.3 g, 1 eq., 0.1 mol) was used in place of the compound N4, to obtain the intermediate 3-8 (17.8 g, yield 61%).

Synthesis of compound 49: The synthesis method was the same as that for the compound 36, except that the intermediate 3-8 (29.1 g) was used in place of the intermediate 3-1, to obtain the compound 49 (40.2 g, yield 64%).

Element analysis: $C_{43}H_{20}D_9N_3S$ calculated: C, 82.13; H, 6.09; N, 6.68; found: C, 82.12; H, 6.09; N, 6.69; HRMS (ESI) m/z (M+): calculated: 628.2647; found: 628.2653.

Example 14

This example provides a route for synthesizing a fused polycyclic compound 73.

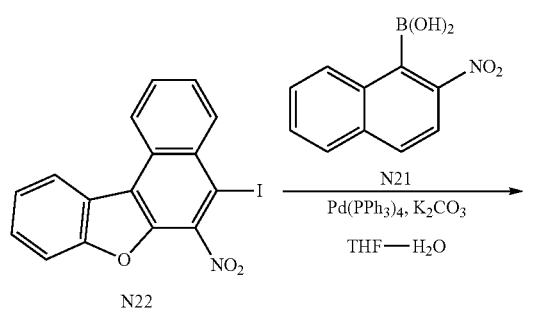

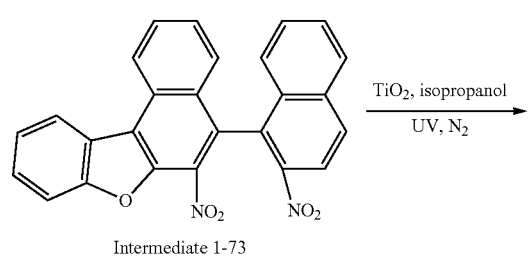

Intermediate 1-73

-continued

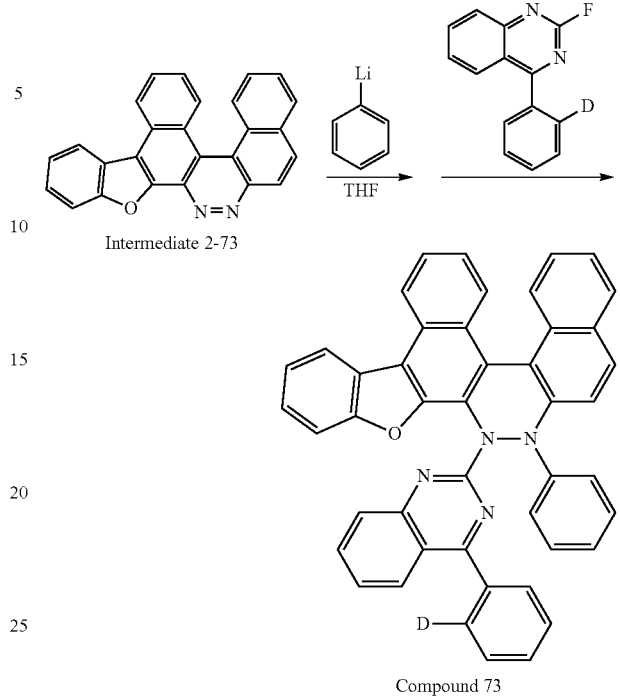

Compound 73

The compound 73 was prepared through a method comprising specifically the following steps.

1) Synthesis of compound N22: The synthesis method of the compound N22 was the same as that for the intermediate 1-10, except that (0.2 mol) was used in place of and the yield was 74%.

2) Synthesis of intermediate 1-73: To a three-neck flask, the compound N22 (38.9 g, 0.10 mol), the compound N21 (21.7 g, 0.10 mol), potassium carbonate (27.6 g, 0.20 mol), and tetrahydrofuran-water (tetrahydrofuran/water volume ratio 3:1, 400 mL) were added. Tetrakis(triphenylphosphine) palladium (1.0 g) was then added under a nitrogen atmosphere. Subsequently, the reaction was heated to 75° C. and stirred for 4 hrs under a nitrogen atmosphere. The reaction solution was cooled, taken up in water (200 mL), and extracted with ethyl acetate (200 mL×2). The organic phase was rotary dried to obtain a crude product (46.3 g). The crude product was purified by column chromatography (PE:EA=20:1-10:1), to obtain the intermediate 1-73 (32.1 g, yield 74%).

3) Synthesis of intermediate 2-73: To a three-neck flask, the intermediate 1-73 (21.7 g, 0.05 mol) was added, isopropanol (200 mL) was added to dissolve the intermediate, and then titania (8.0 g, 0.10 mol) was added. Under a nitrogen atmosphere, the reaction was continued for 16 hrs under UV irradiation. The solvent was rotary dried, and the residue was purified by column chromatography (PE:EA=15:1-5:1) to obtain the intermediate 2-73 (12.0 g, yield 65%).

4) Synthesis of compound 73: To a three-neck flask, the intermediate 2-73 (7.4 g, 0.02 mol) was added, and then anhydrous tetrahydrofuran (50 mL) was added, and cooled to −78° C. Phenyl lithium (20 mL, 0.02 mol) was added dropwise and stirred for 2 hrs while the temperature was maintained at −78° C. Then a solution of the compound

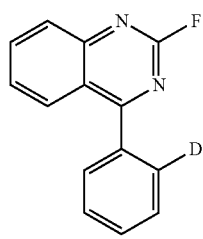 [SMILES: [2H]c1ccccc1-c1nc(F)nc2ccccc12]

(4.5 g, 0.02 mol) in tetrahydrofuran (30 mL) was added dropwise. After the addition, the mixture was incubated at −78° C. for 2 hrs and then allowed to warm to room temperature overnight. The reaction solution was quenched with water (100 mL), extracted with ethyl acetate (100 mL×2), washed with saturated saline, dried over sodium sulfate, and rotary dried to obtain a crude product (12.5 g), which was purified by column chromatography (PE:EA=7:1-3:1), to obtain the compound 73 (8.2 g, yield 63%).

Element analysis: $C_{46}H_{27}DN_4O$ calculated: C, 84.51; H, 4.47; N, 8.57; found: C, 84.54; H, 4.48; N, 8.58; HRMS (ESI) m/z (M+): calculated: 653.2326; found: 653.2334.

Example 15

This example provides a route for synthesizing a fused polycyclic compound 67.

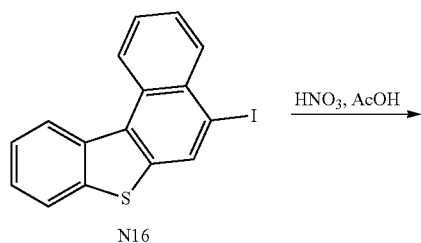

N16

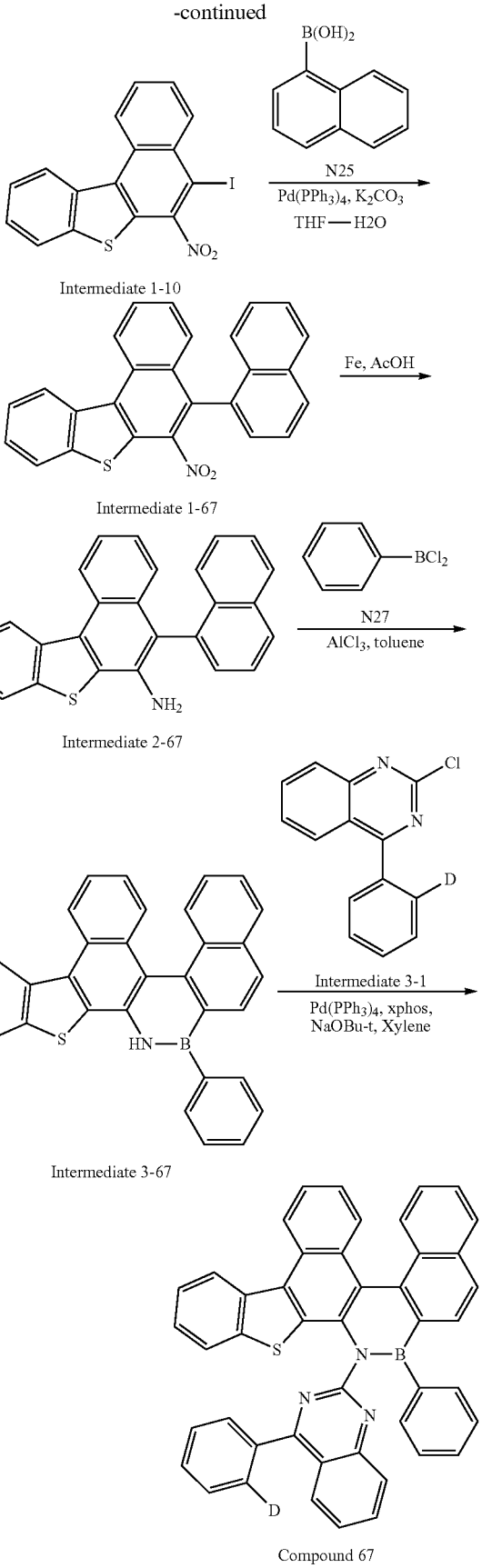

Compound 67

The compound 67 was prepared through a method comprising specifically the following steps.

1) Synthesis of intermediate 1-67: To a three-neck flask, the intermediate 1-10 (81.0 g, 0.20 mol), 1-naphthaleneboronic acid (41.3 g, 0.24 mol), potassium carbonate (55.2 g, 0.40 mol), and tetrahydrofuran-water (tetrahydrofuran/water volume ratio 3:1, 500 mL) were added. Tetrakis(triphenylphosphine)palladium (2.0 g) was then added under a nitrogen atmosphere. Subsequently, the reaction was heated to 75° C. and stirred for 4 hrs under a nitrogen atmosphere. The reaction solution was cooled and extracted. The organic phase was rotary dried to obtain a crude product (100.5 g). The crude product was purified by column chromatography (PE:EA=10:1-5:1), to obtain the intermediate 1-67 (60.5 g, yield 74.6%).

2) Synthesis of intermediate 2-67: The intermediate 1-67 (40.5 g, 0.10 mol) was added to acetic acid (300 mL), and then iron powder (28 g, 0.50 mol) was added, and stirred at room temperature for 2 hrs. The iron powder was filtered off, and the acetic acid was removed by rotary drying, to obtain a crude product (50 g). The crude product was purified by column chromatography (PE:EA=5:1-3:1), to obtain the intermediate 2-67 (34.2 g, yield 91.1%).

3) Synthesis of intermediate 3-67: To a three-neck flask, the intermediate 2-67 (18.8 g, 0.05 mol), phenylboron dichloride (9.5 g, 0.06 mol), anhydrous toluene (150 mL), and aluminum trichloride (10.0 g, 0.08 mol) were added. Under a nitrogen atmosphere, the mixture was refluxed in toluene for 4 hrs, cooled, and filtered. The filtrate was washed with saturated brine (100 mL), rotary dried, and beaten twice in toluene (100 mL×2), to obtain the intermediate 3-67 (15.0 g, 65%).

4) Synthesis of compound 67: To a three-neck flask, the intermediate 3-67 (9.2 g, 0.020 mol), the intermediate 3-1 (7.22 g, 0.030 mol), sodium tert-butoxide (3.9 g, 0.040 mol), xphos (400 mg), and xylene (60 mL) were added. Tetrakis(triphenylphosphine)palladium (200 mg) was then added under a nitrogen atmosphere. Subsequently, the reaction was heated to 140° C. and stirred for 4 hrs under a nitrogen atmosphere. The reaction solution was cooled, and the organic phase was rotary dried. The residue was purified by column chromatography (PE:EA=4:1-2:1), and beaten three times each in xylene and tetrahydrofuran (80 mL×6), to obtain the compound 67 (8.2 g, yield 62%).

Element analysis: ($C_{46}H_{27}DBN_3S$) calculated: C, 82.88; H, 4.38; N, 6.30; S, 4.81; found: C, 82.90; H, 4.38; N, 6.29; S, 4.80; HRMS (ESI) m/z ($M^+$): calculated: 666.2160; found: 666.2167.

Example 16

This example provides a route for synthesizing a fused polycyclic compound 107.

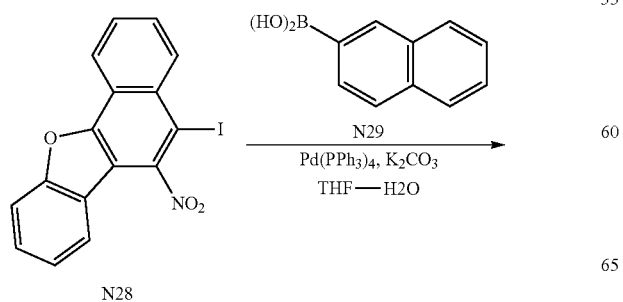

N28

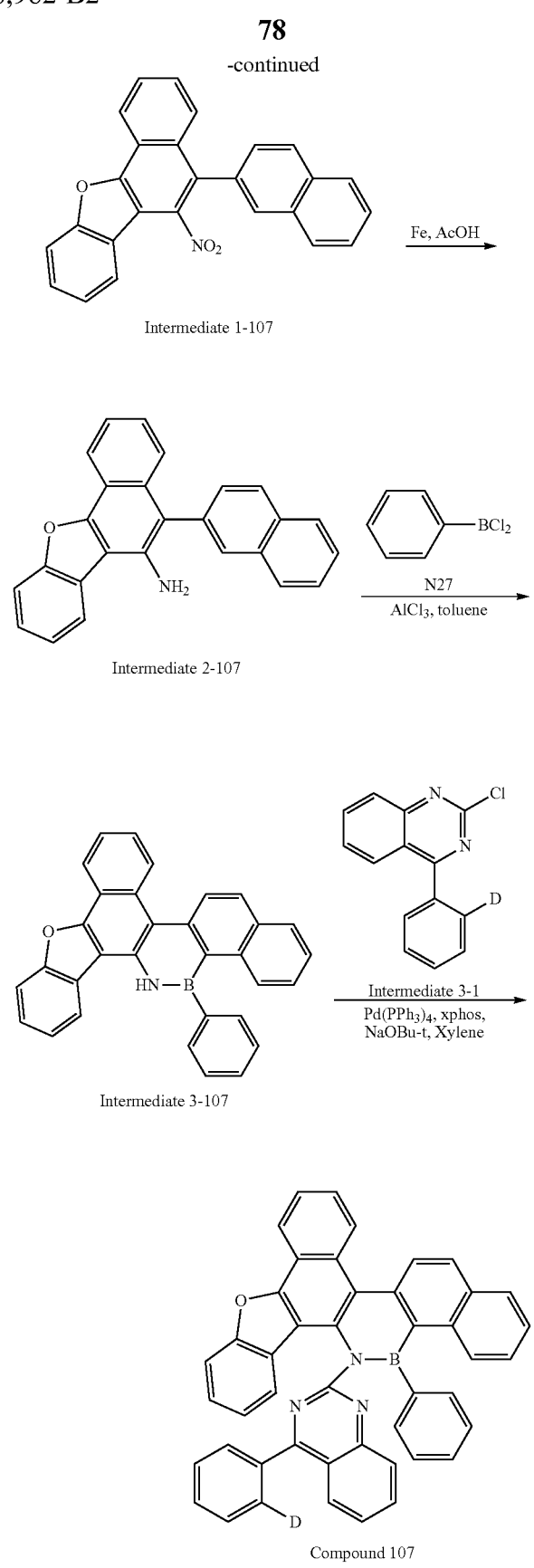

Intermediate 1-107

Intermediate 2-107

Intermediate 3-107

Compound 107

The compound 107 was prepared through a method comprising specifically the following steps.

Synthesis of compound N28: The synthesis method of the compound N28 was the same as that for the intermediate 1-10, except that

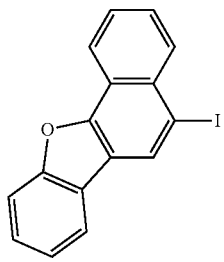 [SMILES: Ic1cc2c3ccccc3oc2c2ccccc12]

(0.1 mol) was used in place of

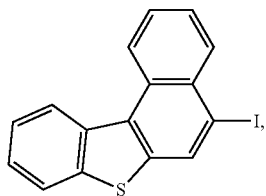 [SMILES: Ic1cc2sc3ccccc3c2c2ccccc12]

and the yield was 71%.

Synthesis of intermediate 1-107: The synthesis method was the same as that for the intermediate 1-67, except that the compound N28 (77.8 g, 0.20 mol) was used in place of the compound N26, and the compound N29 was used in place of the intermediate 1-10, to obtain the intermediate 1-107 (56.8 g, yield 73.0%).

Synthesis of intermediate 2-107: The synthesis method was the same as that for the intermediate 2-67, except that the intermediate 1-107 (38.9 g, 0.01 mol) was used in place of the intermediate 1-67, to obtain the intermediate 2-107 (33.5 g, yield 93.2%).

Synthesis of intermediate 3-107: The synthesis method was the same as that for the intermediate 3-67, except that the intermediate 2-107 (18.0 g, 0.05 mol) was used in place of the intermediate 2-67, to obtain the intermediate 3-107 (14.9 g, yield 67%).

Synthesis of compound 107: The synthesis method was the same as that for the compound 67, except that the intermediate 3-107 (8.9 g, 0.02 mol) was used in place of the intermediate 3-67, to obtain the compound 107 (8.2 g, yield 63.0%).

Element analysis: ($C_{46}H_{27}DBN_3O$) calculated: C, 84.93; H, 4.49; N, 6.46; found: C, 84.97; H, 4.49; N, 6.45; HRMS (ESI) m/z (M$^+$): calculated: 650.2388; found: 650.2394.

Example 17

This example provides a route for synthesizing a fused polycyclic compound 92.

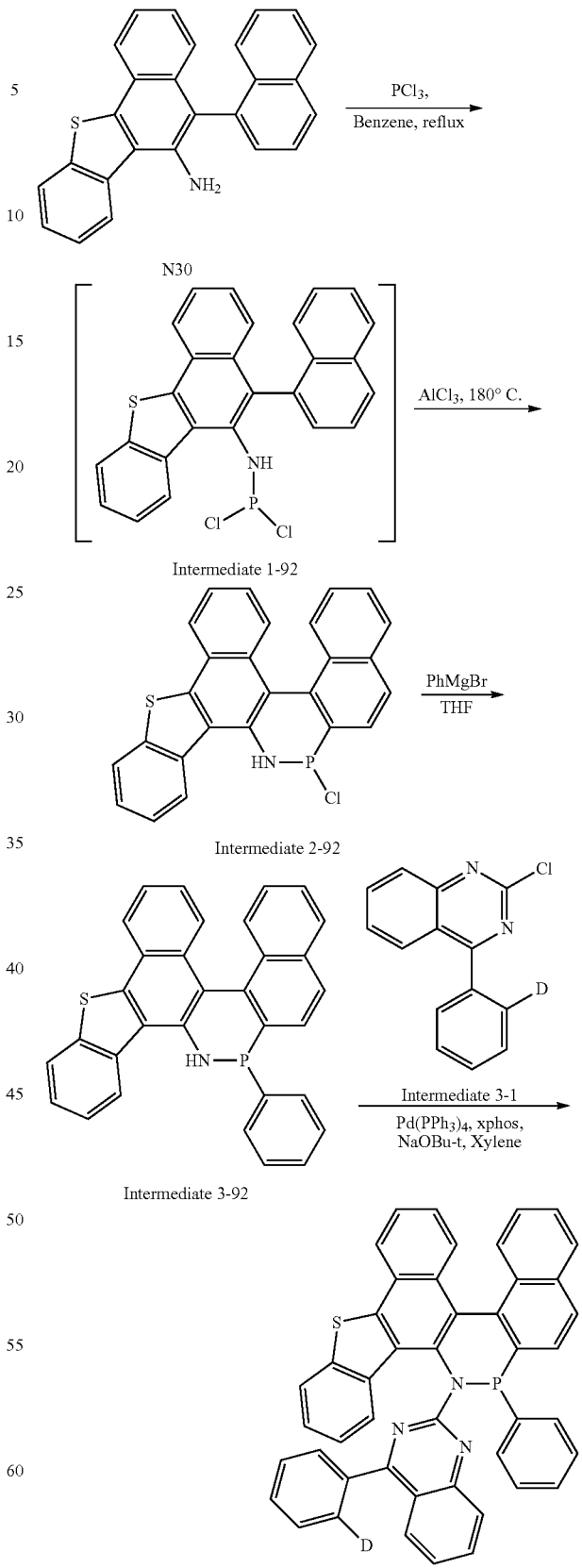

The compound 92 was prepared through a method comprising specifically the following steps.

Synthesis of compound N30: The synthesis process was the same as that for the intermediate 2-67, except that the raw material compound

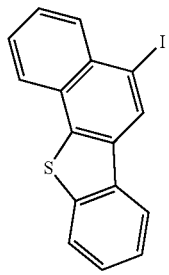 [SMILES: Ic1cc2c3ccccc3sc2c2ccccc12]

was used in place of the compound

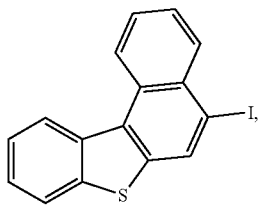 [SMILES: Ic1cc2sc3ccccc3c2c2ccccc12]

and the final yield was 26%. The synthesis route was shown below.

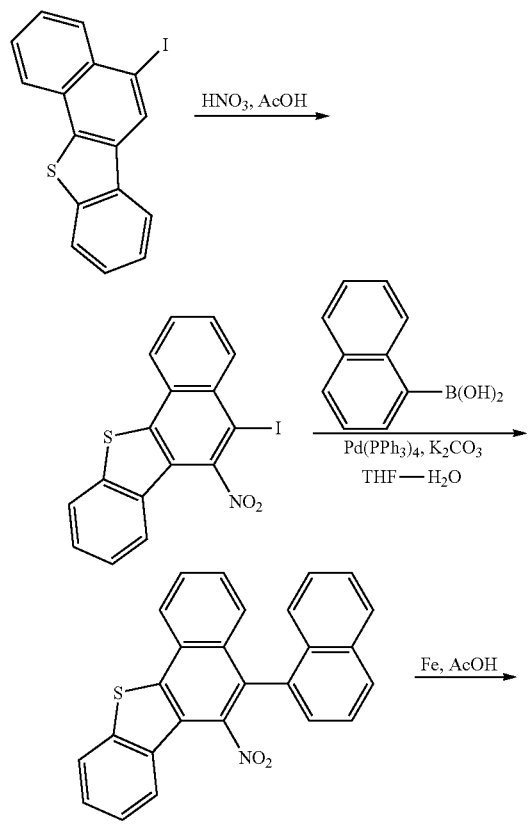

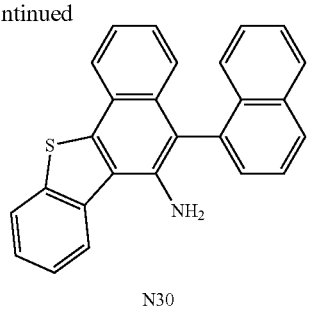

Synthesis of intermediate 2-92: To a three-neck flask, the compound N30 (75.1 g, 0.20 mol), and then benzene (500 mL) and anhydrous phosphorus trichloride (27.5 g, 0.2 mol) were added, and refluxed for 16 hrs under a nitrogen atmosphere. The reaction solution was cooled, rotary dried to remove the benzene, and then added with anhydrous aluminum trichloride (3.1 g, 0.02 mol). The reaction mixture was reacted at 180° C. for 5 hrs, cooled, and purified by column chromatography (PE:EA=5:1-3:1), to obtain the intermediate 2-92 (62.5 g, yield 71.1%).

Synthesis of intermediate 3-92: To a three-neck flask, the intermediate 2-92 (44.0 g, 0.10 mol), and then anhydrous tetrahydrofuran (300 mL) were added. Under a nitrogen atmosphere, the phenyl grignard reagent (150 mL, 0.30 mol) was added dropwise at 0° C. After addition, the system was stirred at room temperature for 12 hrs, refluxed for 2 hrs, cooled, poured into iced water (300 mL), and adjusted to a neutral pH with 5% hydrochloric acid. The reaction solution was extracted with dichloromethane (200 mL×2), and the organic phase was washed with saturated saline (200 mL), dried over sodium sulfate, and rotary dried to obtain a crude product (59 g). The crude product was recrystallized in diethyl ether:dichloromethane (volume ratio 1:1, 400 mL), to obtain the intermediate 3-92 (30.5 g, yield 63.3%).

Synthesis of compound 92: To a three-neck flask, the intermediate 3-92 (9.6 g, 0.020 mol), the intermediate 3-1 (7.2 g, 0.030 mol), sodium tert-butoxide (3.9 g, 0.040 mol), xphos (400 mg), and xylene (60 mL) were added. Tetrakis(triphenylphosphine)palladium (200 mg) was then added under a nitrogen atmosphere. Subsequently, the reaction was heated to 140° C. and stirred for 4 hrs under a nitrogen atmosphere. The reaction solution was cooled, and the organic phase was rotary dried. The residue was purified by column chromatography (PE:EA=8:1-4:1) to obtain a crude product (12.2 g) of the compound 92, which was beaten three times each in xylene and tetrahydrofuran (80 mL×6), to obtain the compound 92 (7.7 g, yield 56%).

Element analysis: ($C_{46}H_{27}DN_3PS$) calculated: C, 80.45; H, 4.26; N, 6.12; S, 4.67; found: C, 80.48; H, 4.26; N, 6.12; S, 4.65; HRMS (ESI) m/z ($M^+$): calculated: 686.1804; found: 686.1809.

Example 18

This example provides a route for synthesizing a fused polycyclic compound 95.

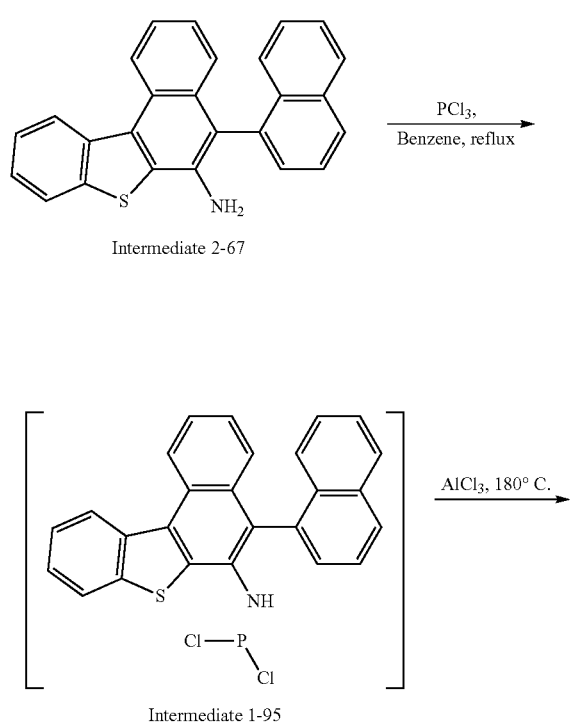

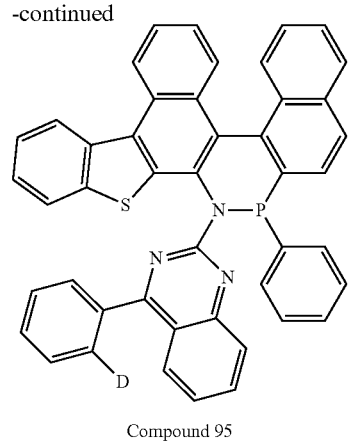

Compound 95

The compound 95 was prepared through a method comprising specifically the following steps.

Synthesis of intermediate 2-95: The synthesis method was the same as that for the intermediate 2-92, except that the intermediate 2-67 (72 g, 0.20 mol) was used in place of N30, to obtain the intermediate 2-95 (63.0 g, yield 71.8%).

Synthesis of intermediate 3-95: The synthesis method was the same as that for the intermediate 3-92, except that the intermediate 2-95 (43.9 g, 0.1 mol) was used in place of the intermediate 2-92, to obtain the intermediate 3-95 (29.4 g, yield 61.2%).

Synthesis of compound 95: The synthesis method was the same as that for the compound 92, except that the intermediate 3-95 (9.6 g, 0.02 mol) was used in place of the intermediate 2-95, to obtain the compound 95 (7.9 g, yield 57.8%).

Element analysis: ($C_{46}H_{27}DN_3PS$) calculated: C, 80.45; H, 4.26; N, 6.12; S, 4.67; found: C, 80.48; H, 4.25; N, 6.12; S, 4.68; HRMS (ESI) m/z (M+): calculated: 686.1804; found: 686.1811.

Example 19

This example provides a route for synthesizing a fused polycyclic compound 105.

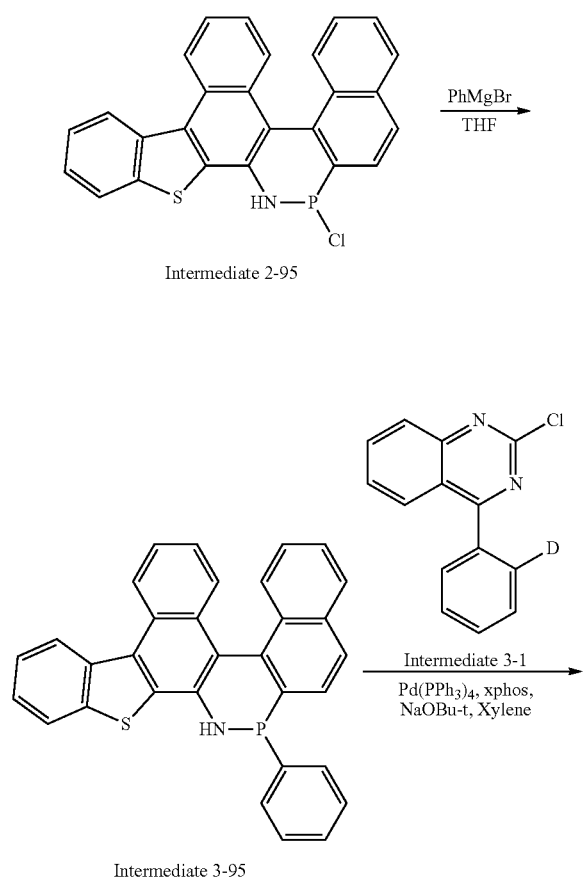

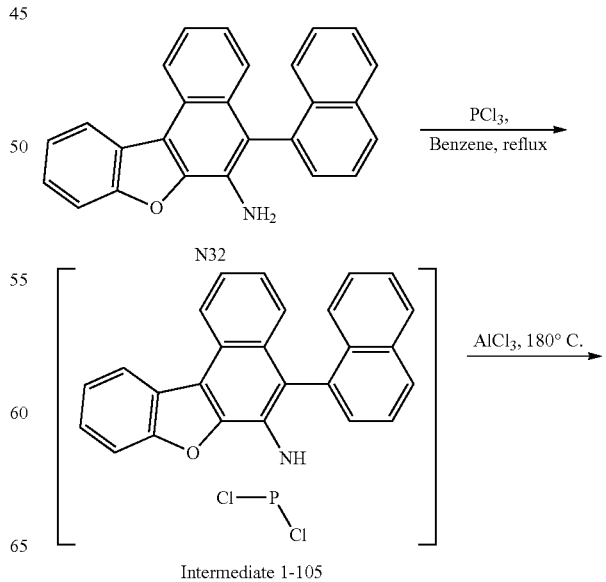

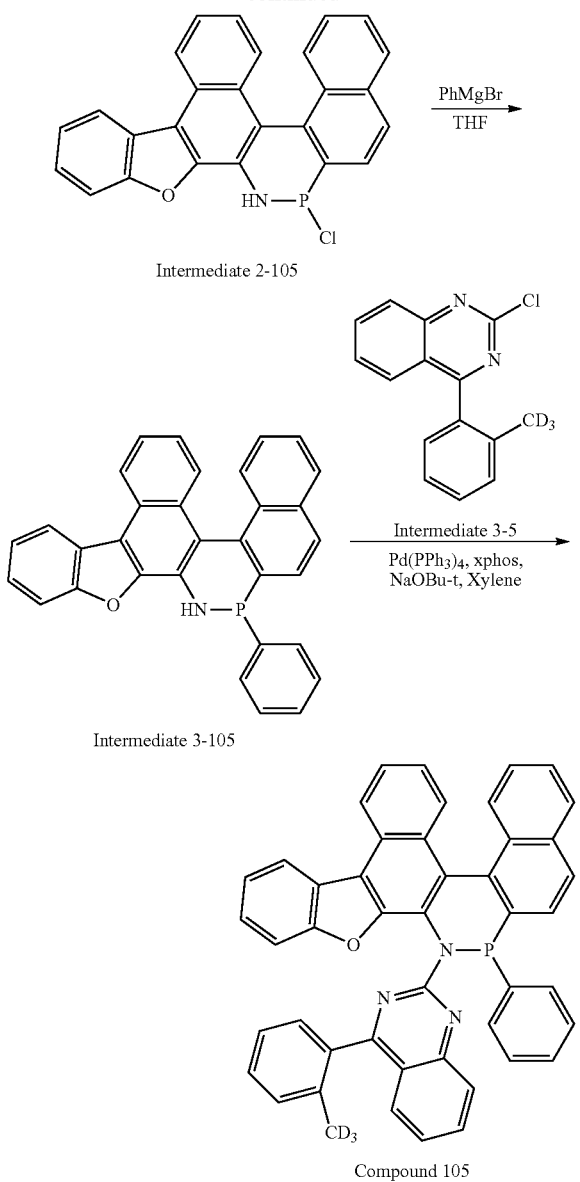

Intermediate 2-105

Intermediate 3-105

Compound 105

The compound 105 was prepared through a method comprising specifically the following steps.

Synthesis of compound N32: The synthesis method of the compound N32 was the same as that for the intermediate 2-67, except that the compound

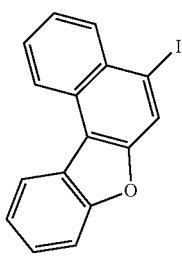 [SMILES: Ic1cc2oc3ccccc3c2c2ccccc12]

(0.2 mol) was used in place of the compound

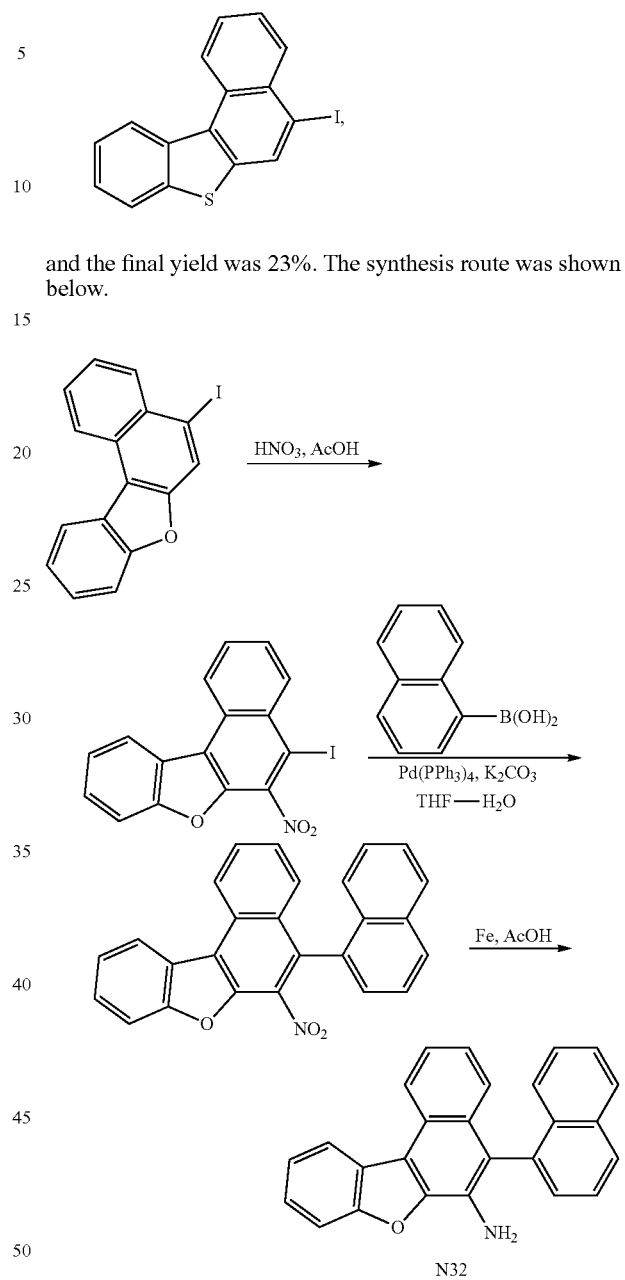

and the final yield was 23%. The synthesis route was shown below.

Synthesis of intermediate 2-105: The synthesis method was the same as that for the intermediate 2-92, except that the compound N32 (71.8 g, 0.20 mol) was used in place of the compound N30, to obtain the intermediate 2-105 (63.5 g, yield 75.1%).

Synthesis of intermediate 3-105: The synthesis method was the same as that for the intermediate 3-92, except that the intermediate 2-105 (42.3 g, 0.1 mol) was used in place of the intermediate 2-92, to obtain the intermediate 3-105 (28.4 g, yield 61.0%).

Synthesis of compound 105: The synthesis method was the same as that for the compound 92, except that the intermediate 3-105 (9.3 g, 0.02 mol) was used in place of the intermediate 2-105, to obtain the compound 105 (7.9 g, yield 57.8%).

Element analysis: ($C_{47}H_{27}D_3N_3PO$) calculated: C, 82.20; H, 4.84; N, 6.12; found: C, 82.24; H, 4.83; N, 6.11; HRMS (ESI) m/z (M+): calculated: 686.2315; found: 686.2321.

Example 20

This example provides a route for synthesizing a fused polycyclic compound 133.

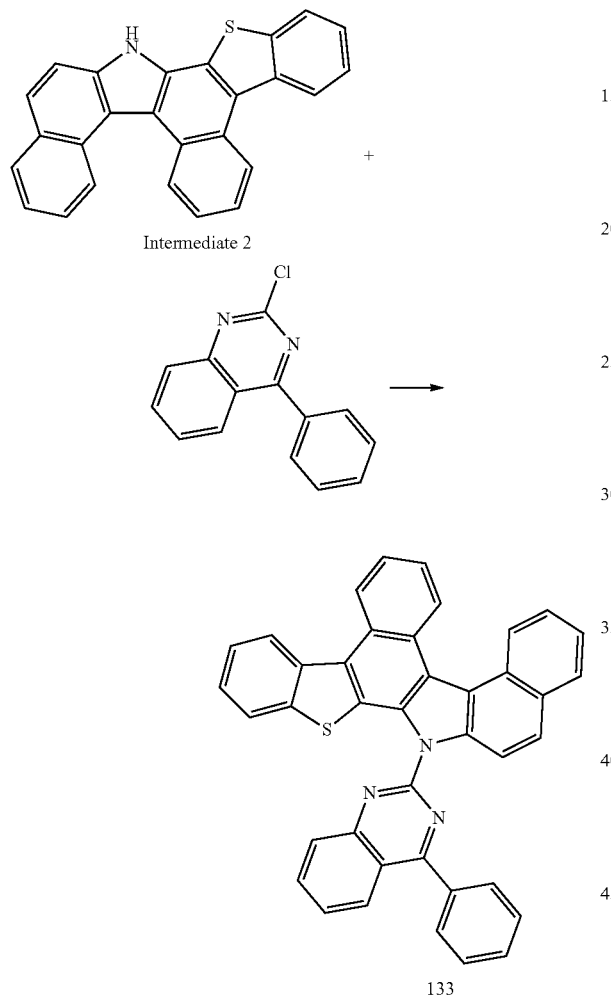

The preparation method of the compound 133 was the same as that for the compound 36, except that

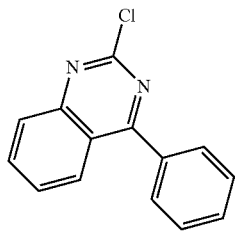 [SMILES: Clc1nc(-c2ccccc2)c2ccccc2n1]

was used in place of the intermediate 3-1, and the compound 133 was obtained with a yield of 66%.

Element analysis: $C_{40}H_{23}N_3S$ calculated: C, 83.16; H, 4.01; N, 7.27; S, 5.55; found: C, 83.19; H, 4.01; N, 7.25; S, 5.54; HRMS (ESI) m/z (M+): calculated: 577.1613; found: 577.1619.

Device Example 1

This example provides an organic light-emitting device, which includes, from bottom to top, an anode 1, a hole injection layer 2, a hole transport layer 3, a light emitting layer 4, an electron transport layer 5, an electron injection layer 6 and a cathode 7 stacked in sequence. The device is configured to have a particular structure of ITO/hole injection layer (HIL) (30 nm)/hole transport layer (HTL) (40 nm)/organic light-emitting layer (compound 10 doped with compound RD) (40 nm)/electron transport layer (ETL) (40 nm)/electron injection layer (EIL/LiF) (1 nm)/cathode (Al) (150 nm) as shown in FIG. 1.

In the organic light-emitting device, the material of the anode 1 is ITO.

The material of the hole injection layer 2 is the compound $HAT(CN)_6$ having a structure below:

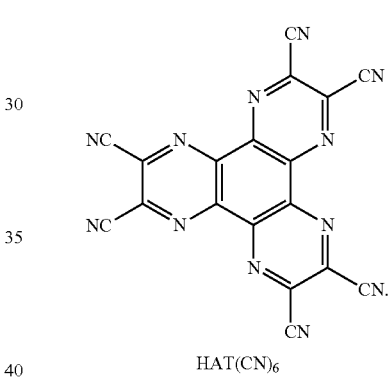

$HAT(CN)_6$

The material of the hole transport layer 3 is the compound NPB having a structure below:

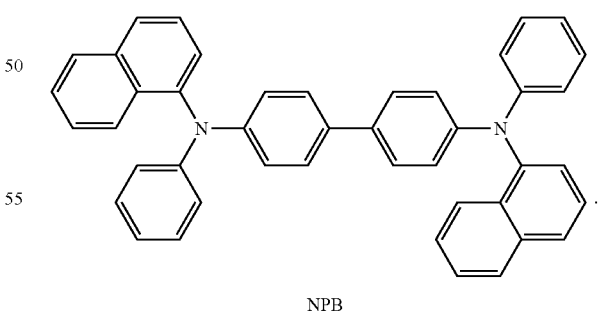

NPB

The organic light emitting layer 4 is formed by blending a host material and a guest material, where the host material is the compound 10, and the guest material is the compound RD; the host material and the guest material are blended at a weight ratio of 100:5; and the compound RD has a chemical structure shown below:

[Structure: RD]

The material of the electron transport layer 5 is the compound CBP having a structure below:

[Structure: CBP]

The material of the electron injection layer 6 is formed by the compound BCP having a structure below, blended with the electron injection material LiF, where BCP and LiF are blended at a weight ratio of 100:3:

[Structure: BCP]

The material of the cathode 7 is the metal Al.

The organic light emitting device was fabricated through a process comprising the following steps.

1) Cleaning of Substrate:

A glass substrate coated with an ITO transparent electrode was ultrasonically treated in a commercial detergent (Yokohama Chemical Technology (Changzhou) Co., Ltd., with an ethylene glycol solvent of ≤10 wt %, and triethanolamine of ≤1 wt %), rinsed in deionized water, ultrasonicated in a mixed solvent of acetone:ethanol (volume ratio 1:1) to remove the oil, baked in a clean environment to completely remove the moisture, and then cleaned with ultraviolet light and ozone.

2) Fabrication of Organic Layer and Cathode:

The glass substrate with the anode layer was placed in a vacuum chamber which was then evacuated to $1 \times 10^{-6}$ to $2 \times 10^{-4}$ Pa. $HAT(CN)_6$ was deposited, as a hole injection layer, onto the anode film, where the deposition rate was 0.1 nm/s, and the film thickness deposited was 30 nm.

A hole transport layer was deposited on the hole injection layer, where the deposition rate was 0.1 nm/s, and the film thickness deposited was 40 nm.

An organic light-emitting layer was deposited on the hole transport layer. The fabrication process was specifically as follows. A luminescent host material and guest material were deposited under vacuum by means of co-deposition, where the host material was deposited at a rate of 0.1 nm/s, the guest material was deposited at a rate of 0.005 nm/s, and the total film thickness deposited was 40 nm.

An electron transport layer was deposited on the organic light-emitting layer under vacuum, where the deposition rate was 0.1 nm/s, and the total film thickness deposited was 40 nm.

An electron injection layer was deposited on the electron transport layer under vacuum, where the deposition rate was 0.05 nm/s, and the total film thickness deposited was 1 nm.

Al was deposited on the electron injection layer, where the deposition rate was 0.1 nm/s, and the total film thickness deposited was 150 nm.

Device Example 2

This example provides an organic light-emitting device, which differs from the organic light-emitting device provided in Device Example 1 in that the host material in the light emitting layer is the compound 22.

Device Example 3

This example provides an organic light-emitting device, which differs from the organic light-emitting device provided in Device Example 1 in that the host material in the light emitting layer is the compound 26.

Device Example 4

This example provides an organic light-emitting device, which differs from the organic light-emitting device provided in Device Example 1 in that the host material in the light emitting layer is the compound 36.

Device Example 5

This example provides an organic light-emitting device, which differs from the organic light-emitting device provided in Device Example 1 in that the host material in the light emitting layer is the compound 37.

Device Example 6

This example provides an organic light-emitting device, which differs from the organic light-emitting device provided in Device Example 1 in that the host material in the light emitting layer is the compound 38.

Device Example 7

This example provides an organic light-emitting device, which differs from the organic light-emitting device provided in Device Example 1 in that the host material in the light emitting layer is the compound 39.

Device Example 8

This example provides an organic light-emitting device, which differs from the organic light-emitting device provided in Device Example 1 in that the host material in the light emitting layer is the compound 46.

Device Example 9

This example provides an organic light-emitting device, which differs from the organic light-emitting device provided in Device Example 1 in that the host material in the light emitting layer is the compound 47.

Device Example 10

This example provides an organic light-emitting device, which differs from the organic light-emitting device provided in Device Example 1 in that the host material in the light emitting layer is the compound 48.

Device Example 11

This example provides an organic light-emitting device, which differs from the organic light-emitting device provided in Device Example 1 in that the host material in the light emitting layer is the compound 49.

Device Example 12

This example provides an organic light-emitting device, which differs from the organic light-emitting device provided in Device Example 1 in that the host material in the light emitting layer is the compound 73.

Device Example 13

This example provides an organic light-emitting device, which differs from the organic light-emitting device provided in Device Example 1 in that the host material in the light emitting layer is the compound 67.

Device Example 14

This example provides an organic light-emitting device, which differs from the organic light-emitting device provided in Device Example 1 in that the host material in the light emitting layer is the compound 107.

Device Example 15

This example provides an organic light-emitting device, which differs from the organic light-emitting device provided in Device Example 1 in that the host material in the light emitting layer is the compound 92.

Device Example 16

This example provides an organic light-emitting device, which differs from the organic light-emitting device provided in Device Example 1 in that the host material in the light emitting layer is the compound 95.

Device Example 17

This example provides an organic light-emitting device, which differs from the organic light-emitting device provided in Device Example 1 in that the host material in the light emitting layer is the compound 105.

Device Example 18

This example provides an organic light-emitting device, which differs from the organic light-emitting device pro-vided in Device Example 1 in that the host material in the light emitting layer is the compound 133.

Comparative Example 1

This comparative example provides an organic light-emitting device, which differs from the organic light-emitting device provided in Device Example 1 in that the host material in the light emitting layer is the compound E-1.

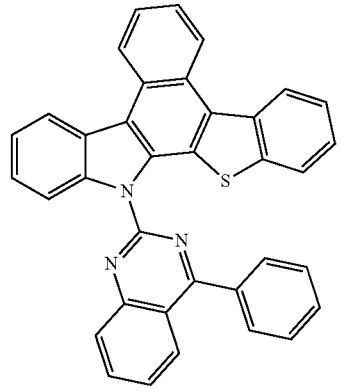

Compound E-1

Comparative Example 2

This comparative example provides an organic light-emitting device, which differs from the organic light-emitting device provided in Device Example 1 in that the host material in the light emitting layer is the compound E-2.

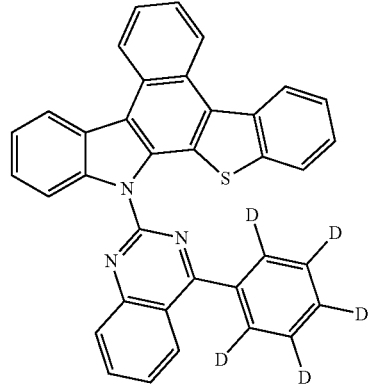

Compound E-2

Test Example 1

1. Determination of Thermal Deposition Temperature and Glass Transition Temperature Determination of thermal decomposition temperature of the compound: The thermal decomposition temperature (Td) of the material of the present invention was determined by using a thermogravimetric analyzer (TGA, US TA TGA55) in a temperature range from room temperature to 600° C. at a heating rate of 10° C./min, under nitrogen atmosphere. A temperature at which 5 wt % loss occurs is defined as the decomposition temperature.

Determination of glass transition temperature of the compound: The glass transition temperature (Tg) of the material according to the present invention was tested by differential scanning calorimetery (DSC, US TA DSC250) in a temperature range from room temperature to 600° C. at a heating rate of 10° C./min and a cooling rate of 10° C./min under nitrogen atmosphere, where two cycles of heating and cooling were performed.

2. Test of LUMO and HOMO Level

The HOMO and LUMO level of the material according to the present invention was tested by cyclic voltammetry (CV, CHI-600E from Shanghai Chenhua Instrument Co., Ltd.) using an electrochemical workstation with platinum (Pt) as a counter electrode and silver/silver chloride (Ag/AgCl) as a reference electrode. Under a nitrogen atmosphere, the test was carried out at a scan rate of 100 mV/s in an electrolyte solution containing 0.1 M tetrabutylammonium hexafluorophosphate in dichloromethane, and the potential was calibrated by ferrocene, in which the potential of ferrocene was set to an absolute energy level under vacuum of –4.8 eV:

$$HOMO = -[E_{onset}^{on} - E_{Fc|Fc+} + 4.8]eV$$

$$LUMO = -[E_{onset}^{red} - E_{Fc|Fc+} + 4.8]eV$$

Test of triplet energy level: Toluene was used as a solvent, the compound to be tested was formulated into a solution (with a concentration of $2*10^{-5}$ mol/L), and the solution was tested at –78° C. using a fluorescence spectrophotometer (Hitachi F-4600). $E_{T1}$ (eV) represents the triplet energy level of the compound, which is calculated using the formula below: $E_{T1}=1240/\lambda$ where $\lambda$ is the shortest ultraviolet/visible absorption wavelength.

Figure 2:
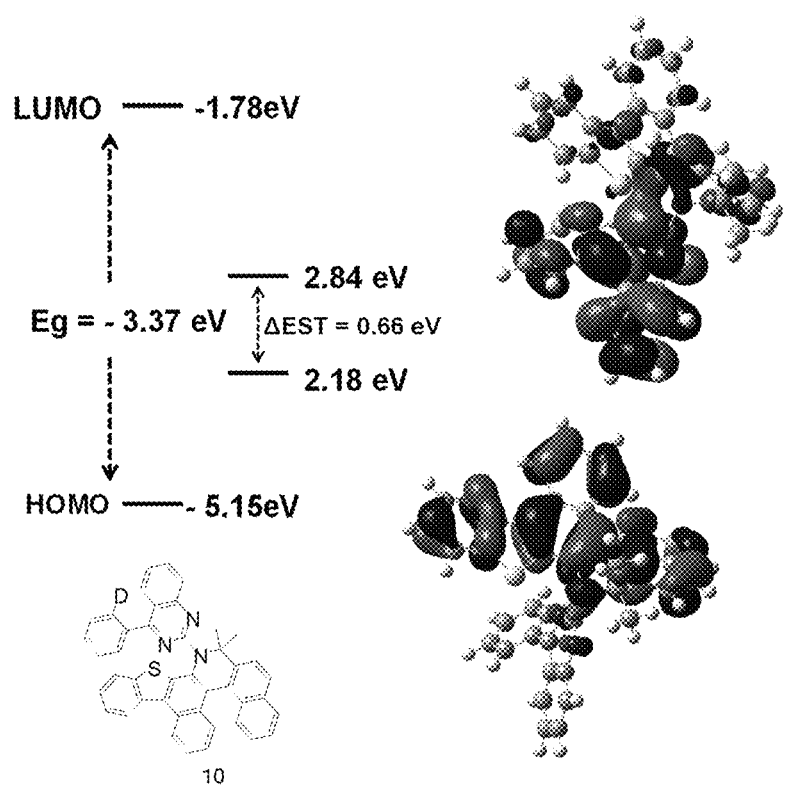
FIG. 2 compares the theoretical calculation results of the HOMO level, the LUMO level, and the singlet-triplet energy difference ΔEst of the compound 10 of the present invention.

The test results are shown in Tables 1 and 2. In FIG. 2, $E_g$(eV) represents the difference between the HOMO and LUMO level.

The results shown in Tables 1 and 2 indicate that the fused polycyclic compound provided in the present invention has a high thermal decomposition temperature, which ensures that the host material formed therefrom can maintain excellent thermal stability in the device, making the device unlikely to deteriorate due to decomposition during the fabrication process. The HOMO level and LUMO level of the fused polycyclic compound provided in the present invention are matched with the adjacent transport layer, so that the OLED device has a small driving voltage. In addition, the fused polycyclic compound provided in the present invention has a high singlet energy level, ensuring the efficient energy transfer from the host material to the guest material.

Test Example 2

Instruments: The current, voltage, brightness, and lifetime of the device were tested synchronously using PR 650 scanning spectroradiometer and Keithley K 2400 digital source meter.

Test conditions: current density 10 mA/cm$^2$; temperature 25° C.

The organic light-emitting devices provided in Device Examples 1-18 and Comparative Examples 1-2 were tested. The results are shown in Table 3.

TABLE 1

| | Compound | | | | | | | | | |
|---|---|---|---|---|---|---|---|---|---|---|
| | 10 | 22 | 26 | 36 | 37 | 38 | 39 | 46 | 47 | 48 |
| $T_d$ (° C.) | 396 | 396 | 385 | 386 | 387 | 386 | 388 | 388 | 389 | 390 |
| $T_g$ (° C.) | 123 | 122 | 133 | 139 | 136 | 137 | 138 | 140 | 141 | 139 |
| HOMO (eV) | −5.3 | −5.3 | −5.3 | −5.1 | −5.1 | −5.2 | −5.2 | −5.1 | −5.2 | −5.2 |
| LUMO (eV) | −1.9 | −1.8 | −2.0 | −2.2 | −2.2 | −2.2 | −2.2 | −2.2 | −2.2 | −2.1 |
| $E_{T1}$ (eV) | 2.08 | 2.09 | 2.12 | 2.21 | 2.19 | 2.20 | 2.19 | 2.18 | 2.18 | 2.18 |

TABLE 2

| | Compound | | | | | | | |
|---|---|---|---|---|---|---|---|---|
| | 49 | 73 | 67 | 107 | 92 | 95 | 105 | 133 |
| $T_d$ (° C.) | 392 | 367 | 374 | 373 | 370 | 371 | 370 | 380 |
| $T_g$ (° C.) | 138 | 130 | 131 | 123 | 122 | 126 | 127 | 136 |
| HOMO (eV) | −5.1 | −5.2 | −5.1 | −5.1 | −5.1 | −5.1 | −5.1 | −5.2 |
| LUMO (eV) | −2.2 | −2.0 | −2.2 | −2.0 | −2.0 | −2.1 | −2.1 | −2.2 |
| $E_{T1}$ (eV) | 2.17 | 2.11 | 2.12 | 2.07 | 2.13 | 2.12 | 2.06 | 2.18 |

TABLE 3

| Device Example | Host material (compound) | Voltage/V | Current density/ mA/cm² | Current efficiency/ cd/A | Chrominance/ CIE (X, Y) | Lifetime/hr |
|---|---|---|---|---|---|---|
| 1 | 10 | 4.3 | 10 | 42 | (0.66, 0.31) | 131 |
| 2 | 22 | 4.4 | 10 | 43 | (0.66, 0.31) | 132 |
| 3 | 26 | 4.3 | 10 | 44 | (0.67, 0.31) | 130 |
| 4 | 36 | 4.2 | 10 | 46 | (0.68, 0.31) | 163 |
| 5 | 37 | 4.2 | 10 | 45 | (0.68, 0.31) | 160 |
| 6 | 38 | 4.3 | 10 | 47 | (0.68, 0.31) | 165 |
| 7 | 39 | 4.4 | 10 | 44 | (0.68, 0.31) | 162 |
| 8 | 46 | 4.3 | 10 | 43 | (0.68, 0.30) | 148 |
| 9 | 47 | 4.3 | 10 | 42 | (0.67, 0.31) | 146 |
| 10 | 48 | 4.4 | 10 | 44 | (0.68, 0.31) | 147 |
| 11 | 49 | 4.4 | 10 | 42 | (0.68, 0.31) | 159 |
| 12 | 73 | 4.3 | 10 | 41 | (0.67, 0.31) | 129 |
| 13 | 67 | 4.3 | 10 | 38 | (0.63, 0.31) | 134 |
| 14 | 107 | 4.4 | 10 | 40 | (0.67, 0.31) | 132 |
| 15 | 92 | 4.4 | 10 | 40 | (0.64, 0.31) | 134 |
| 16 | 95 | 4.3 | 10 | 38 | (0.67, 0.31) | 131 |
| 17 | 105 | 4.3 | 10 | 40 | (0.67, 0.31) | 128 |
| 18 | 133 | 4.4 | 10 | 40 | (0.67, 0.31) | 130 |
| Comparative Example 1 | E-1 | 4.3 | 10 | 37 | (0.66, 0.31) | 127 |
| Comparative Example 2 | E-2 | 4.4 | 10 | 36 | (0.66, 0.31) | 113 |

The organic light-emitting devices provided in Device Examples 1-18 and Comparative Examples 1-2 were tested. The results are shown in Table 3. Compared with the device provided in the comparative examples, the OLED devices provided in the examples of the present invention has lower operating voltage, higher current efficiency, and longer lifetime, indicating that the fused polycyclic compound provided in the present invention, when used as a luminescent host material in an OLED device, can greatly improve the luminescence efficiency, reduce the driving voltage, extend the lifetime, and increase the performance of the OLED device.

Notably, the inventors find through research that when the phenyl ring A in the structure of the fused polycyclic compound provided in the present invention is not attached, at positions 1 and 2, 2 and 3, or 3 and 4, to

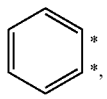

to form a fused ring sharing the same side, the current efficiency and lifetime of the device are seriously affected.

In the structure of the compound of General Formula I provided in the present invention, when some of the substituents $R^{15}$-$R^{23}$ are a deuterium-containing substituent, the current efficiency and lifetime of the device are superior as compared with the case where all of $R^{15}$-$R^{23}$ are hydrogen. Further, in the structure of the fused polycyclic compound of the present invention, when T is selected from $NR^{24}$, S, O, $BR^{24}$, $PR^{24}$, and $CR^{24}$, the OLED device also achieves a superior luminescence efficiency and lifetime. Notably, by using the compound of General Formula I where $T^1$ and $T^2$ are a linkage, and $T^3$ is S, the improvement on the lifetime and current efficiency of the device are the most notable, and the chrominance becomes more pure. When $R^{15}$-$R^{23}$ are selected from a deuterium substituent, the effect is much better than the case when they are a deuterated methyl substituent. Moreover, the inventors find through long-term research that the position of deuterium substitution also has an important impact on the lifetime of the device. The deuterium substitution on the ortho-para position of the phenyl ring has a significant improvement on the lifetime of the device.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:
1. A fused polycyclic compound, having a structure shown below:

General Formula IV

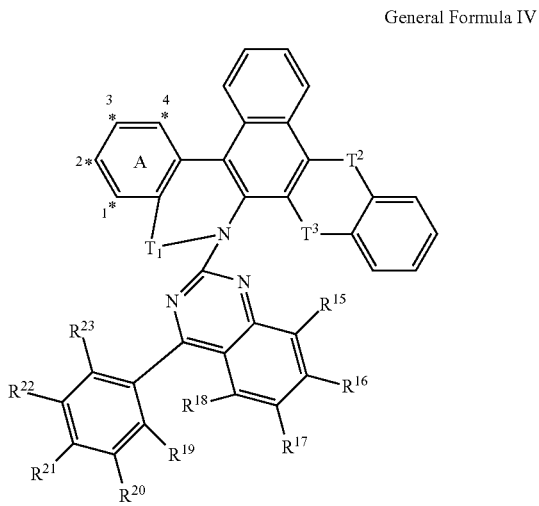

wherein the phenyl ring A is attached to

at positions 1 and 2, positions 2 and 3, or positions 3 and 4 to form a fused ring sharing the same side, in which "*" and

\*
\*

" " denotes the points of attachment;

T$^1$ is independently selected from NR$^{24}$, S, O, BR$^{24}$, PR$^{24}$, and C(R$^{24}$)$_2$, in which R$^{24}$ is the same or different, and is each independently selected from methyl, deuterated methyl, phenyl, deuterated phenyl, biphenylyl, deuterated biphenylyl, naphthalenyl, and deuterated naphthalenyl;

at least one of T$^2$ and T$^3$ is a single bond, when T$^2$ is a single bond, T$^3$ is S or O, and when T$^3$ is a single bond, T$^2$ is S or O; and R$^{15}$-R$^{23}$ are the same or different, and are each independently selected from hydrogen, deuterium, methyl, deuterated methyl, phenyl, deuterated phenyl, and deuterated methyl substituted phenyl; wherein at least one of R$^{15}$-R$^{23}$ is selected from deuterium, deuterated methyl, deuterated phenyl, and deuterated methyl substituted phenyl.

2. The fused polycyclic compound according to claim 1, wherein at least one of R$^{19}$, R$^{21}$, and R$^{23}$ is one selected from deuterium, deuterated methyl, deuterated phenyl, and deuterated methyl substituted phenyl.

3. The fused polycyclic compound according to claim 1, wherein when T$^2$ is a single bond, T$^3$ is S or O.

4. The fused polycyclic compound according to claim 1, having any one of the molecular structures shown below:

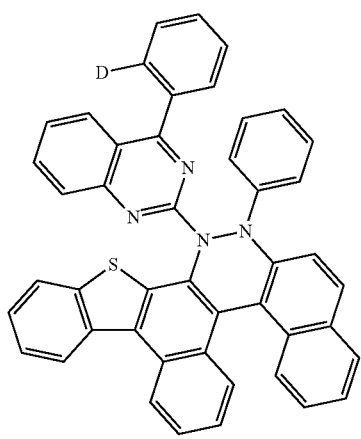

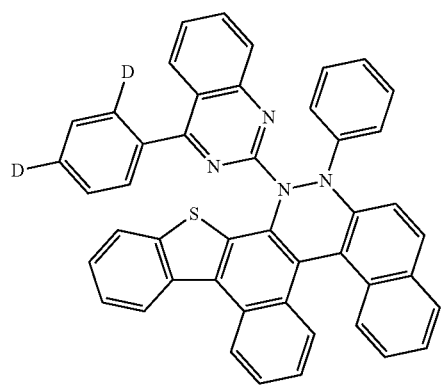

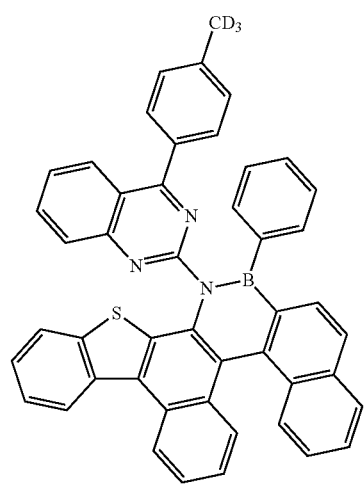

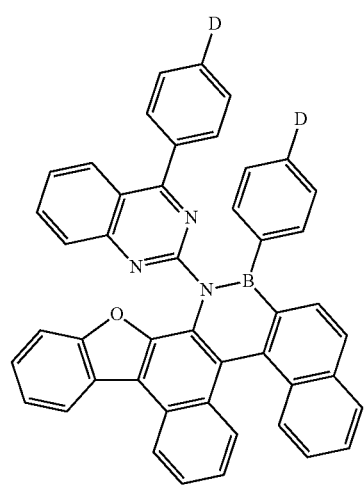

99
-continued
8
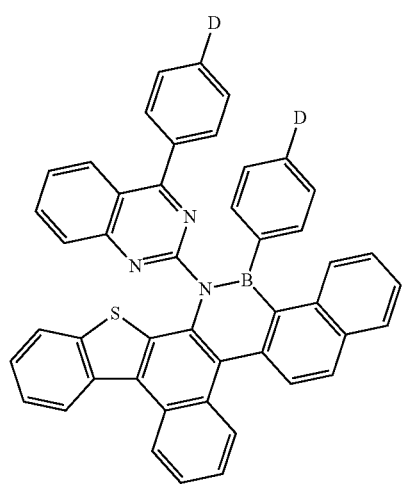
9
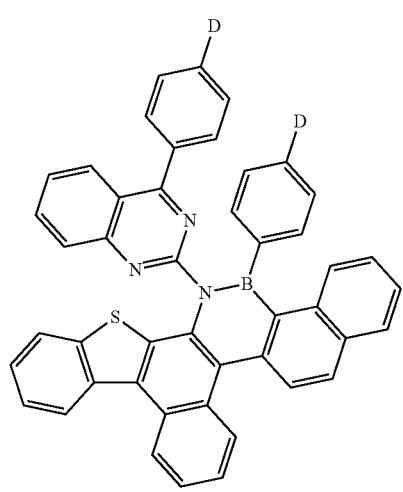
10
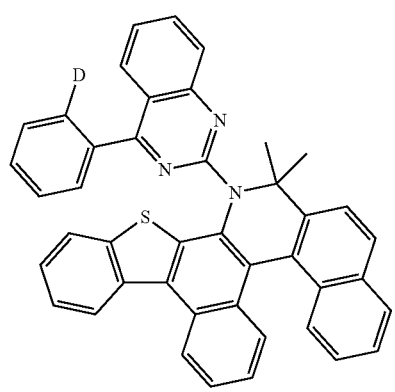
100
-continued
11
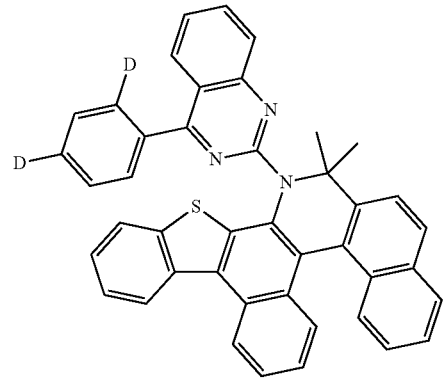
12
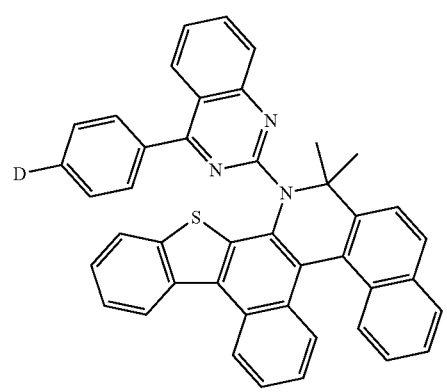
13
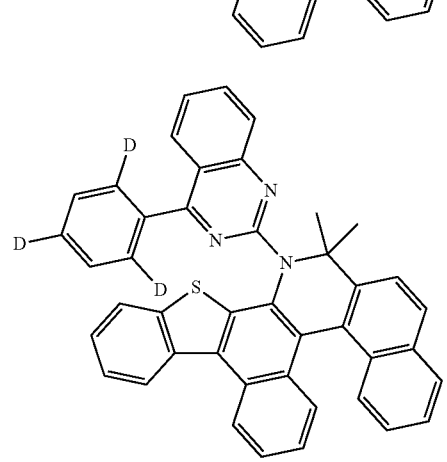
18
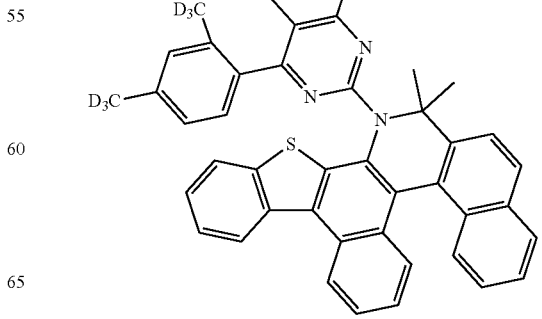

101
-continued
19
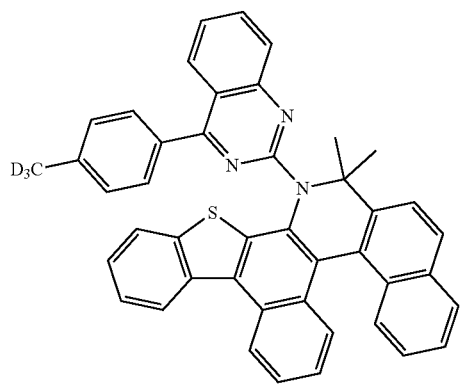
20
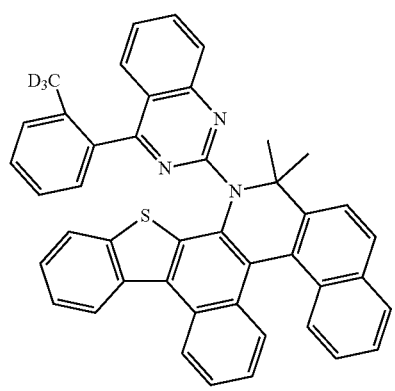
22
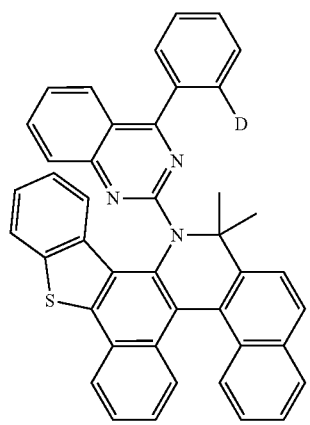
23
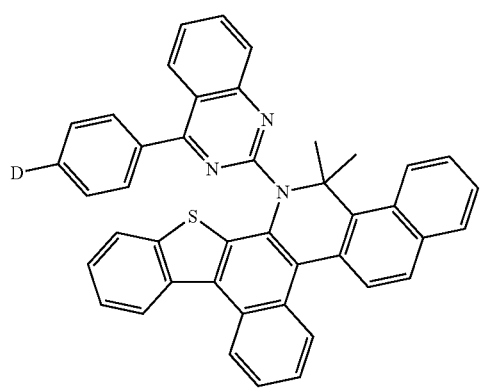
102
-continued
24
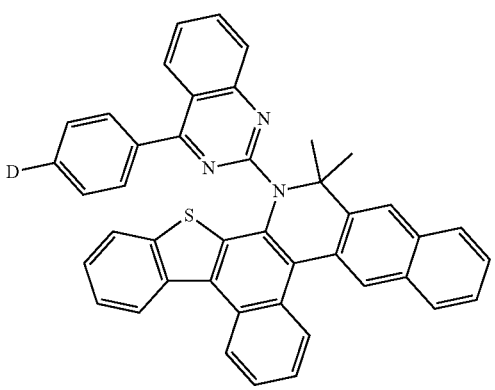
25
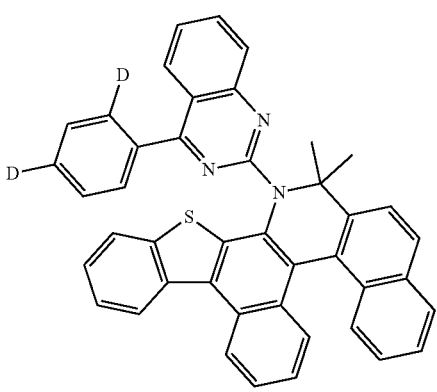
26
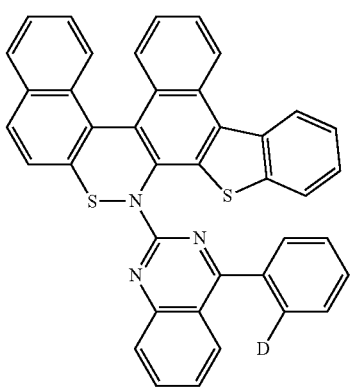
27
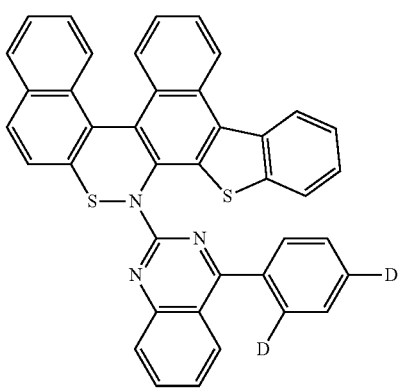

28
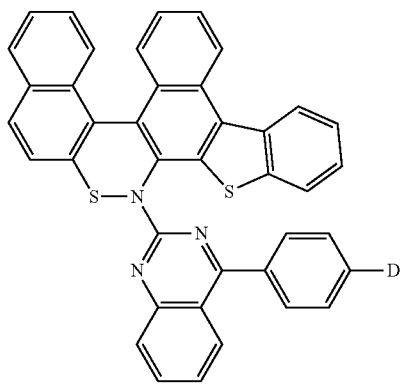
29
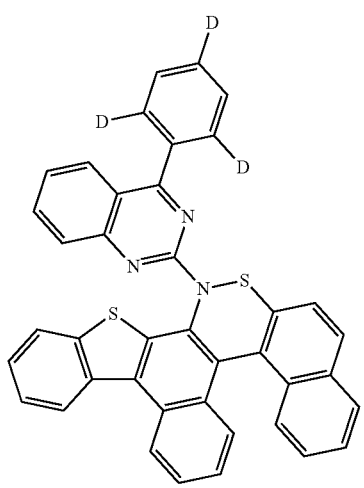
30
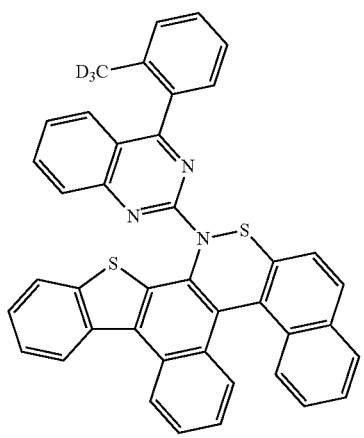
31
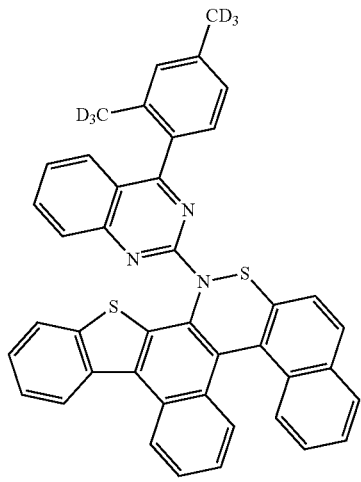
32
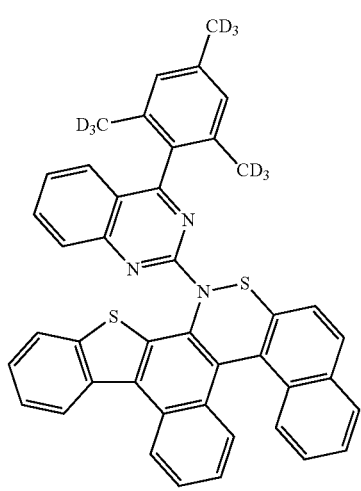
33
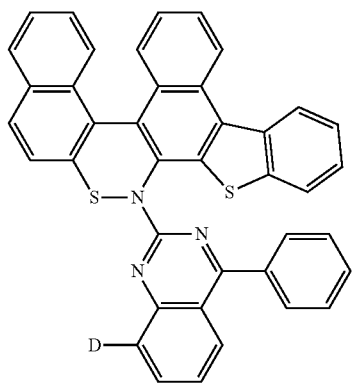

105
-continued
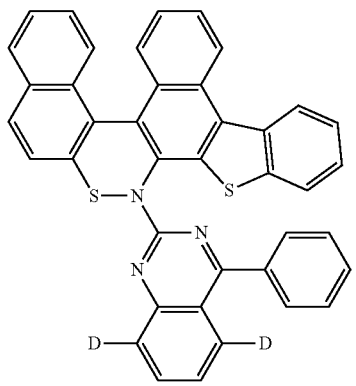
34
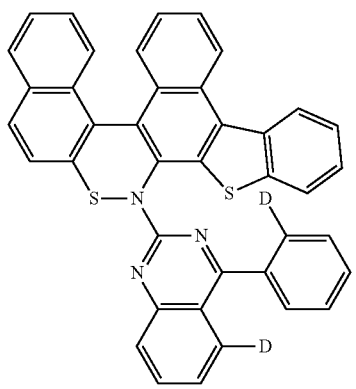
35
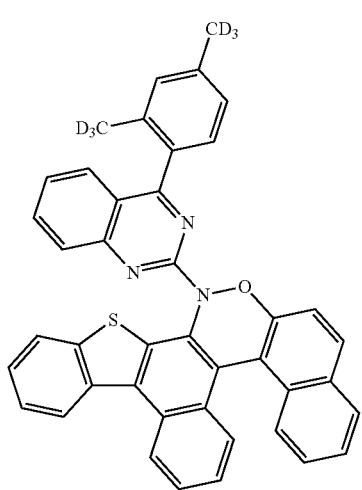
41
106
-continued
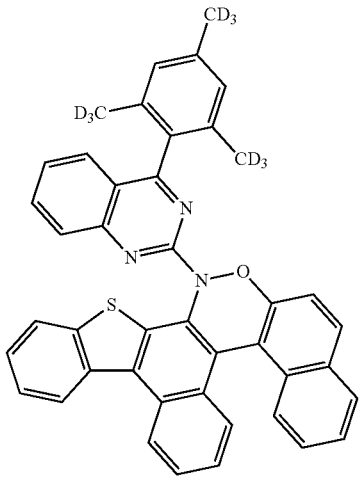
42
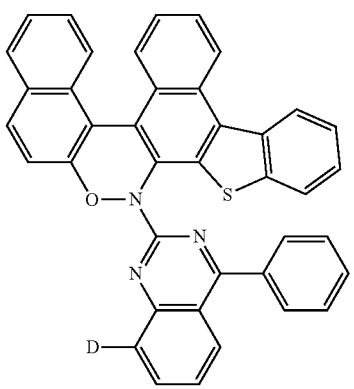
43
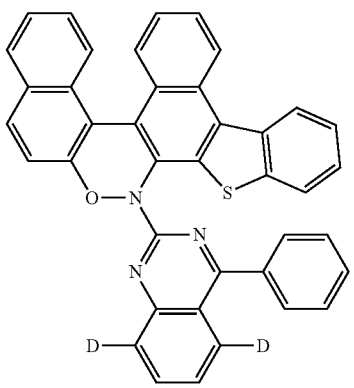
44
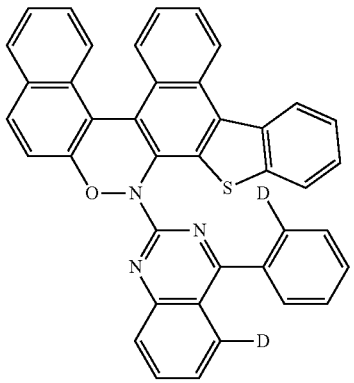
45

107
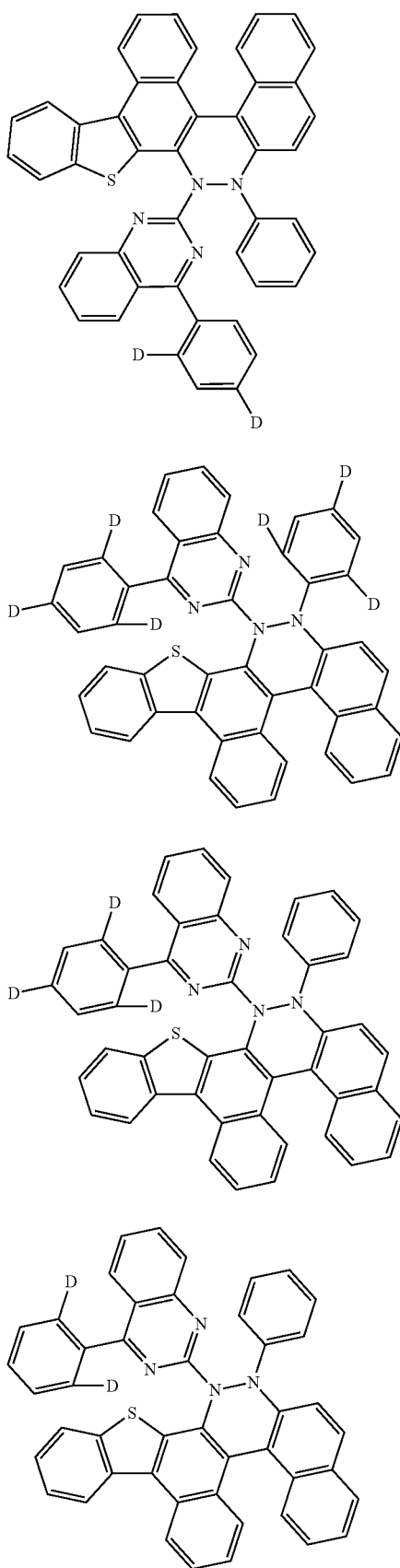
108
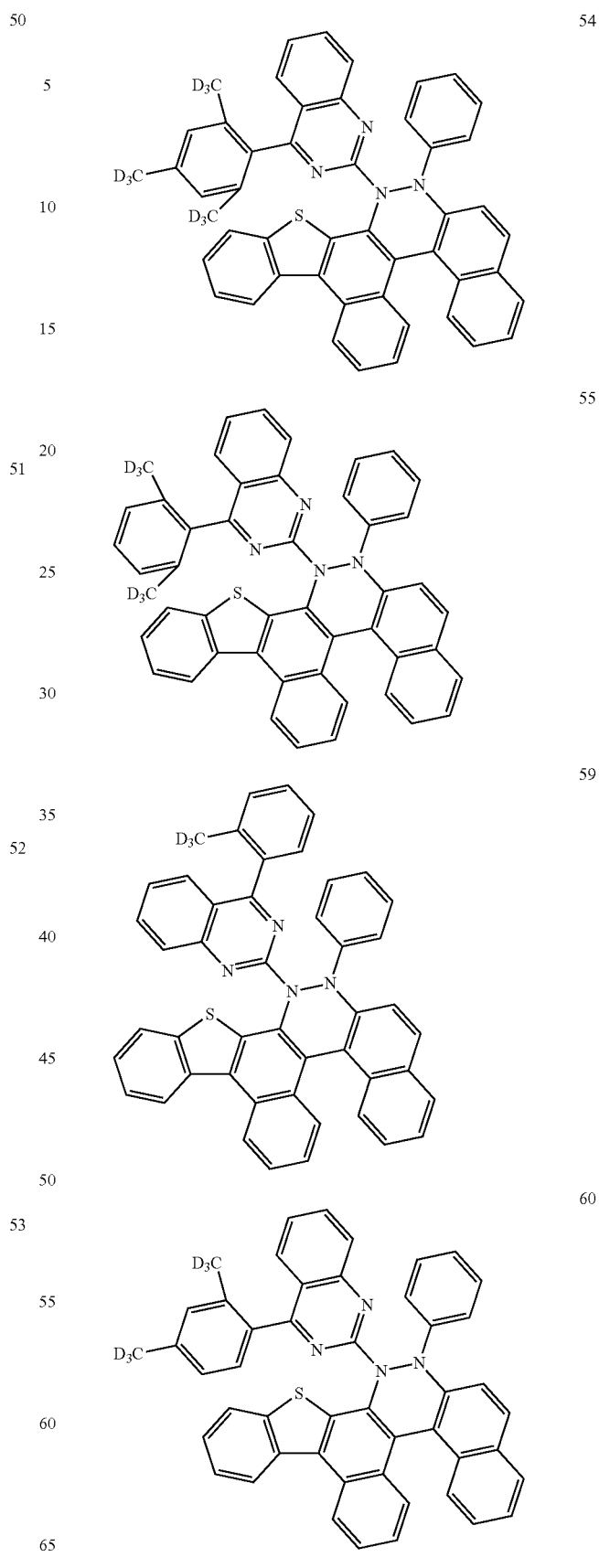

61
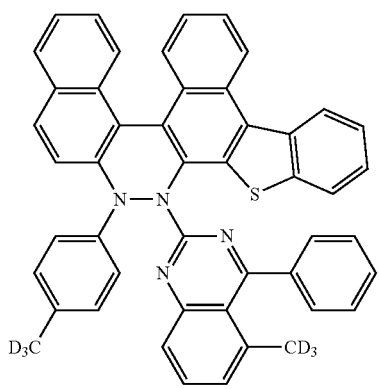
62
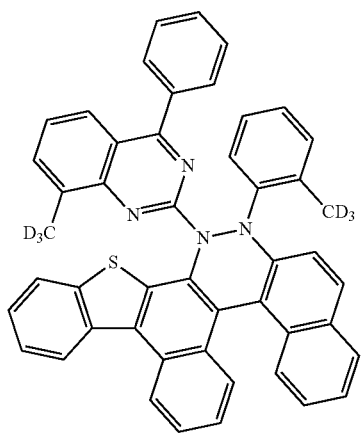
63
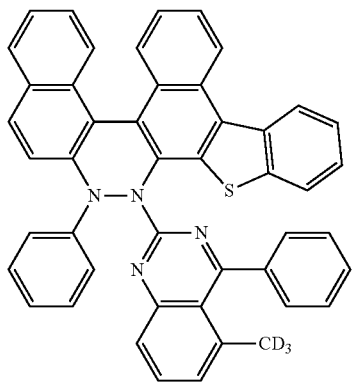
64
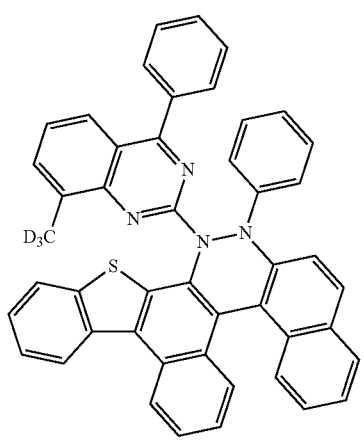
65
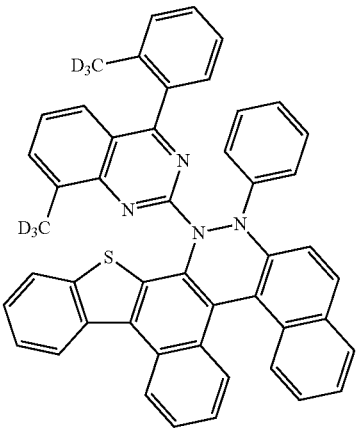
66
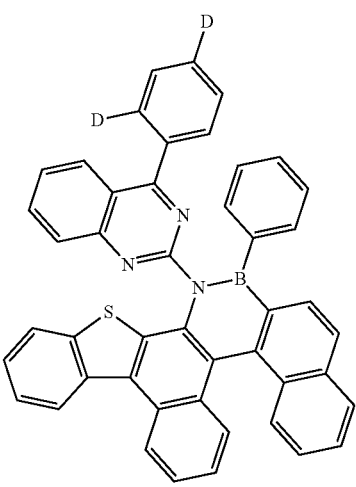
67
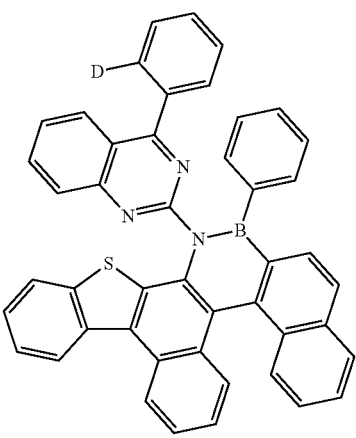

68
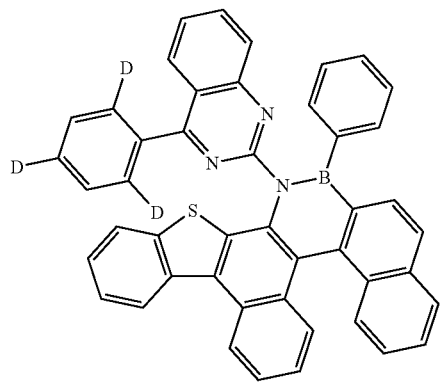
69
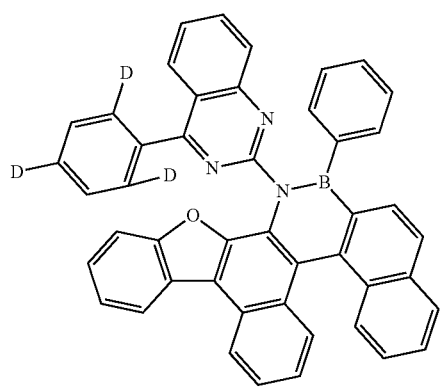
70
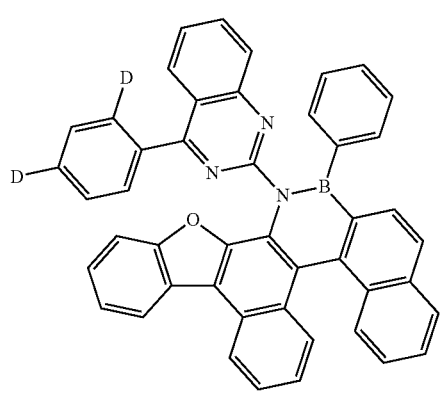
71
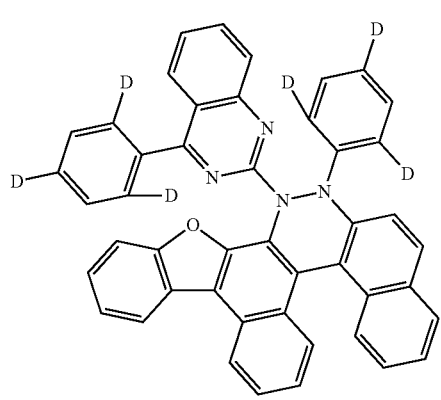
72
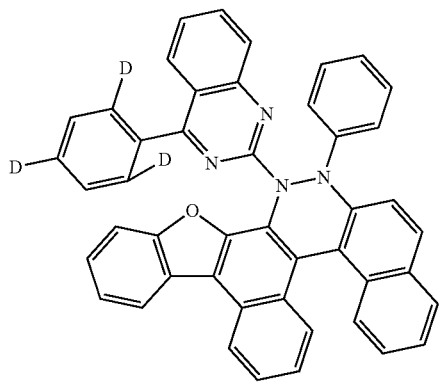
73
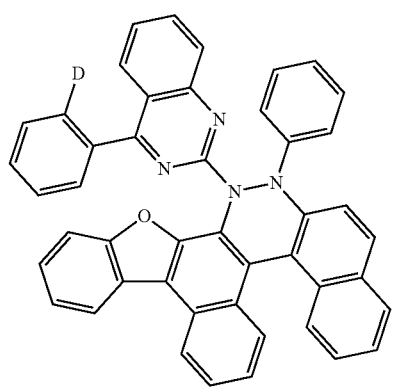
74
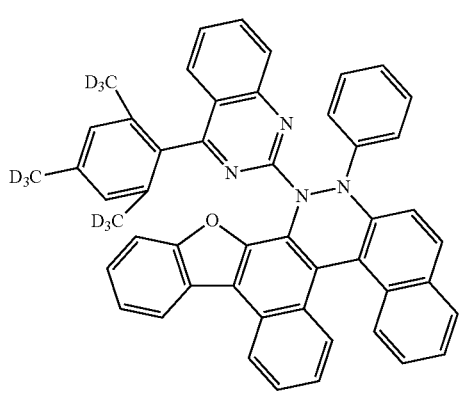
75
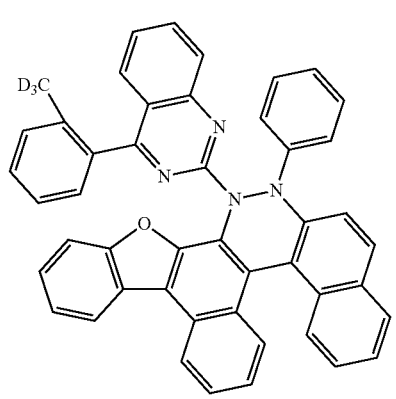

76
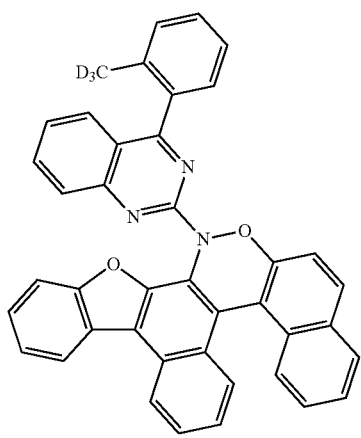
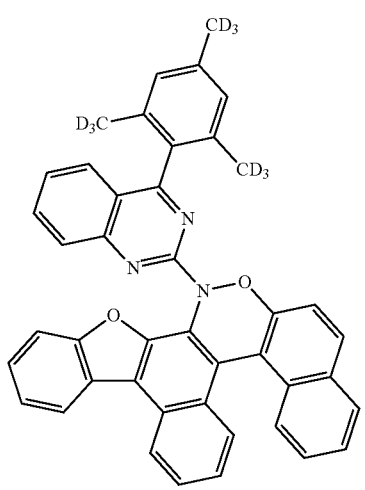
78
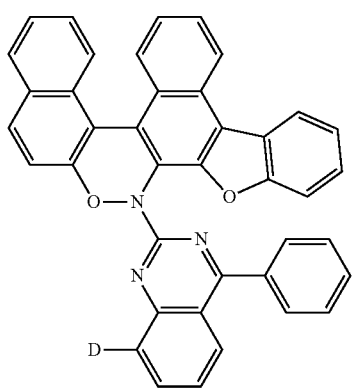
79
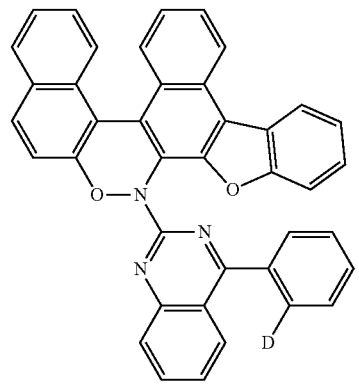
80
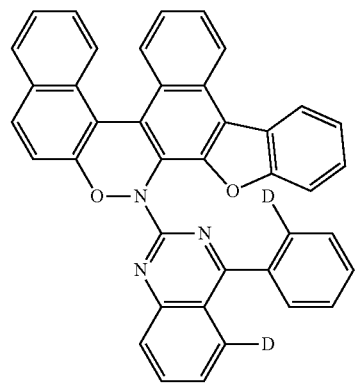
83
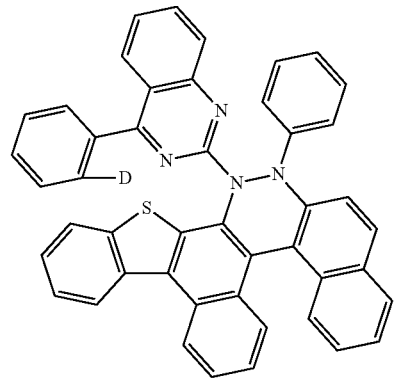
84
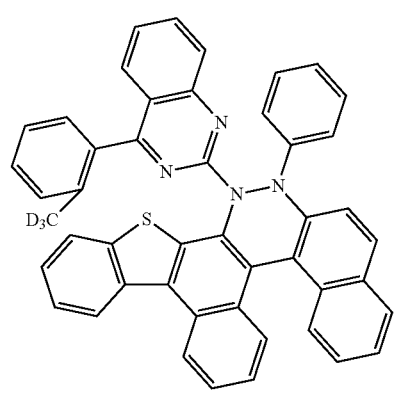

-continued
85
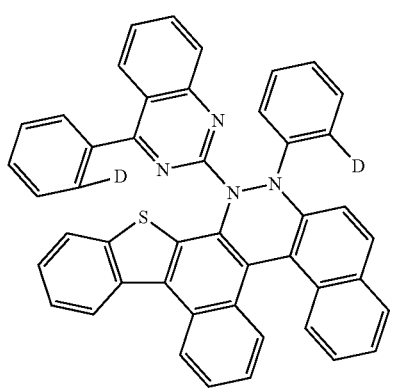
86
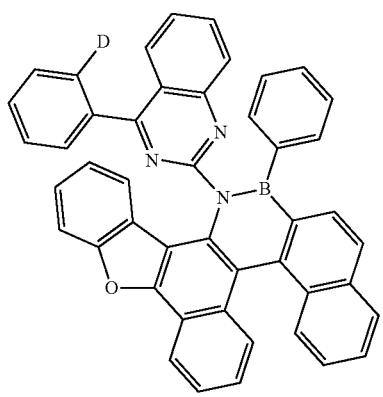
87
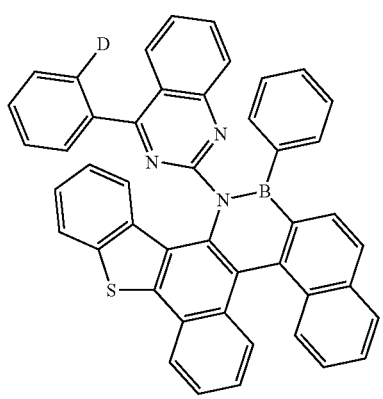
88
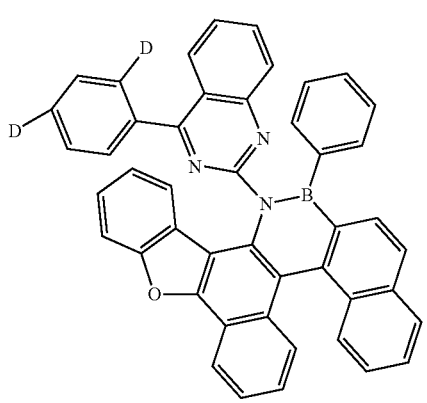
-continued
89
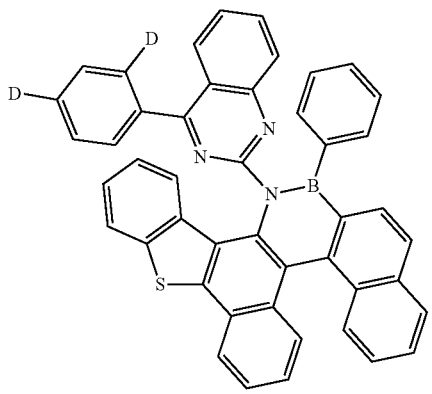
90
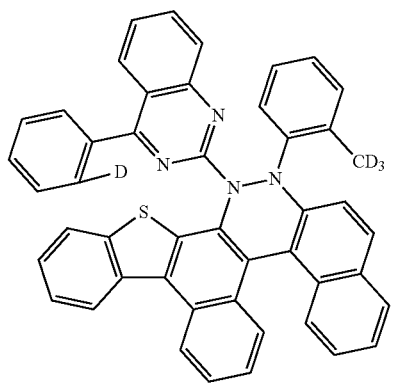
91
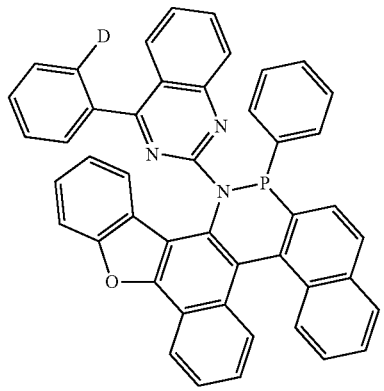
92
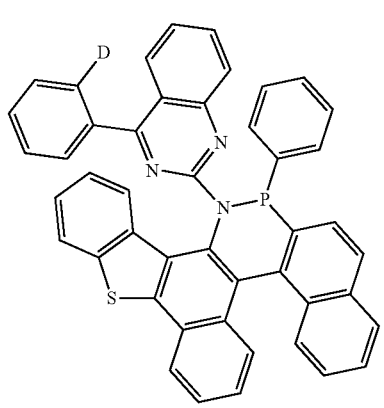

93
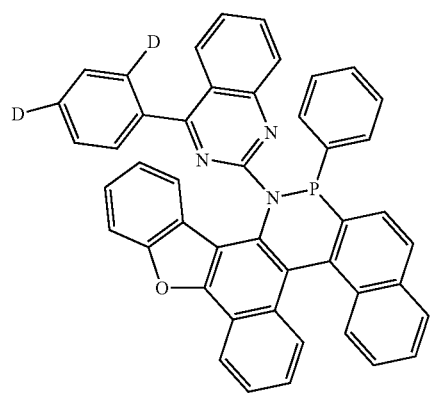
94
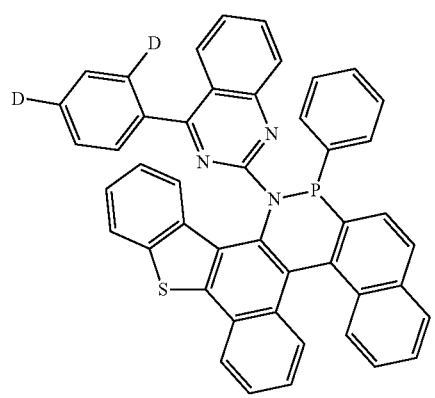
95
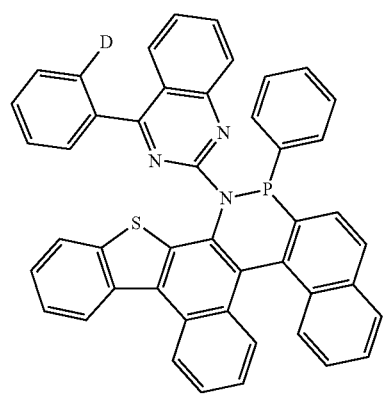
96
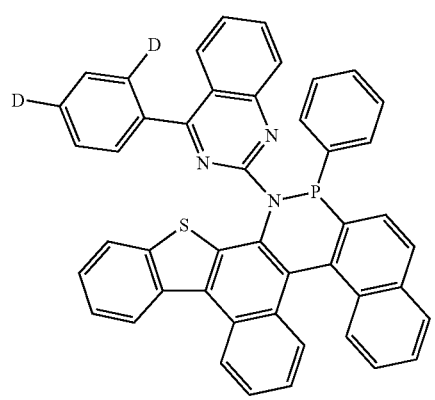
97
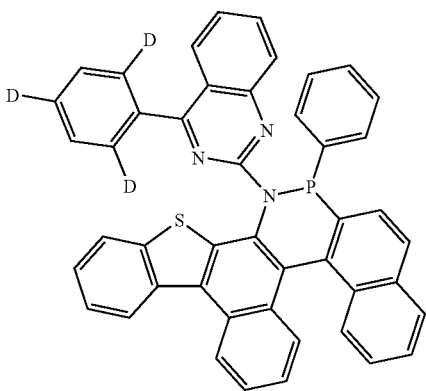
98
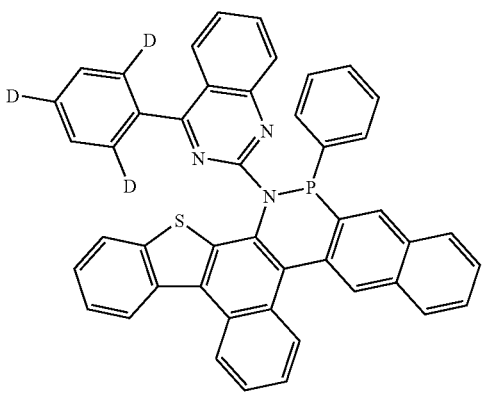
99
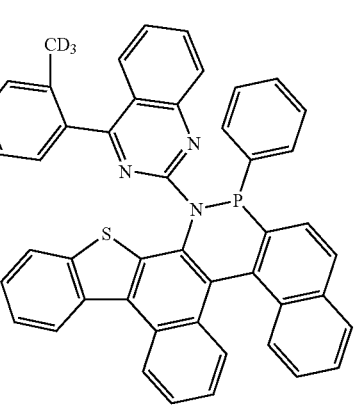
100
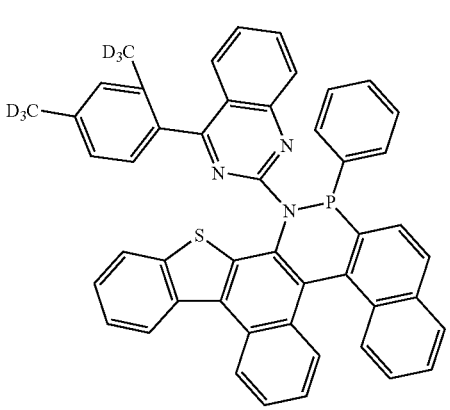

-continued
101 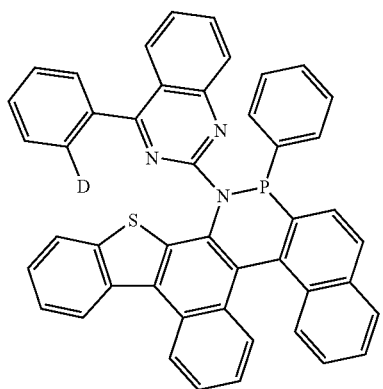
102 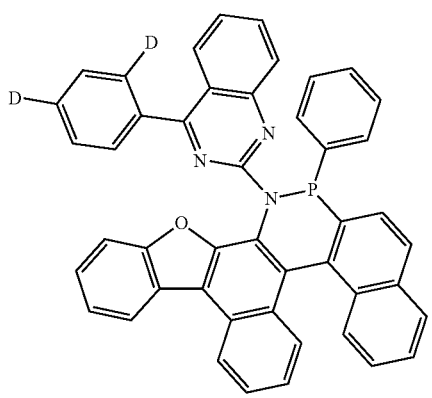
103 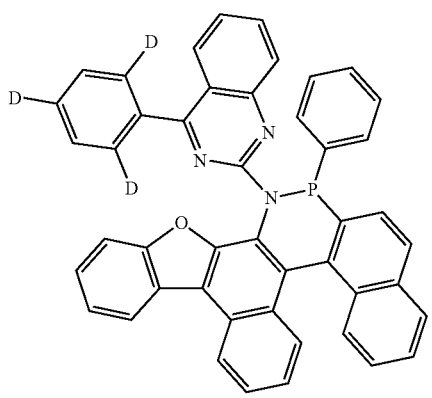
104 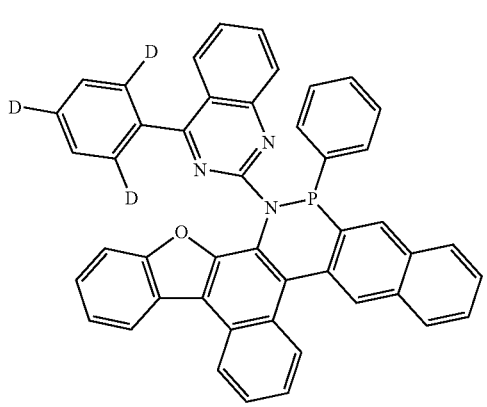
-continued
105 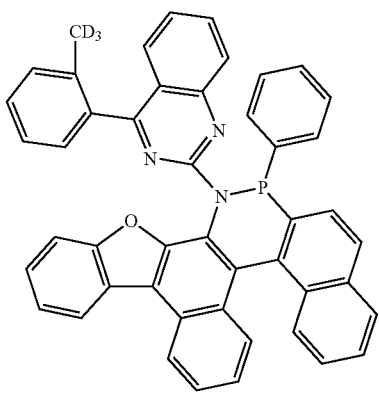
106 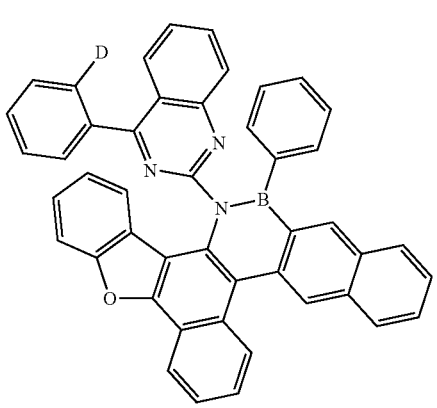
107 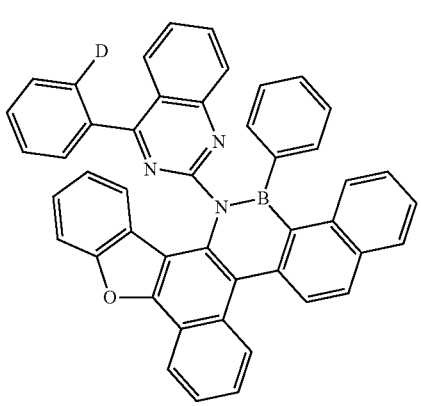
108 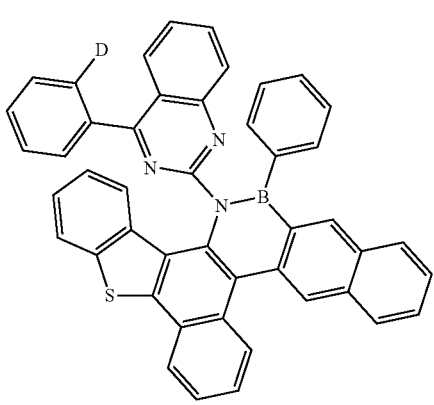

121
-continued
109
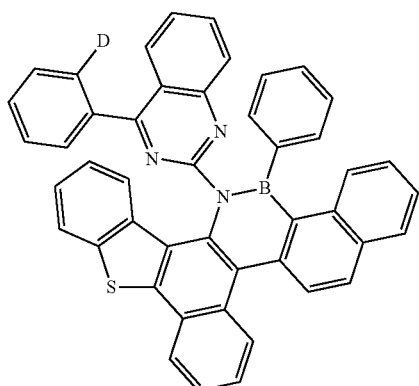
110
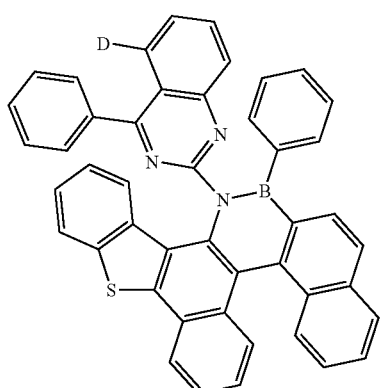
111
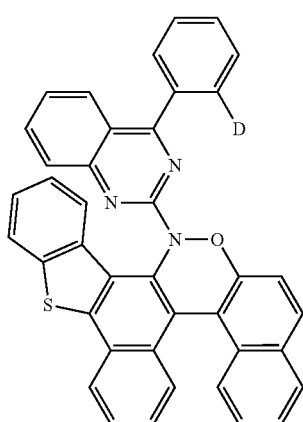
112
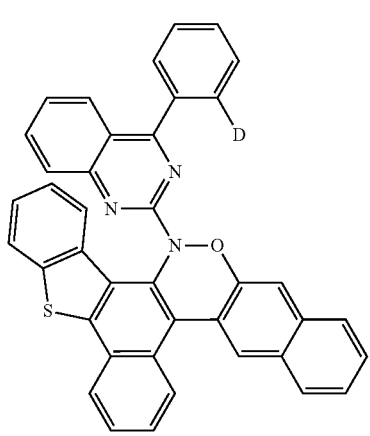
122
-continued
113
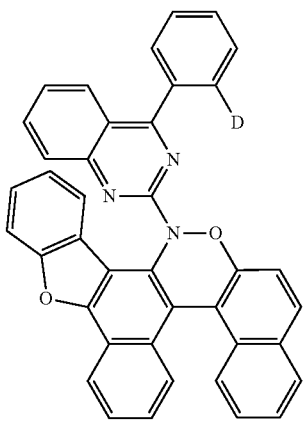
114
116

123
-continued

117

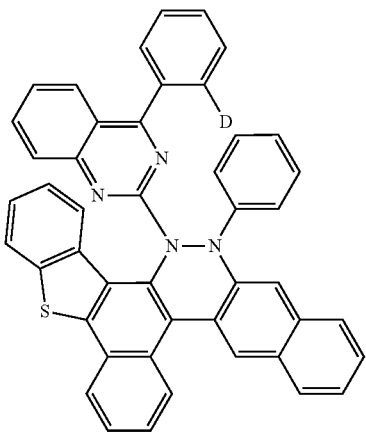

118

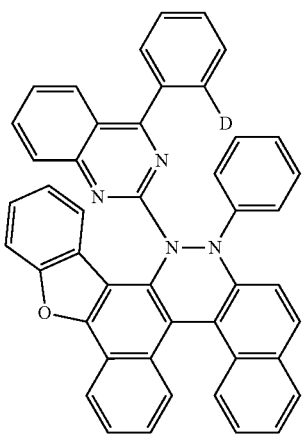

124
-continued

119

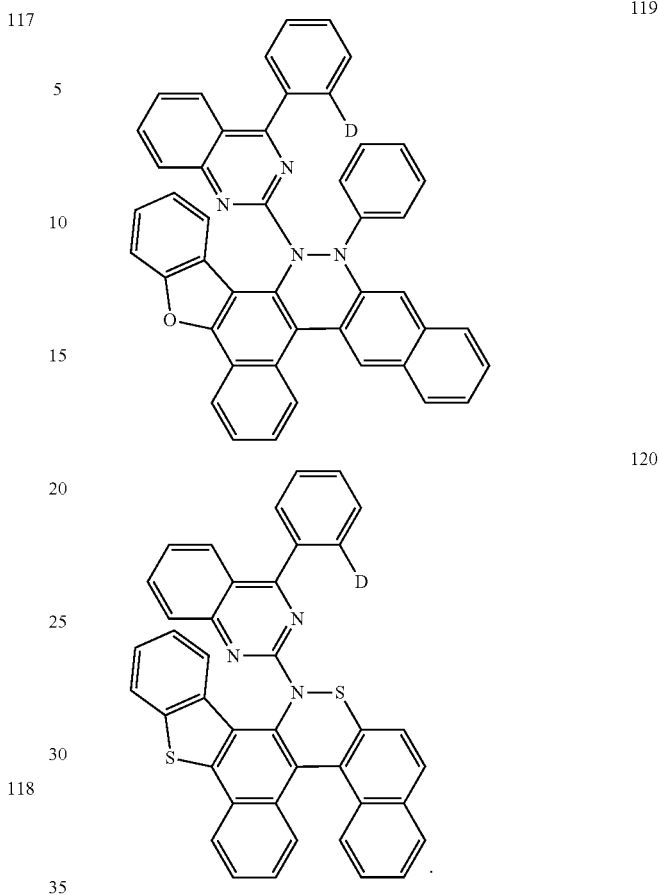

120

5. A method for preparing a fused polycyclic compound according to claim 1, wherein when $T^1$ is selected from $C(R^{24})_2$, that is, the fused polycyclic compound has a structure of General Formula IV-1, and $T^4$ is selected from Cl $C(R^{24})_2$ or Br $C(R^{24})_2$, the preparation method comprises:
  subjecting the compound of Formula (E) used as a raw material to a cyclization reaction in the presence of a catalyst to obtain an intermediate compound (F); and
  coupling the intermediate compound (F) to the compound of Formula (G) in the presence of a catalyst, to obtain the compound of General Formula IV-1; and
the route for preparing the compound of General Formula IV-1 is shown below:

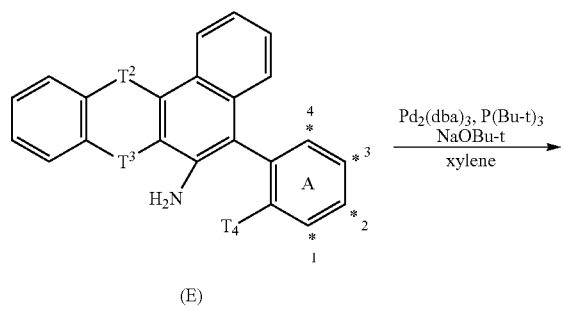

(E)

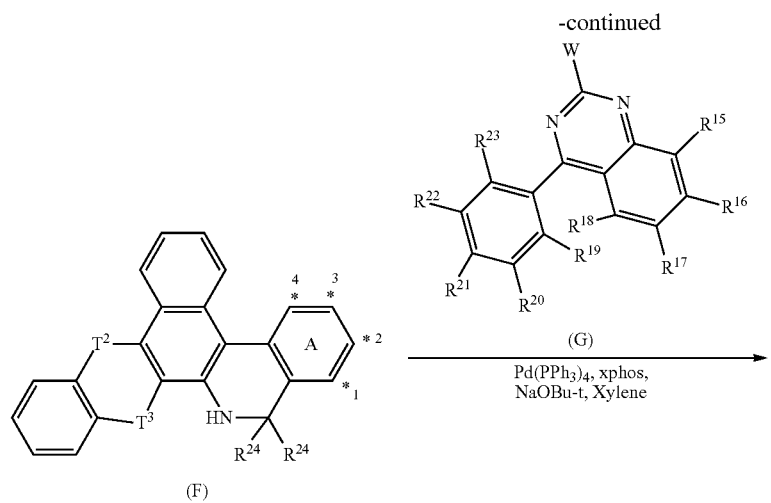

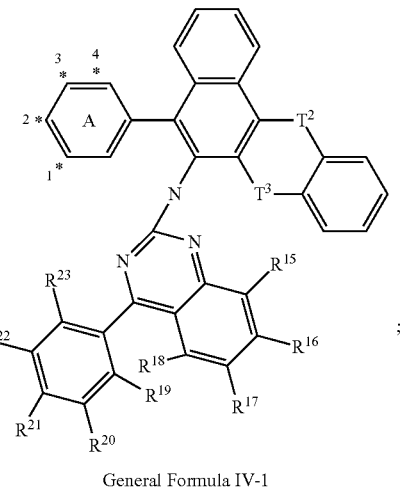

(G)

General Formula IV-1 alternatively, when $T^1$ is selected from $BR^{24}$, that is, the fused polycyclic compound has a structure of General Formula IV-2, and $T^4$ is selected from hydrogen, the preparation method comprises:

reacting the compound of Formula (E) used as a raw material with the compound of Formula (H) in the presence of a catalyst to obtain an intermediate compound (J); and coupling the intermediate compound (J) to the compound of Formula (G) in the presence of a catalyst, to obtain the compound of General Formula IV-2; and the route for preparing the compound of General Formula IV-2 is shown below:

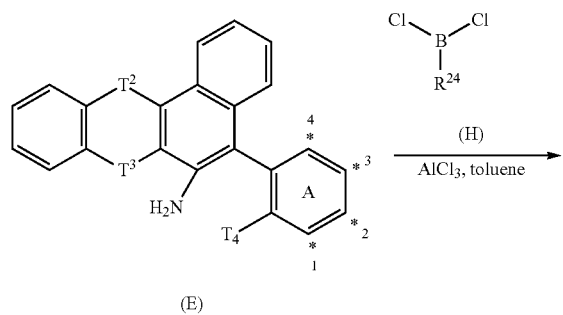

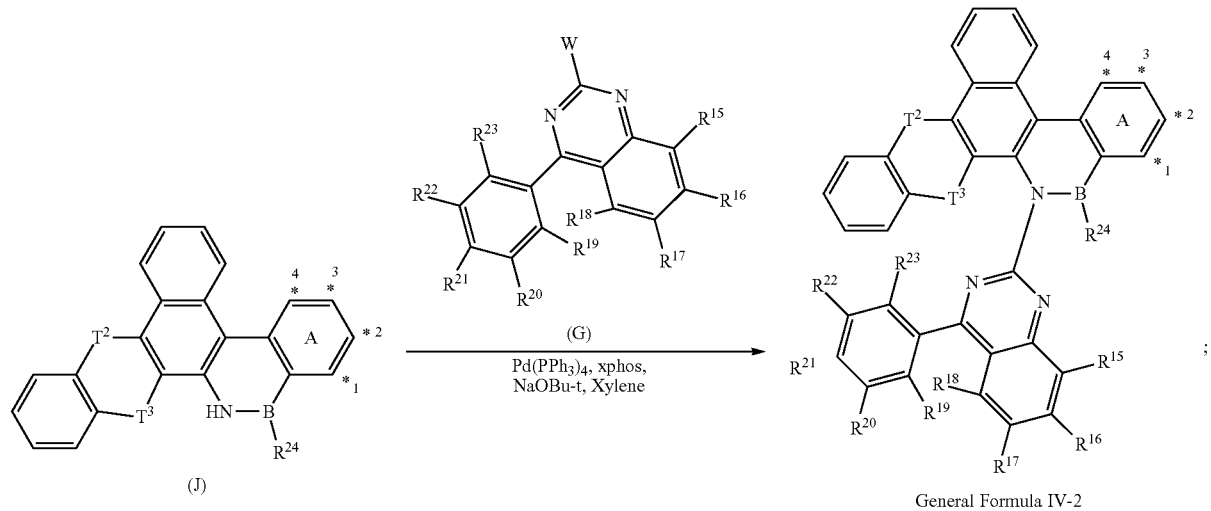

General Formula IV-2 alternatively, when T¹ is selected from S, that is, the fused polycyclic compound has a structure of General Formula IV-3, and T⁴ is selected from mercapto, the preparation method comprises:

reacting the compound of Formula (E) used as a raw material in the presence of a catalyst to obtain an intermediate compound (K); and coupling the intermediate compound (K) to the compound of Formula (G) in the presence of a catalyst, to obtain the compound of General Formula IV-3; and the route for preparing the compound of General Formula IV-3 is shown below:

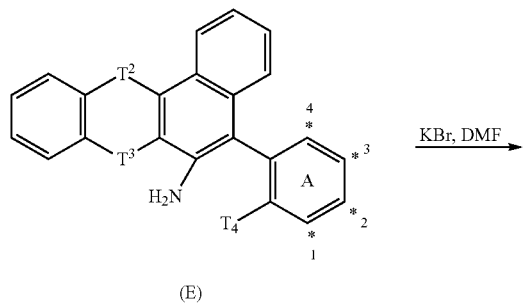

(E)

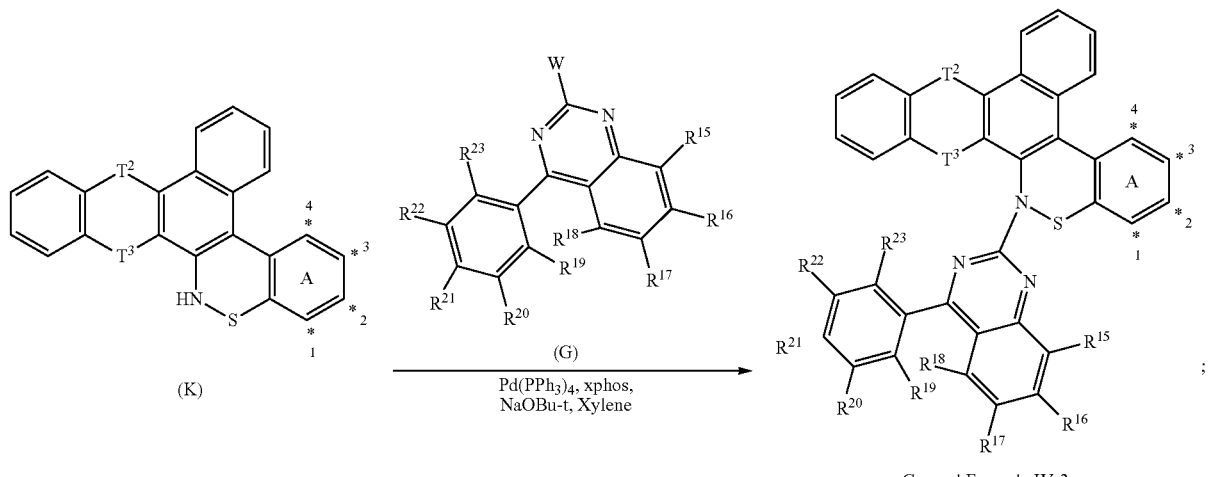

alternatively, when T¹ is selected from O, that is, the fused polycyclic compound has a structure of General Formula IV-4, and T⁴ is selected from hydroxyl, the preparation method comprises:

reacting the compound of Formula (E) used as a raw material in the presence of a catalyst to obtain an intermediate compound (K-1); and coupling the intermediate compound (K-1) to the compound of Formula (G) in the presence of a catalyst, to obtain the compound of General Formula IV-4; and the route for preparing the compound of General Formula IV-4 is shown below:

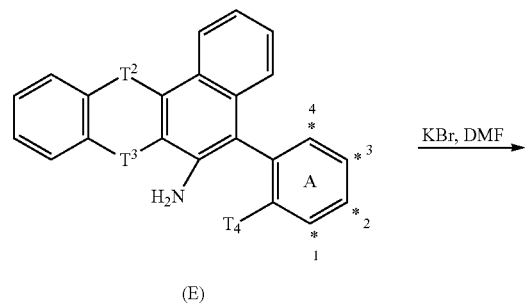

(E)

-continued

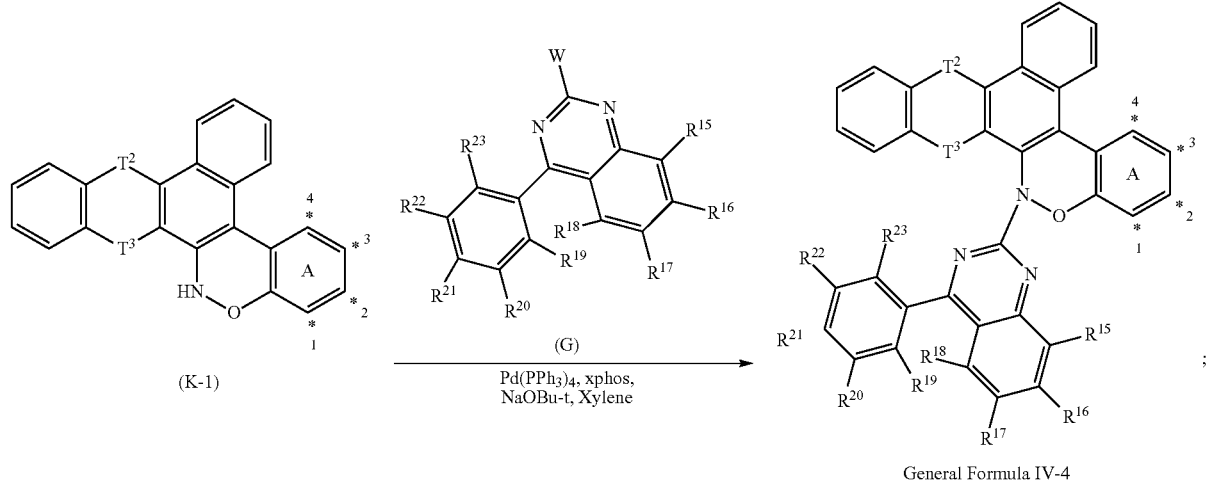

(G)
Pd(PPh₃)₄, xphos,
NaOBu-t, Xylene

General Formula IV-4 alternatively, when $T^1$ is selected from $PR^{24}$, that is, the fused polycyclic compound has a structure of General Formula IV-5, and $T^4$ is selected from hydrogen, the preparation method comprises:

reacting the compound of Formula (E) used as a raw material in the presence of a catalyst to obtain an intermediate compound (L); reacting the intermediate compound (L) in the presence of a catalyst to obtain an intermediate compound (M); coupling the intermediate compound (M) to the compound of Formula (N) in the presence of a catalyst to obtain an intermediate compound (O); and coupling the intermediate compound (O) to the compound of Formula (G) in the presence of a catalyst, to obtain the compound of General Formula IV-5; and the route for preparing the compound of General Formula IV-5 is shown below:

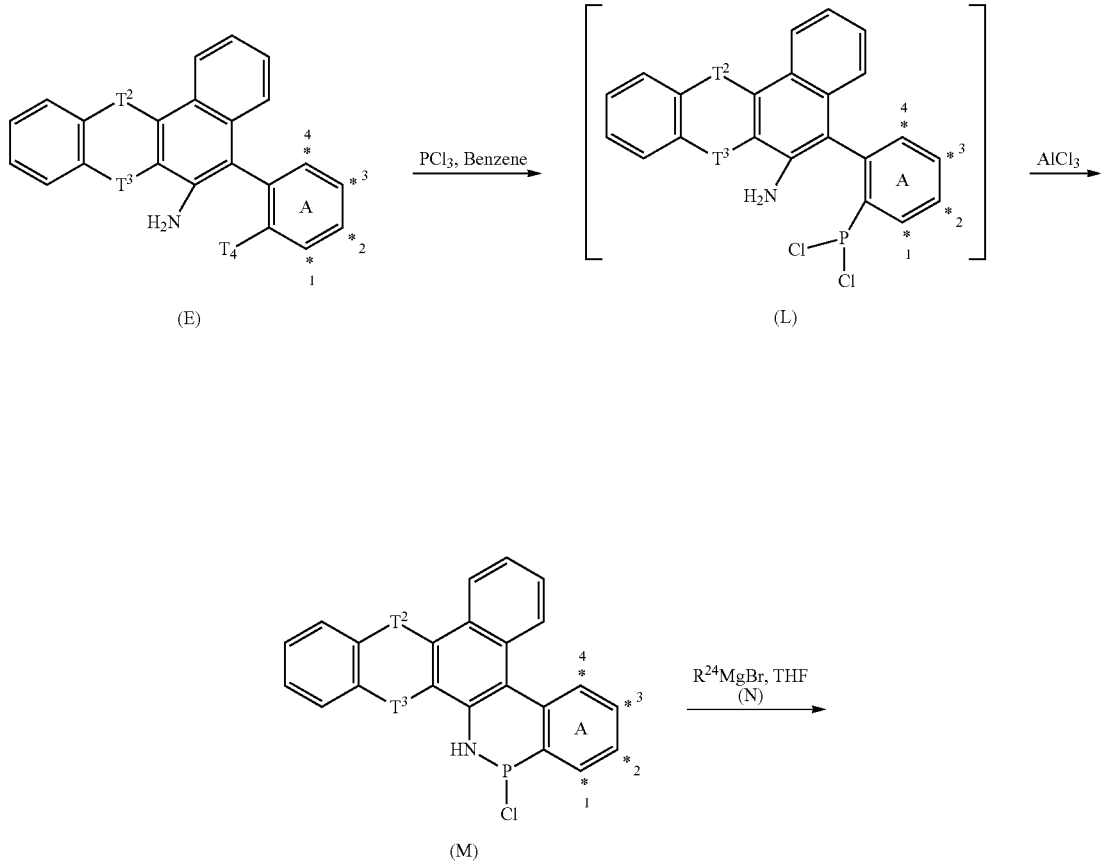

-continued

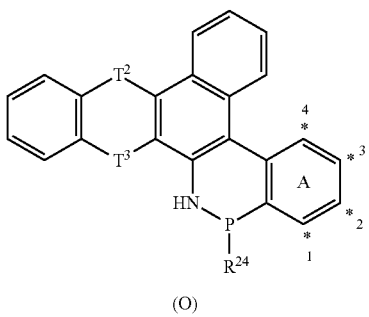 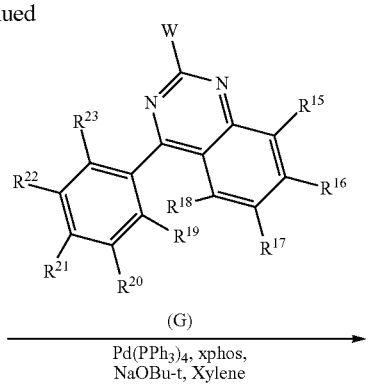

(O)    (G)
Pd(PPh₃)₄, xphos,
NaOBu-t, Xylene →

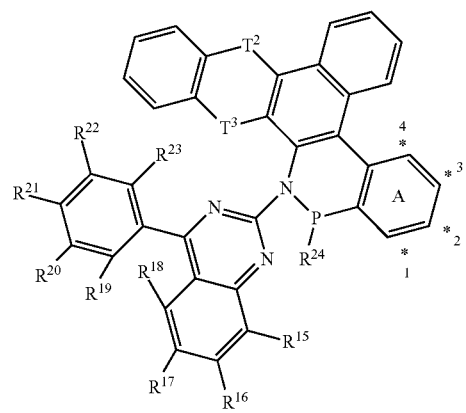

General Formula IV-5 alternatively, when T¹ is selected from NR²⁴, that is, the fused polycyclic compound has a structure of General Formula IV-6, and T⁴ is selected from nitro, the preparation method comprises:

reacting the compound of Formula (D) used as a raw material in the presence of a catalyst to obtain an intermediate compound (P); and reacting the intermediate compound (P) with the compound of Formula (Q) and then the compound of Formula (G), to obtain the compound of General Formula IV-6; and the route for preparing the compound of General Formula IV-6 is shown below:

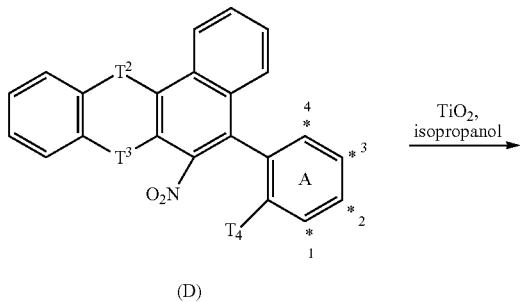

(D)   TiO₂, isopropanol →

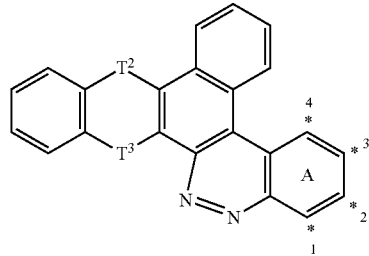

(P)

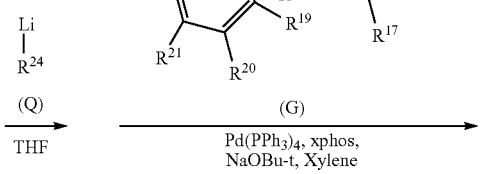

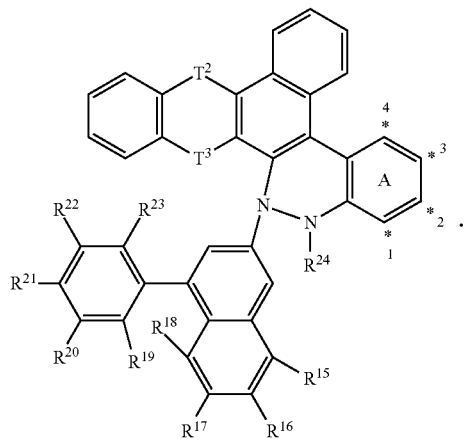

General Formula IV-6

6. The method for preparing a fused polycyclic compound according to claim 5, wherein the compound of Formula (E) is prepared through a method comprising:

nitrifying the compound of Formula (A) used as a starting raw material in the presence of a catalyst to obtain an intermediate compound (B); coupling the intermediate compound (B) to the compound of Formula (C) in the presence of a catalyst to obtain an intermediate compound (D); and reducing the intermediate compound (D) in the presence of a catalyst, to obtain the compound of Formula E; and the route for preparing the compound of Formula E is shown below:

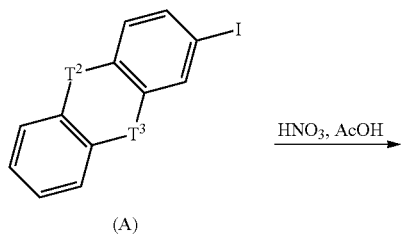

(A)

$\xrightarrow{\text{HNO}_3, \text{AcOH}}$

-continued

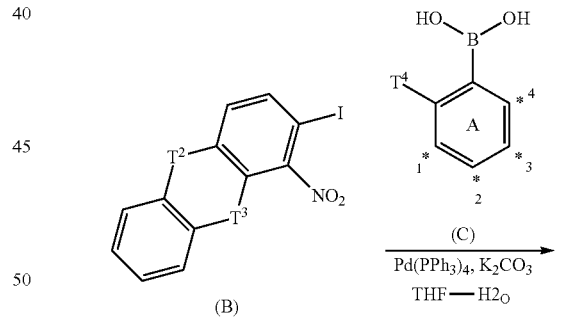

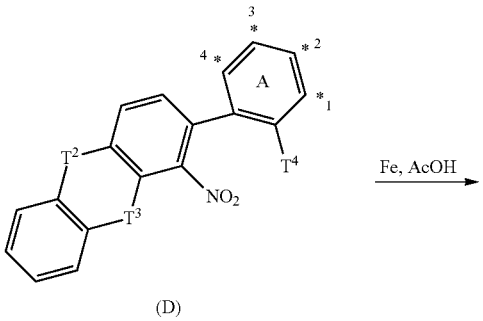

(D)

$\xrightarrow{\text{Fe, AcOH}}$

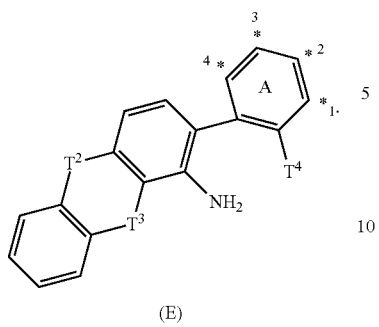

(E)

7. An electronic device, comprising any one or a combination of at least two of the fused polycyclic compounds according to claim 1, wherein the electronic device is any one of an organic light emitting diode, an organic field effect transistor, an organic thin film transistor, an organic light emitting transistor, an organic integrated circuit, an organic solar cell, an organic field quenching device, a light emitting electrochemical cell, an organic laser diode or an organic photoreceptor.

8. The electronic device according to claim 7, which is an organic light emitting device comprising an anode, a cathode, and an organic thin film layer between the anode and the cathode, wherein the organic thin film layer comprises any one or a combination of at least two of the fused polycyclic compounds according to claim 1, wherein the organic thin film layer comprises a light-emitting layer, and also any one or a combination of at least two of a hole injection layer, a hole transport layer, a hole blocking layer, an electron transport layer, an electron injection layer, an electron blocking layer, and a charge transport layer, wherein the light-emitting layer comprises any one or a combination of at least two of the fused polycyclic compounds according to claim 1; and the light-emitting layer comprises a host material and a guest material; and the host material in the light-emitting layer comprises any one or a combination of at least two of the fused polycyclic compounds according to claim 1.

9. A display device, comprising an electronic device according to claim 7.

10. A lighting device, comprising an electronic device according to claim 7.

11. The fused polycyclic compound according to claim 2, wherein when $T^2$ is a single bond, $T^3$ is S or O.

12. The fused polycyclic compound according to claim 2, having any one of the molecular structures shown below:

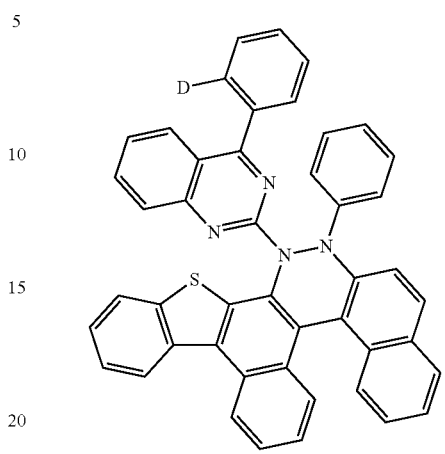

4

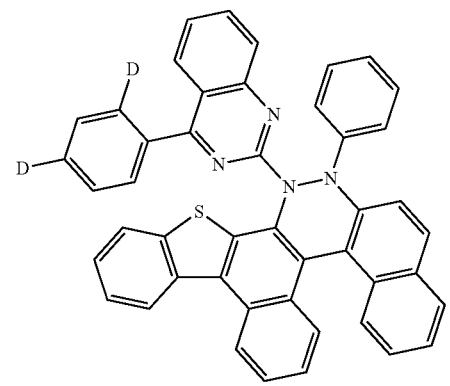

5

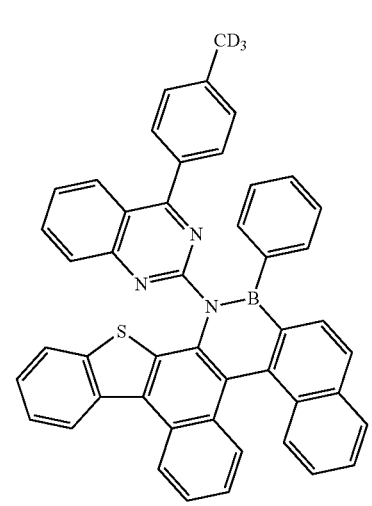

6

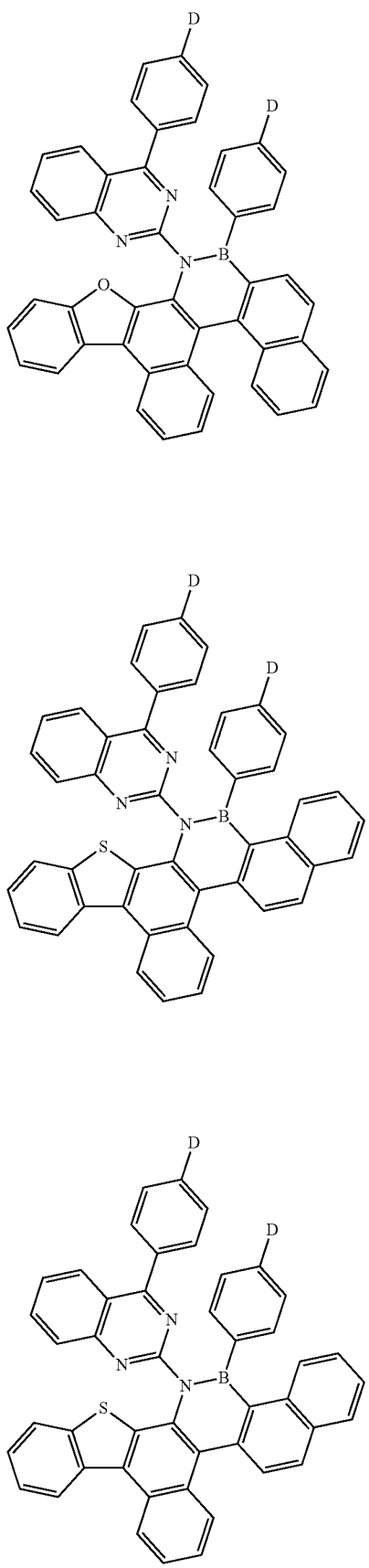
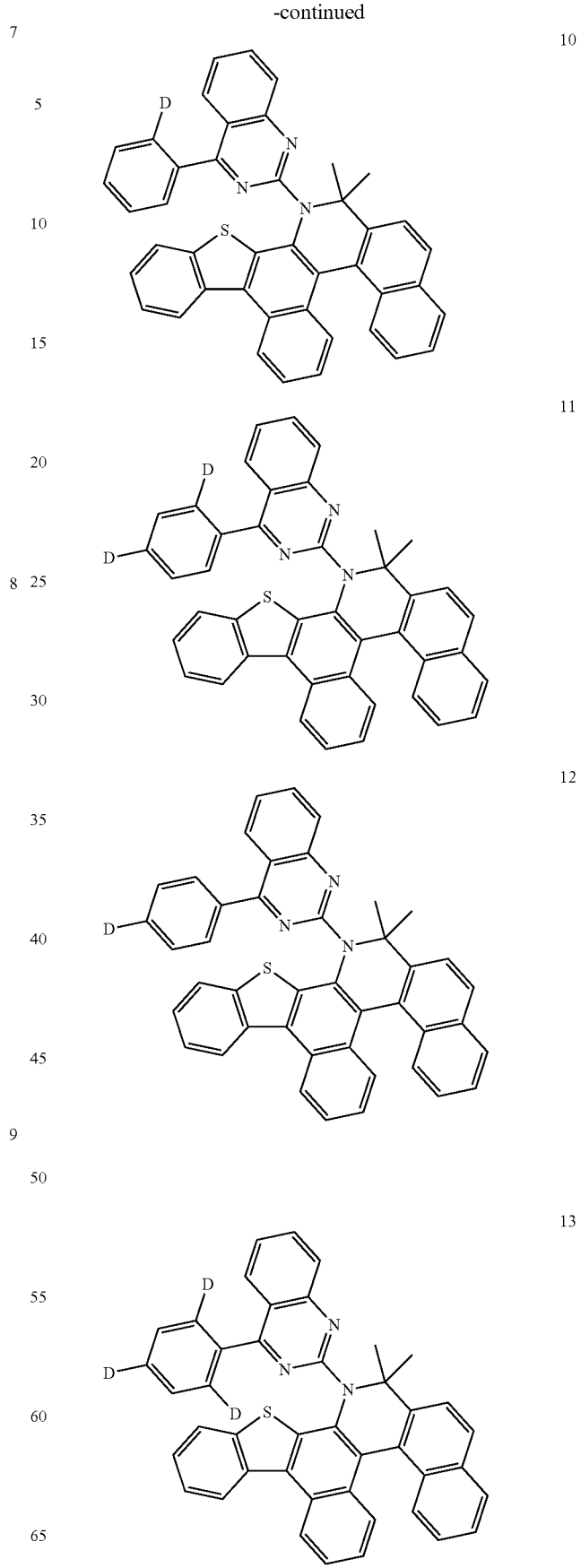

18
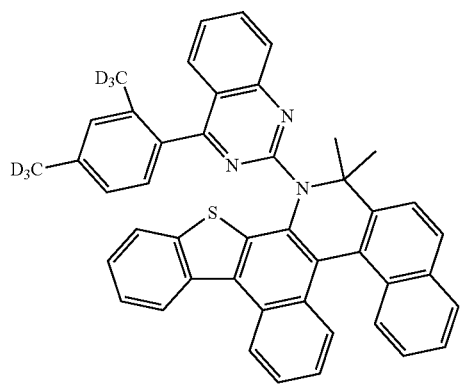
19
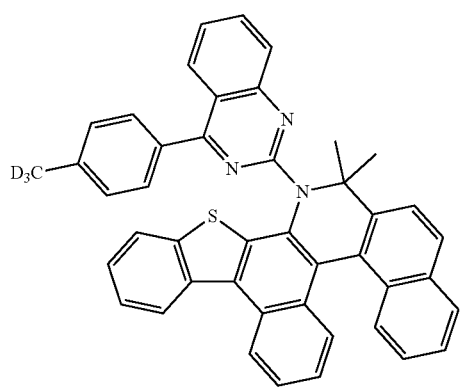
20
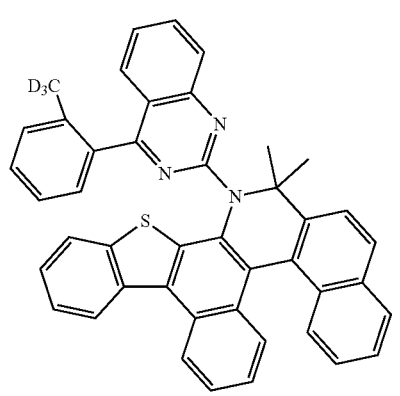
22
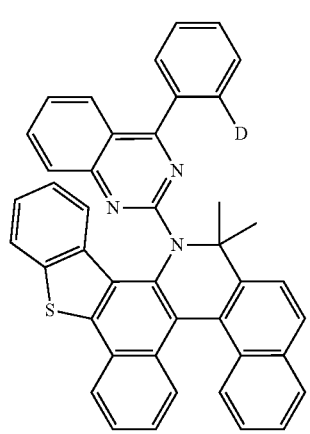
23
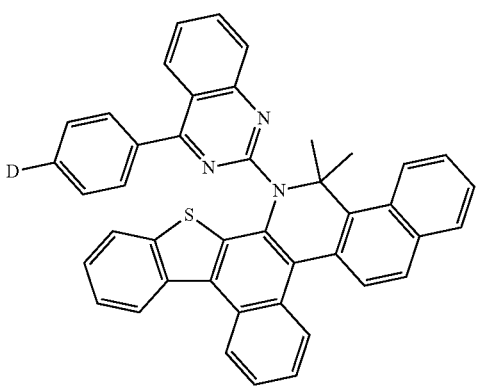
24
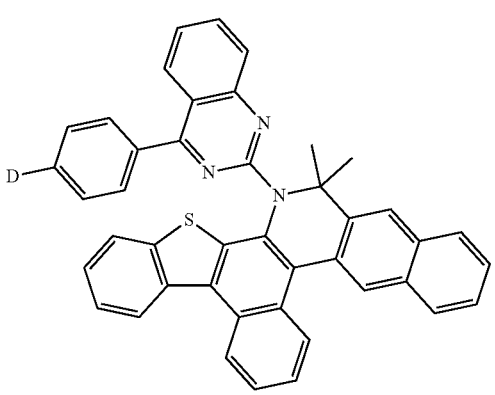
25
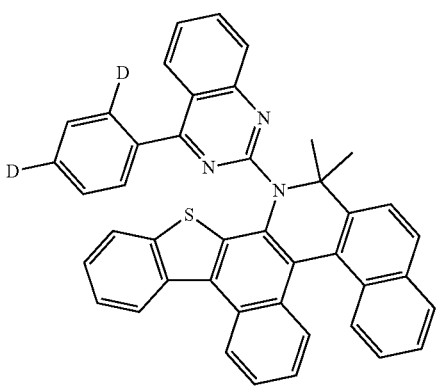
26
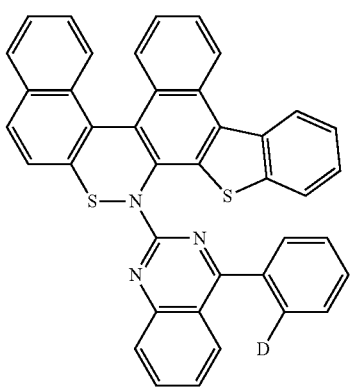

27
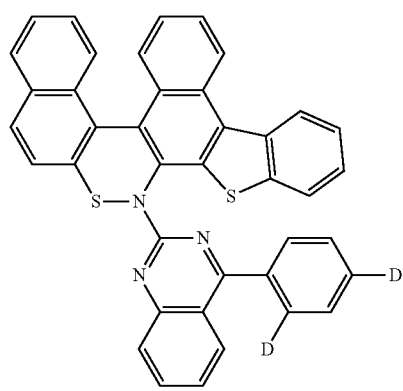
28
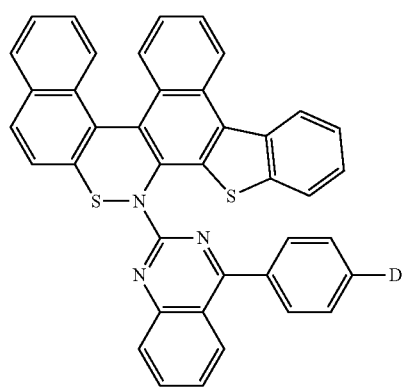
29
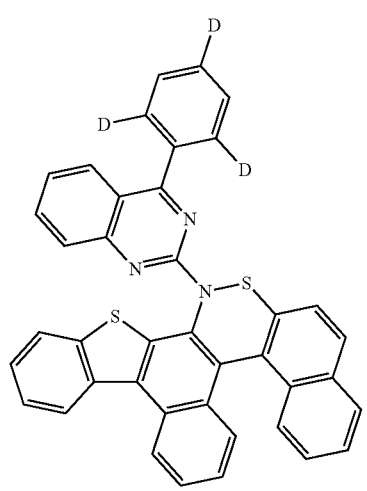
30
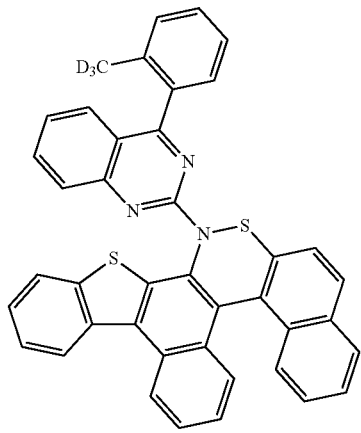
31
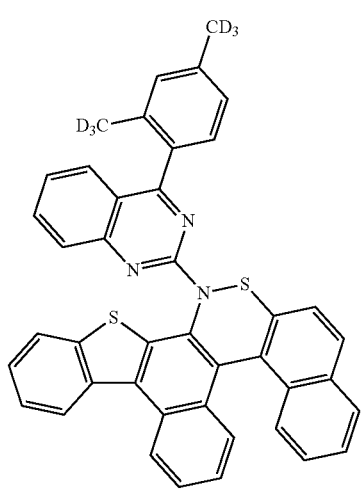
32
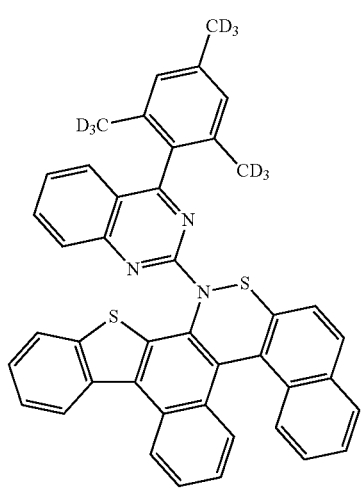

33
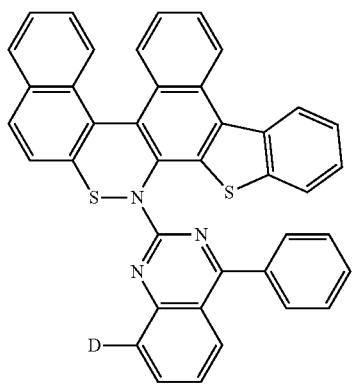
34
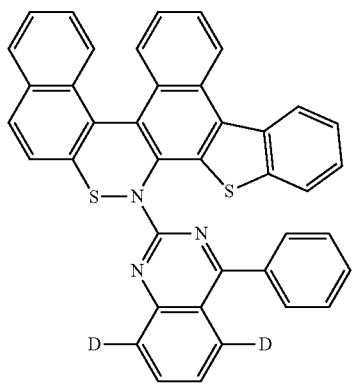
35
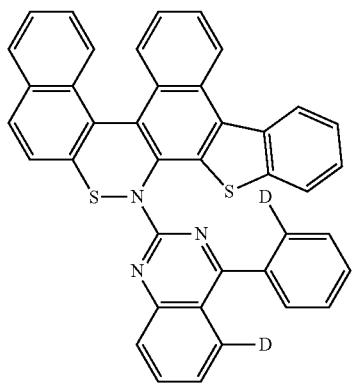
41
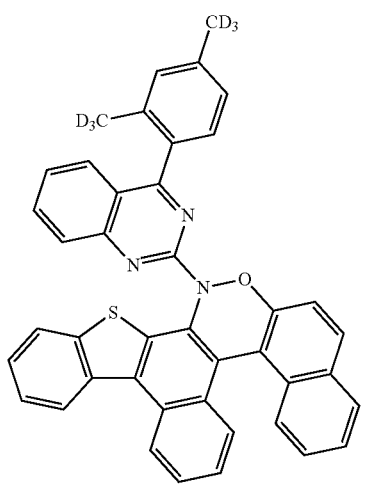
42
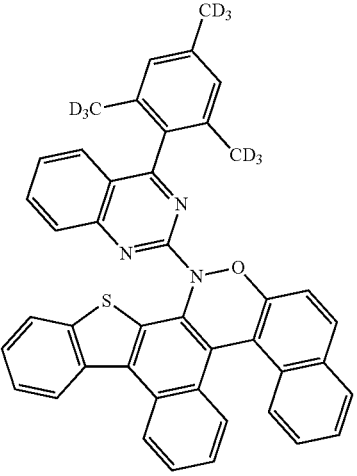
43
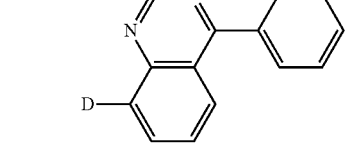
44
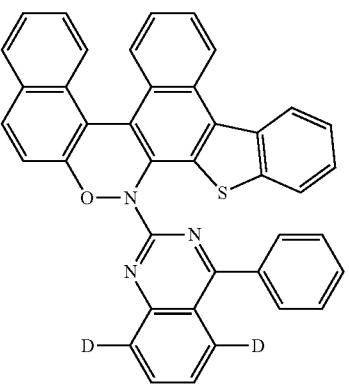
45
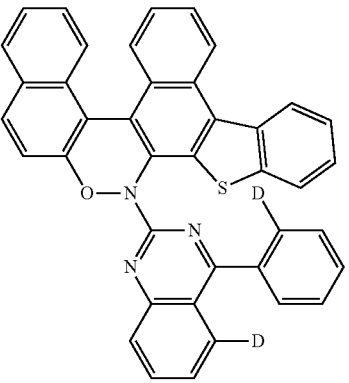

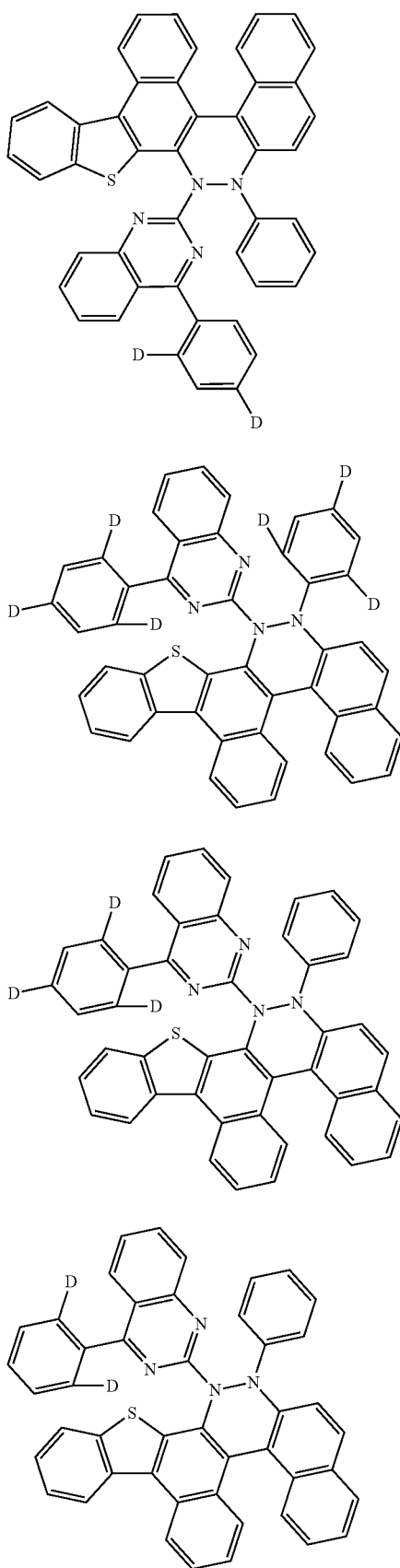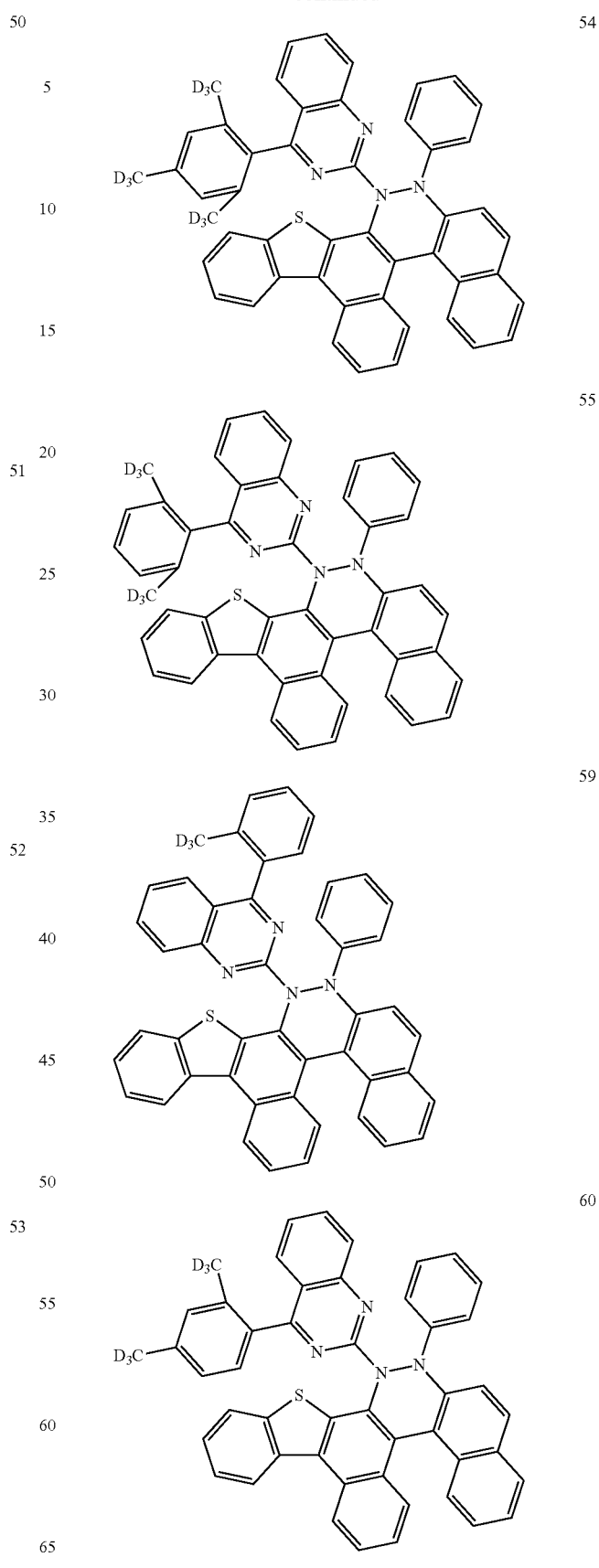

-continued
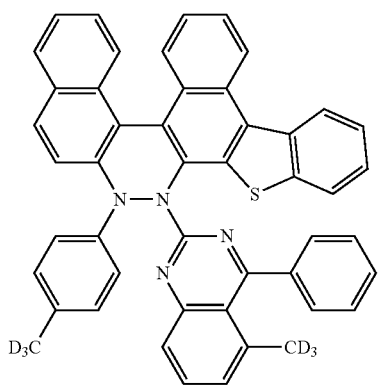
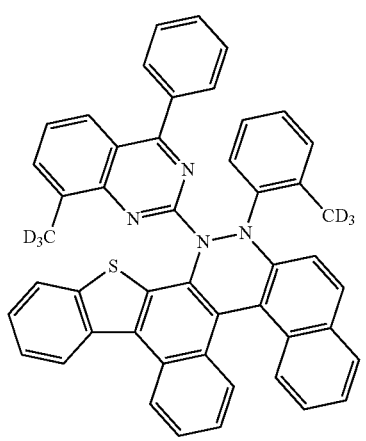
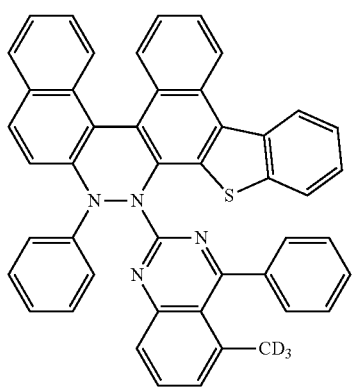
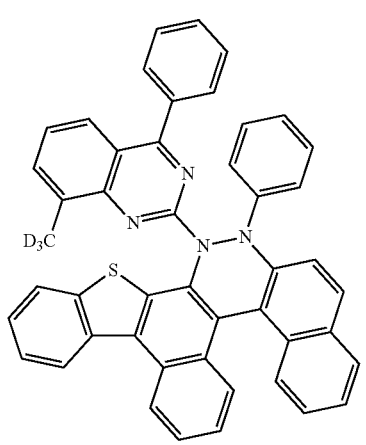
-continued
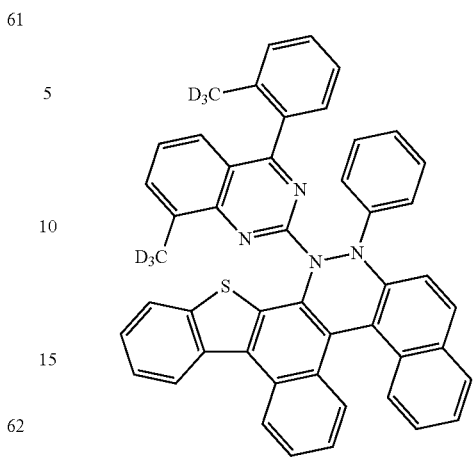
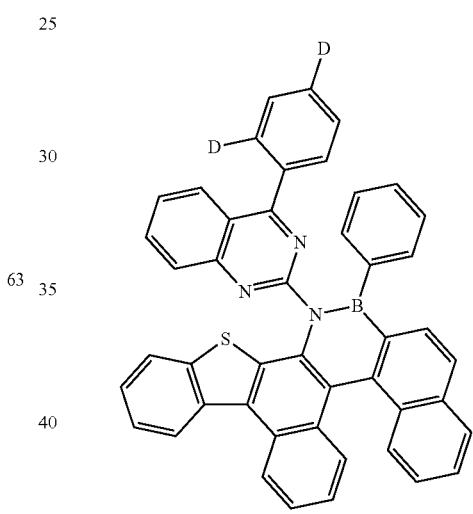
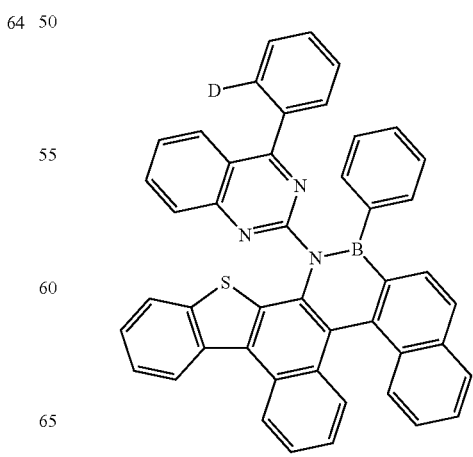

-continued
68
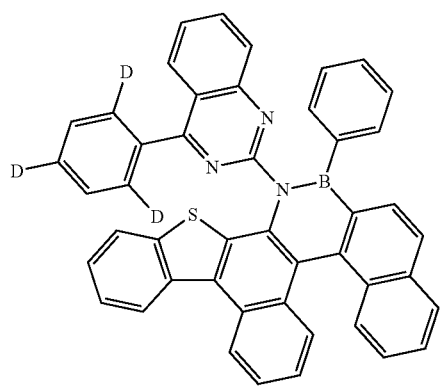
69
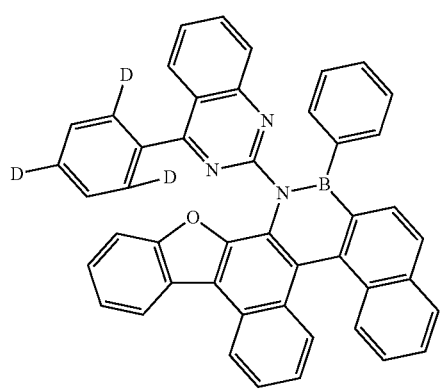
70
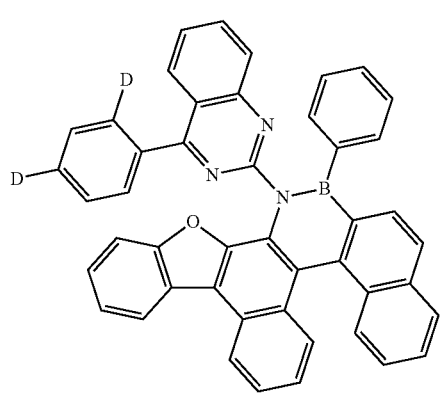
71
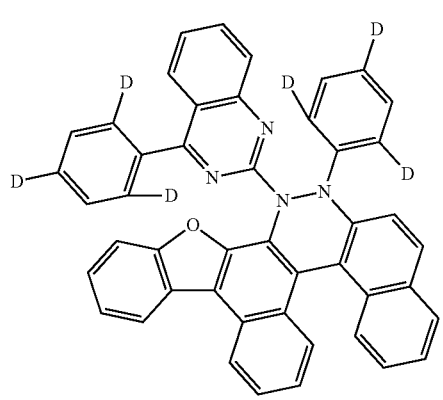
-continued
72
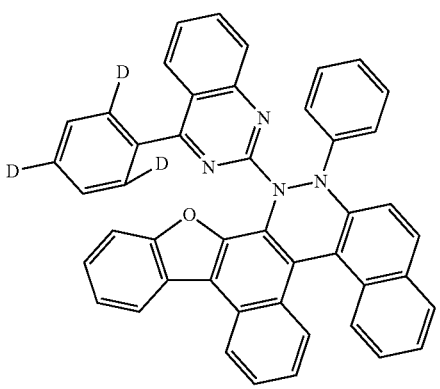
73
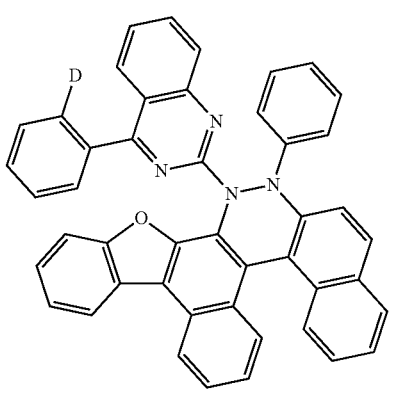
74
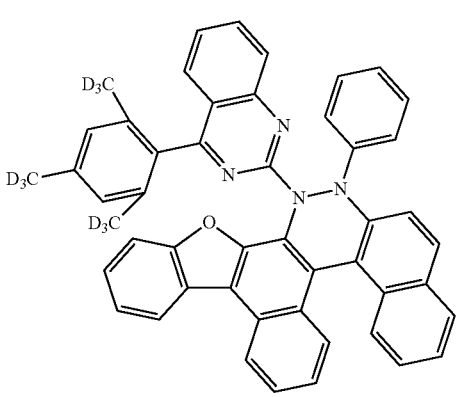
75
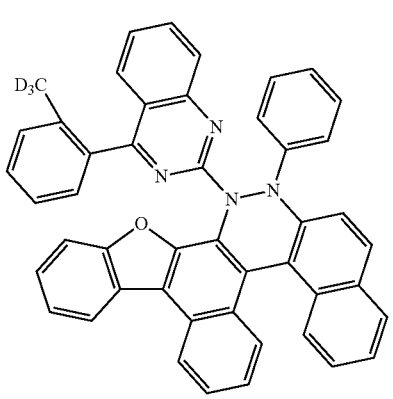

151
-continued
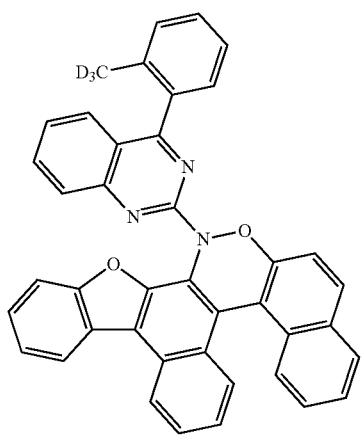
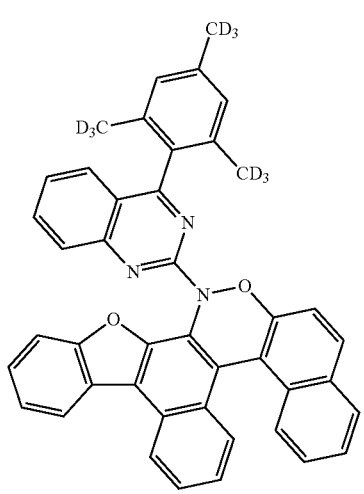
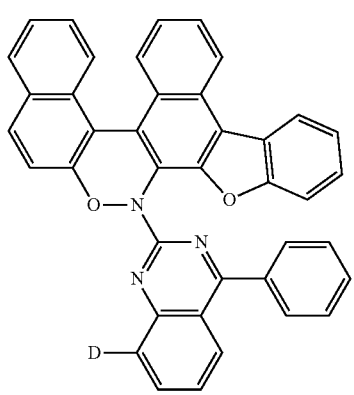
152
-continued
76
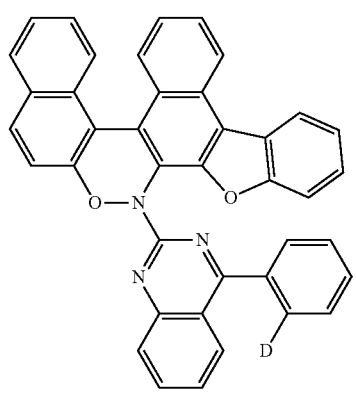
77
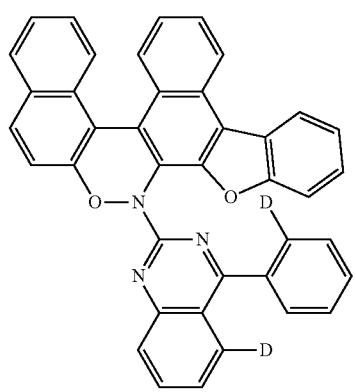
78
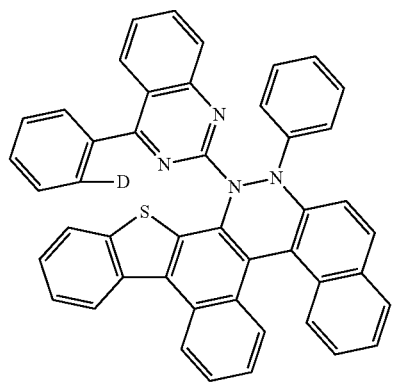

-continued
85
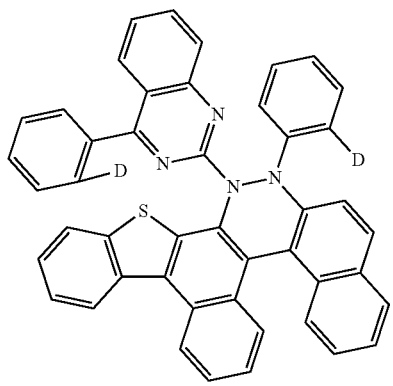
86
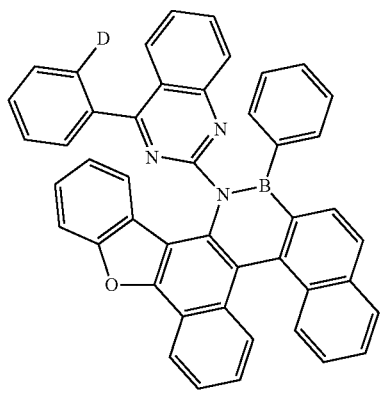
87
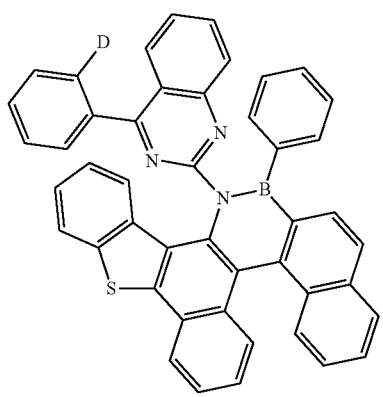
88
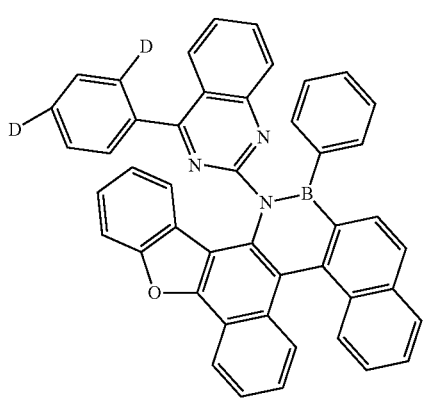
-continued
89
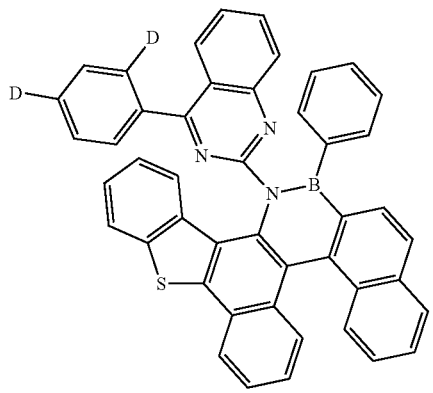
90
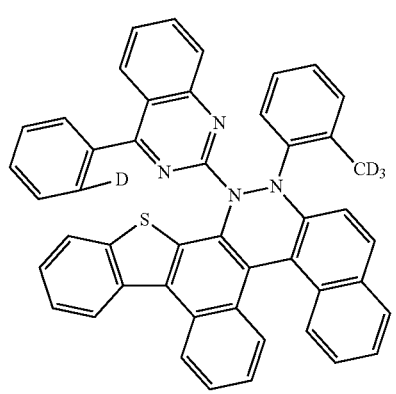
91
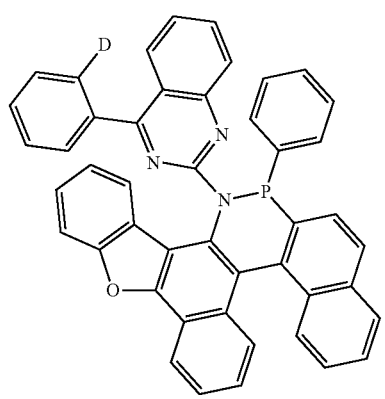
92
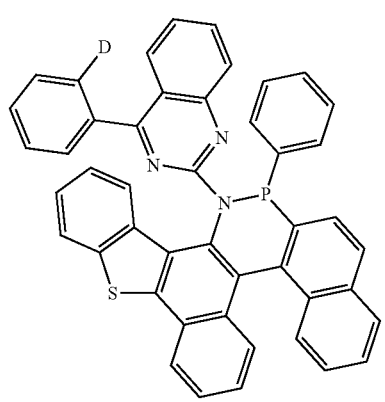

93
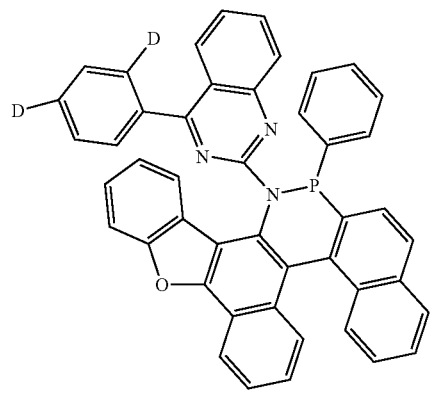
94
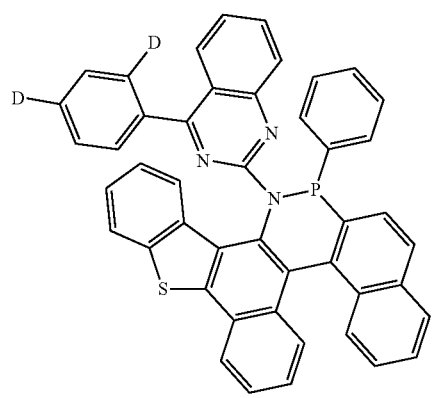
95
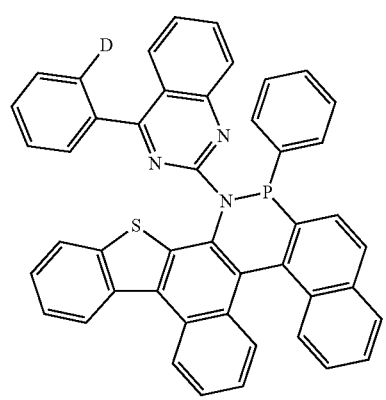
96
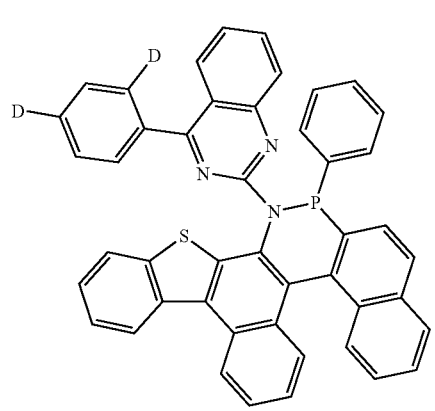
97
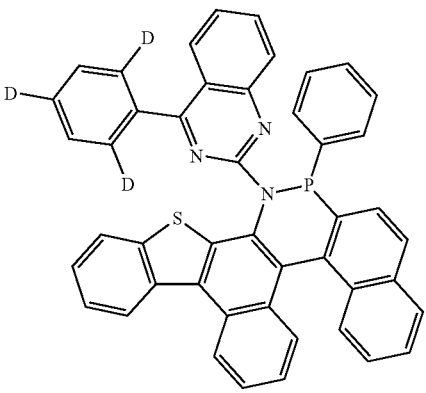
98
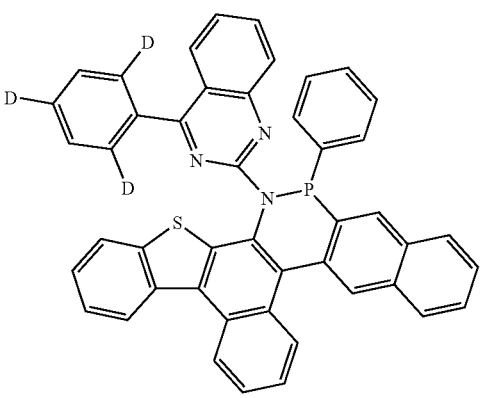
99
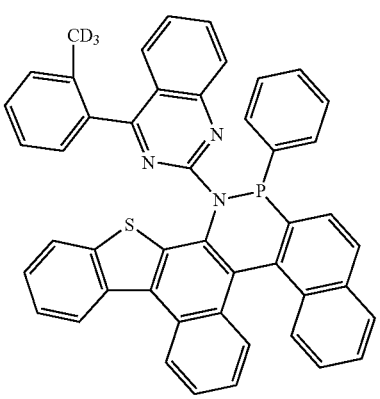
100
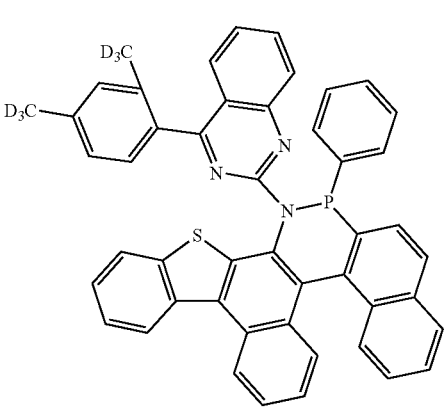

157
-continued
101
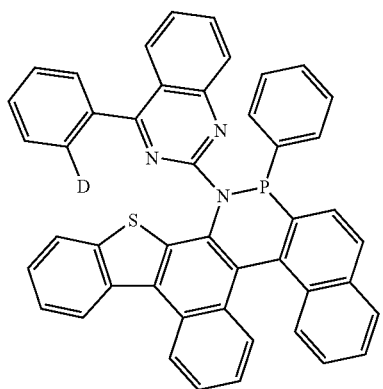
102
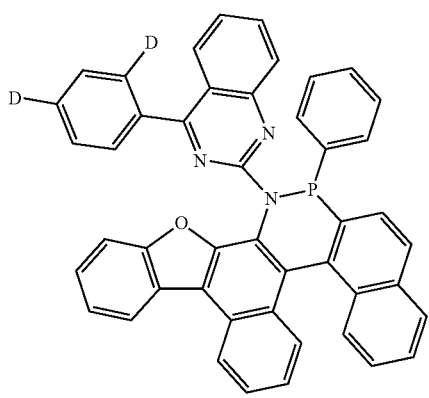
103
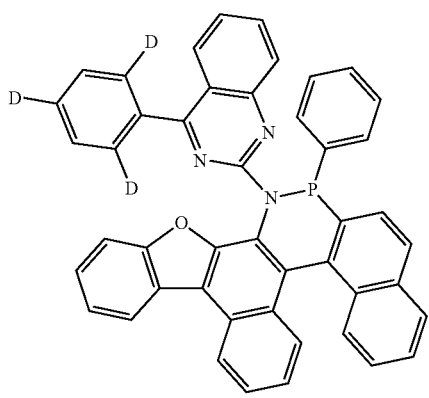
104
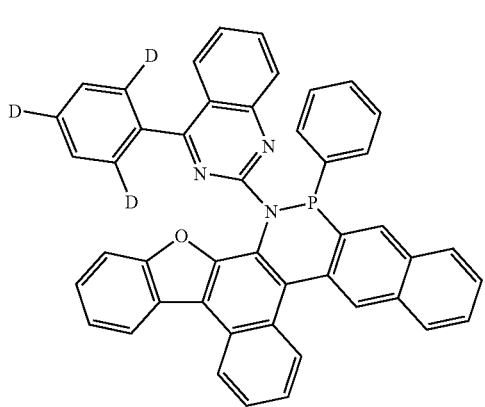
158
-continued
105
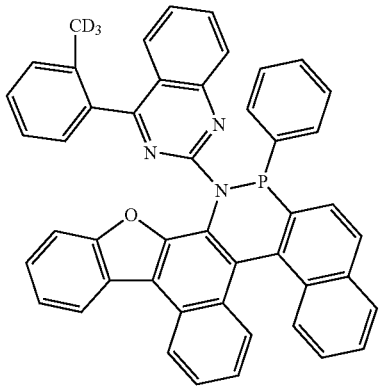
106
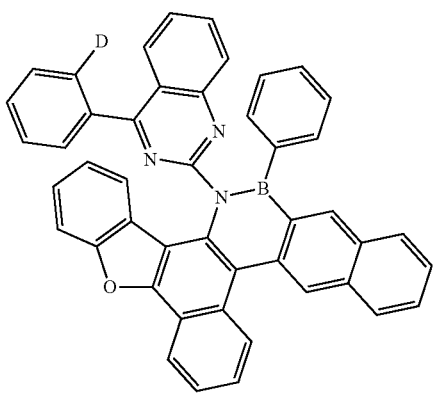
107
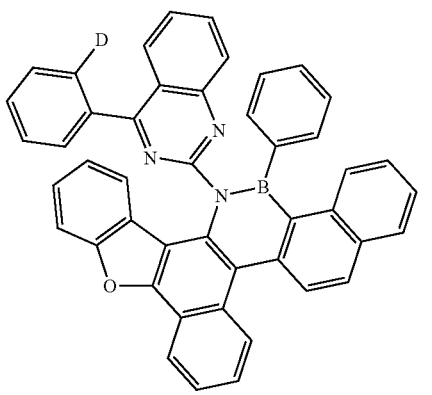
108
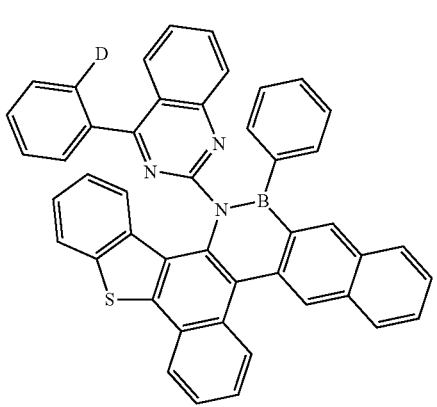

109
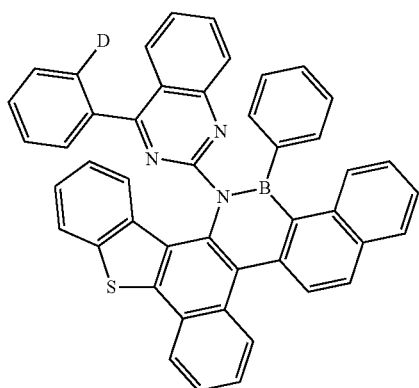
110
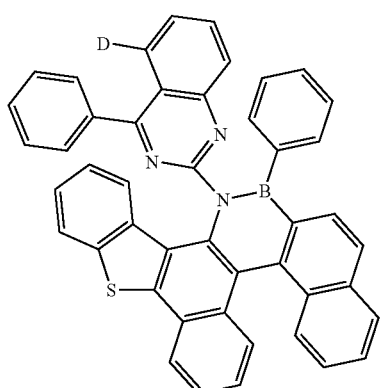
111
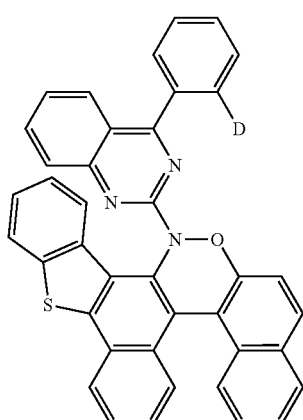
112
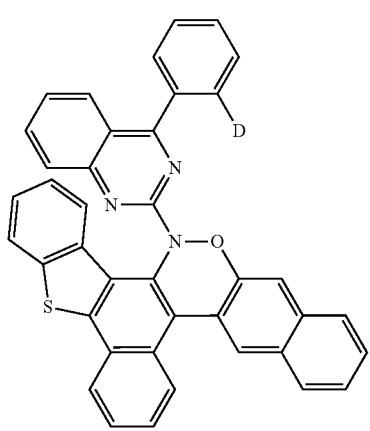
113
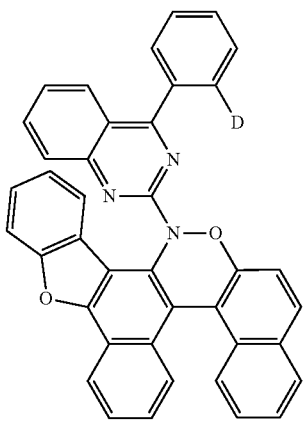
114
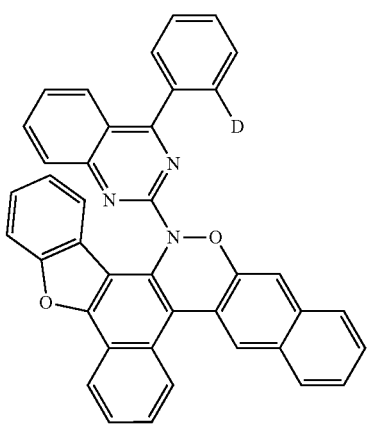
116
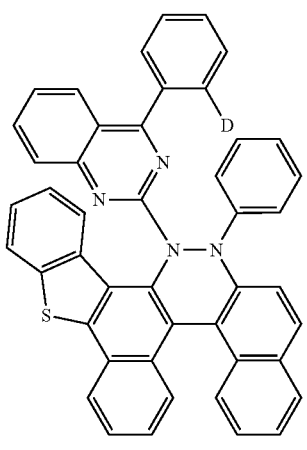

161
-continued
117
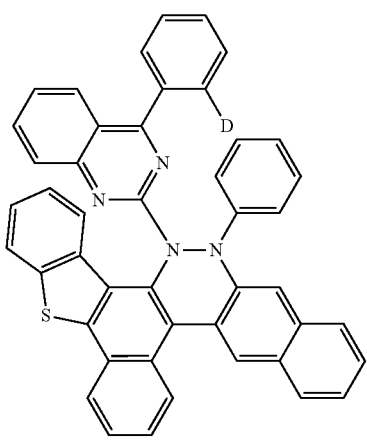
118
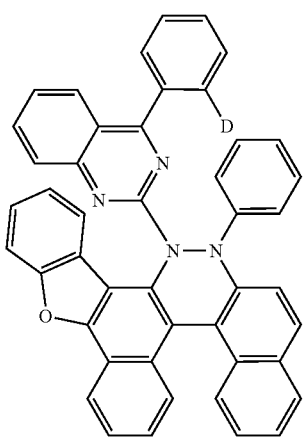
162
-continued
119
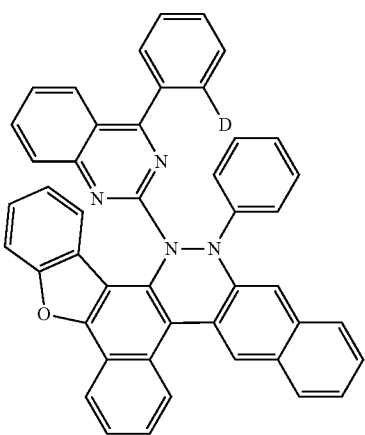
120
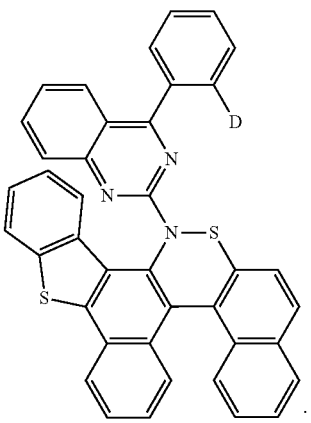
* * * * *